United States Patent [19]

Stritzke

[11] Patent Number: 5,249,122
[45] Date of Patent: Sep. 28, 1993

[54] METHOD AND APPARATUS FOR FORMING IMAGES USING ORTHOGONAL POLYNOMIALS FOR TEMPORAL DECONVOLUTION

[75] Inventor: Peter Stritzke, White Plains, N.Y.

[73] Assignee: Mount Sinai School of Medicine of the City University of New York, New York, N.Y.

[21] Appl. No.: 494,121

[22] Filed: Mar. 15, 1990

[51] Int. Cl.$^5$ .............................................. G06F 15/42
[52] U.S. Cl. .................................................. 364/413.07
[58] Field of Search ........................ 364/413.07, 715.01

[56] References Cited

U.S. PATENT DOCUMENTS 4,111,191  9/1978  Shaw.
4,326,539  4/1982  Obermajer.
4,458,688  7/1984  Von Behren.
4,633,400  12/1986  Chittineni.

OTHER PUBLICATIONS

Kuruc, et al., "An Improved Deconvolution Technique for the Calculation of Renal Retention Functions", Computer and Biomedical Research, 15:46-56 (1982).
Hunt, "The Inverse Problem of Radiography", Mathematical Biosciences, 8:161-179 (1970).
Wu, et al., "Tc-99m HIDA Dosimetry in Patients with Various Hepatic Disorders", J. Nucl. Med., 25:905-912 (1984).
Siegel, et al., "The Buildup Factor: Effect of Scatter on Absolute Volume Determination", J. Nucl. Med., 26:390-394 (1985).
Stritzke, et al., "Performance of Quantitative Functional Imaging Using Optimal Two-Dimensional Restoration and Temporal Deconvolution of Dynamic Scintigraphic Studies", in: Computer Assisted Radiography, Springer-Verlag, pp. 697-702 (1987).
Van Stekelenburg, et al., "A Three-compartment Model for the Transport and Distribution of Hippuran", Phys. Med. Biol., 21:74-84 (1976).
Szabo, et al., "Model identification and estimation of organ-function parameters using radioactive tracers and the impulse-response function", Eur. J. Nucl. Med., 11:265-274 (1985).
King, et al., "Digital Restoration of Indium-111 and Iodine-123 SPECT Images with Optimized Metz Filters", J. Nucl. Med., 27:1327-1336 (1986).
Van Huffel, et al., "Reliable and efficient deconvolution technique based on total linear least squares for calculating the renal retention function", Med. & Biol. Eng. & Comput., 25:26-33, (1987).
Montz et al., "Functional Imaging of Thyroidal $^{123}$I-Clearance", NucCompact, 13:176-178 (1982).
Twomy, "The Application of Numerical Filtering to the Solution of Integral Equations Encountered in Indirect Sensing Measurements", J. of the Franklin Institute, 279:95-109 (1965).
Phillips, "A Technique for the Numerical Solution of Certain Integral Equations of the First Kind", J. Assoc. Comp. Mach., 9:84-97 (1962).
Valentinuzzi, et al., "Discrete Deconvolution", Medical and Biological Engineering, 13:123-125 (1975).
Gremmel, et al., "Auswertung von Isotopennephrogrammen durch die Entfaltungsmethode", Nucl.-Med., 18:46-51 (1979).
Kenny, et al., "Deconvolution analysis of the scintillation camera renogram", B. J. of Radiology, 48:481-486 (1975).
Fleming, et al., "A Technique for the Deconvolution of the Renogram", Phys. Med. Biol., 19:546-549 (1974).
King et al., "Use of a nonstationary temporal Wiener filter in nuclear medicient", Eur. J. Nucl. Med., 10:458-461 (1985).

(List continued on next page.)

Primary Examiner—Gail O. Hayes
Attorney, Agent, or Firm—Brumbaugh, Graves, Donohue & Raymond

[57] ABSTRACT

The present invention disclose a tool in the form of an array processor, or, in the alternative, a method, wherein, multi-pixel images containing digitized information can be deconvolved in conjunction with other information to extract information contained in multiple time related images or similar time sequential data.

6 Claims, 22 Drawing Sheets

OTHER PUBLICATIONS

Knesaurek, et al., "Comparison of three deconvolution techniques in renography", Eur. J. Nucl. Med., 9:254–256 (1984).

Van Stekelenburg, "Hippuran Transit Times in the Kidney: a New Approach", Phys. Med. Biol., 23:291–301 (1978).

Diffey, et al., "The $^{99m}$Tc-DTPA Dynamic Renal Scan With Deconvolution Analysis", J. Nucl. Med., 17:352–355 (1976).

Keller, et al., "Direct Determination of the Attenuation Coefficient for Radionuclide Volume Measurements", J. Nucl. Med., 28:102–107 (1987).

Nimmon, et al., "Practical Application of Deconvolution Techniques to Dynamic Studies", IAEA, pp. 367–388 (1981).

Zierler, "Theoretical Basis of Indicator-Dilution Methods for Measuring Flow and Volume", Circ. Research, 10:393–407 (1962).

Chackett, "The Application of Transform Methods to Hippuran Renograms", Phys. Med. Biol., 23:1199–1202 (1978).

Kaplan et al., "The Inverse Problem of Radioisotope Diagnosis: A Computational Method for Determining the Location and Size of Tumors", Mathematical Biosciences, 5:39–55 (1969).

Kuruc, et al., "An Improved deconvolution technique for improvement after suboptimal bolus injection", Radiol., 148:233–238 (1983).

Colin, et al., "Etude experimentale due renogramme", Arch. Kreisllauff., 16:289–306 (1965).

Bassingthwaighte, "Circulatory transport and the convolution integral", Mayo. Clin. Proc., 42:137–154 (1967).

Bacharach, et al., "Optimum Fourier filtering of cardiac data: a minimum-error method", J. Nucl. Med., 24:1176–1184 (1983).

Ham, et al., "Radionuclide quantitation of left-to-right cardiac shunts using deconvolution analysis: Concise communication", J. Nucl. Med., 22:688–692 (1981).

Stritzke et al., "Non invasive assessment of absolute renal blood flow (RBF) by temporal deconvolution using orthogonal polynomials", J. Nucl. Med., 29:862–863 (1988).

Alderson, et al., "Deconvolution Analysis in Radionuclide Quantitation of Left-to-Right Cardiac Shunts", J. Nucl. Med., 20:502–506 (1979).

Knop, et al., "Deconvolution Analysis of $^{99m}$Te-Methylene Diphosphonate Kinetics in Metabolic Bone Disease", Eur. J. Nucl. Med., 6:63–67 (1981).

Knop, et al., "Biokinetics of Bone Tracers by Means of Deconvolution Analysis-Comparison of $^{99m}$TcMDP, $^{99m}$TcDPD and $^{99m}$TcEHDP", Nucl.-Med., 21:144–145 (1982).

Stritzke, et al., "Funktionsszintigraphie: Eine einheitliche Methode zur Quantifizierung von Stoffwechsel und Funktion in Organen", Nucl.-Med., 24:211–221 (1985). (and accompanying English translation).

Meier, et al., "On the Theory of the Indicator-Dilution Method for Measurement of Blood Flow and Volume", J. App. Phys., 6:731–744 (1954).

FIG. 6

ORIGINAL IMAGES

.92 MIN  1.4  1.8  2.1

LINEAR RESPONSE

| .5 MIN | 1.6 | 4.8 | 6.9 |
| --- | --- | --- | --- |
| 9.1 | 11.2 | 13.3 | 16.5 |

METHOD AND APPARATUS FOR FORMING IMAGES USING ORTHOGONAL POLYNOMIALS FOR TEMPORAL DECONVOLUTION

BACKGROUND OF THE INVENTION

1. Technical Field

The invention relates generally to the application of an array processor for the processing of medical (scintigraphic) or other digitized time sequential images requiring deconvolution to extract a final result different and distinct from the original images, but related to information contained in the original images. Also, data having substantial Poisson noise content can be efficiently processed.

2. Background Art

The prior art teaches that extracting information from images by deconvolution is done by the transformation of the desired quantity (or image) by the use of the well known Fourier transform and subsequent arithmetic operations. The Fourier transform allows the change of an image from the spatial domain to the frequency domain, while the inverse Fourier allows transformation from the frequency domain back to the spatial domain again. In the frequency domain, the computation of deconvolution with another function also in the same frequency domain requires a simple arithmetic operation, whereas in the spatial domain the deconvolution operation would require multiple steps. Because of the added required steps in the spatial domain, deconvolution is highly inefficient as compared to deconvolution in the frequency domain, i.e. the same operation can be performed in the frequency domain more efficiently. This is why a tool that allows minimal operations to compute deconvolution is beneficial whenever a large number of images having multiple pixels need to be processed to extract information contained therein.

Furthermore, some images contain high amounts of noise that may render some Fourier based and other deconvolution methods ineffective. The present application describes a method that is highly tolerant of noise contained in images to be deconvolved.

SUMMARY OF THE INVENTION

Accordingly, in the medical context, the application of the temporal deconvolution method (DOP), described in this disclosure, is a method which can be used to isolate the response (blood flow) of a human organ (such as a kidney) from measurements (images) derived from other organs. The measurement of parameters (image acquisition) in other places on the body, e.g. the heart, to determine the response of the organ being studied is called the "input function". Upon operation on images making up the input function, by using the tool of temporal deconvolution, or the DOP method, the result is a linear response function (LRF). The LRF in this context describes the time activity curve that would result from the time sequence observation of a human organ or portion of an organ (pixel), and can be related to blood flow rates through said organ. The LRF thus is extracted from the combination of the input function along with other knowledge of the system and represents the characteristics of the system comprised of the organ under study (e.g. kidney) plus the other parts of the body being monitored (e.g. heart) to determine the operation of the subject organ (e.g. kidney). Accordingly, it is an object of the present invention to disclose a tool in the form of an array processor, or, in the alternative, a method, wherein, multi-pixel images containing digitized information can be deconvolved in conjunction with other information to extract information contained in multiple time related images or similar time sequential data.

For example, continuing in the medical field, specifically in the area of scintigraphic images, the kinetic information presented in, and obtained from, dynamic scintigraphic images is distorted because radioactive tracer uptake in an organ, such as a kidney, is a complex function dependent on the amount of tracer injected, the temporal course of blood activity, and diffusion and transport processes within the organ under study as well as in other organs. It is therefore an object of the present invention to extract information contained in such images acquired via scintigraphic techniques so as to reduce, or eliminate the interaction in such images of the various mechanisms of blood flow and tracer concentration changes. The method and apparatus shown herein will allow the evaluation of the amount of blood flow through the organ being studied free of the distractions and misinformation created by the concurrent interaction of simultaneous physical phenomena present in a normal functioning kidney.

As another example of the application of this invention, in the sonar field, images computed from data using returns derived from the reflection of sonic waves off various objects contain a high degree of noise and require the step of deconvolution for extraction of useful data, interpretation or final transformation into a human intelligible form. It is an object of the present invention to improve interpretation of such images by providing higher tolerance to the noise contained in such raw sonar data while simultaneously reducing the computation burden required to perform said deconvolution.

It is yet another object of the present invention to apply the teachings of the present invention to the field of radar where the interpretation of, for example, Synthetic Aperture Radar (SAR) images requires the deconvolution of image data polluted by data acquisition noise inherent in the processing of low signal to noise ratio radar returns. In this context, it is an object of present the invention to reduce effects created by the change in radar crossection of the target, scintillation, receiver noise, analog to digital converter noise etc. as well as reduce the computational load typically required for the deconvolution of such images.

It is yet another objective of the present invention to improve the interpretation of seismic data images used in oil exploration by providing computational means for reducing the effect of noise on said images and reduce the time required to compute the images generated from seismic, or other shock wave energy reflections or returns.

Generally, it is an object of this invention to improve the interpretation of information contained in time sequential data, such as time sequential images, or pulses, requiring the step of deconvolution in the presence of noise for final presentation in human readable form.

DESCRIPTION OF THE DRAWINGS

FIG. 6. Scintigraphic images from a dynamic radioactive iodine tracer study. The gray scale was adjusted in each image to encompass the same range of count rates. The images demonstrate the typical incorporation of the tracer by the thyroid.

FIG. 9. Depicts images of the LRF function. The gray scale was adjusted in each image to encompass a qualitative comparison of the images, which reflect increasing values at the first points, reach a maximum, decrease quickly, and then remain nearly constant (or decrease with a relatively small time constant).

DESCRIPTION OF THE PREFERRED EMBODIMENT

I. Historical perspective

Figure 1B:
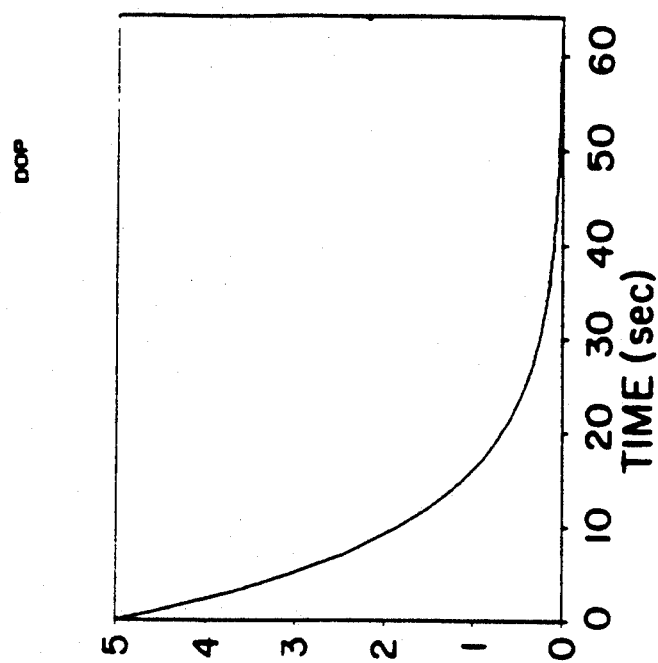
FIG. 1A. Time activity curves of the LRF and the blood input function. The output function was determined by numerical convolution of the input function with the LRF B-D: show the linear response functions (LRF's) calculated at "no noise" levels with various deconvolution tools so as to compare the results obtained in the prior art with the results obtained by the present method.

Because the application of the present invention is multifaceted, its details will be discussed with respect to the medical subject of scintigraphic images of human organs.

A number of different deconvolution techniques have proven useful for obtaining LRF's from clinical studies. Van Stekelenburg, "Hippuran transit times: A new approach", Phys. Med. Biol., 23:291-301 (1978); Van Stekelenburg et al., N. A. Kooman, "A Three-compartment model for the transport and distribution of hippuran", Phys. Med. Biol., 21:74-84 (1976); Diffey et al., "The $^{99m}$Tc DTPA dynamic renal scan with deconvolution analysis", J. Nucl. Med., 17:352-355 (1976); Alderson et al., "Deconvolution analysis in radionuclide quantitation of left to right cardiac shunts", J. Nucl. Med., 20:502-506 (1979); and Kuruc et al., "An improved deconvolution technique for improvement after suboptimal bolus injection", Radiol., 148:233-238 (1983). A recent article has reviewed these techniques, and described the methodological problems connected with the determination of the LRF. Szabo et al., "Model identification and estimation of organ-function parameters using radioactive tracers and the impulse-response function", Eur. J. Nucl. Med., 11:265-274 (1985). Because of the problem of noise in the data, most mathematical methods for temporal deconvolution have been successfully employed only with time activity curves from regions of interests (ROI) over whole or large portions of an organ. Knop et al. (1981) applied an analysis method using orthogonal polynomials. Knop et al., "Deconvolution analysis of $^{99m}$Tc-methylene diphosphonate kinetics in metabolic bone disease", Eur. J. Nucl. Med., 6:63-67 (1981). They applied this method to ROI data from patients with metabolic bone diseases to distinguish small differences in the kinetics of different bone tracers. Knop et al., "Biokinetics of bone tracers by means of deconvolution analysis-comparison of $^{99m}$Tc-MDP, $^{99m}$Tc-DPD, $^{99m}$Tc-EHDP", Nucl. Med., 21:145-149 (1982).

Unlike Stritzke et al., (1985), the present formulation of the DOP method described in this application does not require any specific model in terms of a deterministic description (or compartmental modeling) of the tracer kinetics. Stritzke et al., ("Funktionsszintigraphie: Eine einheitliche Methode zur Quantifizierung von Stoffwechsel und Funktion in Organen", Nucl. Med., 24:211-221 (1985). Furthermore, the present method can account for the contribution of the blood pool itself to the time activity curves obtained from clinical studies. The DOP technique described herein thus provides an alternative to the standard compartmental approach of analyzing dynamic scintigraphic data.

The present application solves postulated but unsolved problems related to deconvolution detailed in Stritzke et al., (1985). Unlike Stritzke et al., (1985), where merely a statement of the problem associated with deconvolution was stated, the present application provides a full understanding and complete derivation of the solution to the integral equation of a single pixel time activity curve using orthogonal polynomials. Previously, only approximative solutions, as described in Montz and Stritzke, "Schilddrüssen Funktions-bilder der 123-Jodid Clearance", NucCompact, 13:176-178 (1982), or a brief statement of the problem devoid of the details necessary to implement the solution were presented. Knopp et al., (1981); Knopp et al., (1982); and Stritzke et al., (1985).

It is the aim of this application to describe the method employed for full temporal deconvolution as well as the computation of results using an array processor. Array processors are widely available in nuclear medicine clinics for other "number-crunching" tasks. Their availability makes feasible the use of full temporal deconvolution on a pixel by pixel basis for image processing. FIG. 1 shows a comparison of the DOP method described herein with the Fourier transform method and the discrete deconvolution method for curves both with and without Poisson noise.

II. Theory

The Stochastic Approach of Tracer Theory

Assuming linearity and time invariance, as described in Meier and Zierler, "On the theory of the indicator-dilution method for measurement of blood flow and volume", J. Appl. Physiol., 6:731-744 (1954) and Zierler, "Theoretical basis of indicator dilution methods for measuring flow and volume", Circ. Res., 10:393-407 (1962), the organ activity A and activity in the blood B are related to the linear response function LRF (impulse response function) $h_L$ of the tissue being imaged by the convolution integral as described in Colin et al., "Étude expérimentale du rénogramme", Arch. Kreislauff., 16:289-306 (1965).

$$A(x,y,t) = \int_0^t h_L(x,y,t-t') \cdot B(t') \cdot dt' \quad (1)$$

It is assumed that A, B and $h_L$ are differentiable functions over the time period of the study T, with the exception that $h_L$ has a delta function partition which reflects the activity within the blood volume imaged as part of the pixel x,y. Thus, the linear response function (LRF) in equ.1 is given by Stritzke et al., (1985):

$$h_L(x,y,t) = h(x,y,t) + c(x,y) \cdot \delta(t) \quad (2)$$

where h is the "true" organ linear response function, c is the activity within the blood pool of the tissue being imaged, and δ is the Dirac delta function. The Dirac delta function in equ.2 represents a singularity, meaning that the linear response function reaches an infinite high function value at time zero. Standard deconvolution methods including the DOP method cannot handle singularities like this explicitly. Therefore, it is necessary to develop a form of equ.1 which can be deconvolved without the negative effects associated with this singularity. One way to accomplish this is to introduce the accumulative residence time distribution function $H_L$, as described in Bassingthwaighte, "Circulatory transport and the convolution integral", Mayo Clin. Proc., 42:137-154 (1967), which is defined as:

$$H_L(x,y,t) = \int_0^t h_L(x,y,t') \cdot dt'. \quad (3)$$

Substituting equ.2 into equ.3, one obtains:

$$H_L(x,y,t) = c(x,y) + \int_0^t h(x,y,t') \cdot dt' \quad (4)$$

where it is observed that the delta function δ has been integrated out. Now define the integral of the activity I as:

$$I(x,y,t) = \int_0^t A(x,y,t') \cdot dt'. \quad (5)$$

Using equ.1 and equ.3, equ.5 can be rewritten as:

$$I(x,y,t) = \int_0^t H_L(x,y,t-t') \cdot B(t') \cdot dt'. \quad (6)$$

Discrete Notation and Interpolation to Uniform Temporal Intervals

The DOP method, like any deconvolution analysis method, requires that a series of scintigraphic images be obtained concurrently with sampling of venous blood. The scintigrams need to be acquired with constant time intervals. If, however, images are not obtained at uniform time intervals, interpolation of data has to be employed. The same process can be applied to the results obtained from the venous blood samples.

In this disclosure, the sign (°) on a symbol indicates that the time sampling is not necessarily uniform. The dynamic study may consist of N images. For a given set of time points $0 \leq t_1^o \leq t_2^o \ldots \leq t_{p-1}^o \leq t_p^o \ldots \leq t_N^o = T$, the sampling of the scintigraphic images is defined as:

$$S^o(x,y, t_p^o) = \sum_{p=1}^{p} A(x,y,t') \cdot \Delta t' \quad (7)$$

where A is the activity in terms of counts per unit time in pixel x,y as determined by the gamma camera at time $t_p^o$ post-injection. Any number of venous blood samples $B^o$ can be taken at times $t_i^o$ over the time period T of the study, but more than one sample will improve confidence in the result. The units of the samples $B^o$ are in activity per unit time measured in a well counter.

With discrete sampling, the equation giving the integral of the activity (equ.6) can be written as:

$$I^o(x,y, t_n^o) = \sum_{m=1}^{n} S^o(x,y, t_m^o) \cdot \Delta t \quad (8)$$

where $S^o$ is the pixel count in the scintigram as defined in equ.7. The expansion of $I^o$ and $B^o$ using orthogonal polynomials which is used to deconvolve equ.6 requires equal time sampling. If necessary, linear interpolation is used to convert $I^o$ and $B^o$ to I and B sampled over U time points $t_n$ defined as $$t_n = (n-1) \cdot \Delta t, \; n=1,2,\ldots, U \quad (9)$$

with $\Delta t = T/(U-1)$ and $U \cdot t \leq T$. The linear interpolation of the sampled integral images $I^o$ into the uniformly time sampled integral images I can be conducted in the following way. First, a set of interpolation coefficients are calculated for each time point $t_n$ with $t_1 \leq t_2 \ldots \leq t_n \leq T$:

$$\alpha_n = (t_n^o - t_n) \cdot D_n^o$$
$$\beta_n = 1 + t_n \cdot D_n^o - t_n^o \cdot D_n^o \quad (10)$$

where:

$$D_n^o = \frac{1}{t_{n+1}^o - t_n^o} \text{ for } t_n^o \leq t_n \leq t_{n+1}^o. \quad (11)$$

This is performed in the host computer. Then, the interpolation of the integral images is performed in the array processor as $$I(x,y,t_n) = \text{En} \cdot I^o(x,y,t_N^o) \beta_n \cdot I^o(x,y,t_n^o). \quad (12)$$

Using linear interpolation or cubic spline interpolation, as described in Späth, *Spline-Algorithmen zur Konstruktion glatter Kurven und Flachen.* R. Oldenburg Verlag München, Wien (1978) and Press et al., *Numerical Recipes, The Art of Scientific Computing,* Cambridge University Press, Cambridge, N.Y. (1986), for the input function $B^o$, and replacing the integral with its approximation by a Riemann sum, equ.6 can be written as:

$$I(x,y,t_i) = \sum_{m=1}^{i} H_L(x,y,t_i - t_m) \cdot B(t_m) \cdot \Delta t. \quad (13)$$

Equ.13 is the final stochastic description of the tracer behavior in an organ and is independent of specific compartmental models. It is temporally deconvoluted to yield the integral of the response function $H_L$. Given $H_L$, h is derived by numerical differentiation.

Function Analytical Solution of the Convolution Type Integral Equation

With the assumption of square integrability of the functions $H_L$, B and I in the time interval $0 \leq t \leq T$ during the investigation, equ.13 can be written in the Dirac notation $$|I> = |B|H_L>. \quad (14)$$

The desired function $|H_L>$ is connected to the known (measured) function $|I>$ by the operator $|B|$. The method of inversion of equ.14 (deconvolution) which is used herein requires the introduction of a set of orthonormal polynomials $p_k(t)$, e.g. Legendre Polynomials, as described in Arfken, *Mathematical Methods for Physicists,* Academic Press, New York and London (1968), calculated from their recurrence relation (Rodrigues' formula):

$$(k+1) \cdot p_{k+1} + k \cdot p_{k-1} = (2 \cdot k+1) \cdot t \cdot p_k |t| \leq 1 \quad (15a)$$

The $p_k(t)$ are normalized by setting $p_k(1)=1$. In particular the first five functions can be written:

$$p_0(t) = 1$$
$$p_1(t) = t$$
$$p_2(t) = (3 \cdot t^2 - 1)/2$$
$$p_3(t) = (5 \cdot t^3 - 3 \cdot t)/2$$
$$p_4(t) = (35 \cdot t^4 - 30 \cdot t^2 + 3)/8$$
$$p_5(t) = (63 \cdot t^5 - 70 \cdot t^3 + 15 \cdot t))/8 \quad (15b)$$

The $p_k(t)$ are orthogonal in the interval $1 \leq t \leq 1$ with the orthogonality-completeness relation $<p_m|p_n> = \delta_{mn} \cdot 2/(2n+1)$, where $\delta_{mn}$ is called the Kronecker delta and is defined by $\delta_{mn}=0$ for $n \neq m$, $\delta_{mn}=1$ for $n=m$. The polynomials $|p_k>$ are combined with B to produce the adjoint operator $|B|^+$ according to equ.A.8, $$|b_k> = |B|^+ p_k>, \; k=0,1,2,\ldots, Z \quad (16a)$$

In approximating the integral in equ.16 by a Riemann sum, $|b_k>$ can be written $$b_k(t_n) = \sum_{m=1}^{U-n} B(t_m) \cdot p_k(t_m + t_n) \cdot \Delta t \quad (16b)$$

where $n=1,2,\ldots,$ U corresponds to the time points $t_n$ (the time points including $\Delta t$ are transformed into the interval $[-1,1]$) of the interpolated scintigraphic study). The $|b_k>$ are linearly independent but not necessarily orthogonal. From a set of linearly independent functions such as $|b_k>$ an orthonormal set of function $|c_m>$ over $[-1,1]$ can be constructed by simple linear combination of the $|b_k>$, such that $<c_i|c_j> = \delta_{ij}$, $i,j=0,1,2,\ldots,$ Z. In order to calculate the coefficients of the new linear combination $|c_k>$, the classical Gram-Schmidt method, as described in Zurmüh, *Praktische Mathematik fur Ingenieure und Physiker.* Springer, Berlin, N.Y. (1965) and Delves and Mohamed, *Computational Methods for Integral Equations,* Cambridge University Press, Cambridge, London, N.Y. (1985), was modified by starting with the following set of equations:

$$|c_1> = |b_1> \quad (17a)$$
$$|c_2> = a_{21} \cdot |c_1> + |b_2> \quad (17b)$$
$$|c_3> = a_{31} \cdot |c_1> + a_{32} \cdot |c_2> + |b_3> \quad (17c)$$
$$|c_4> = a_{41} \cdot |c_1> + a_{42} \cdot |c_2> + a_{43} \cdot |c_3> + |b_4> \quad (17d)$$

The coefficients $a_{mi}$, $m=2 \ldots Z$, $i=1 \ldots m-1$ can be calculated by forming suitable scalar products $<c_i, |c_j>$ from each line in equ.17. Forming the scalar product $<b_1|c_2>$ in equ.17b yields $$<b_1|c_2> = 0 = a_{21} \cdot <b_1|c_1> + <b_1|b_2>$$

$$a_{21} = -<b_1|b_2> \tag{18b}$$

and forming the scalar products $<c_1|c_3>$ and $<c_2|C_3>$ in equ.17c yields $$<c_1|c_3> = 0 = a_{31} \cdot <c_1|c_1> + a_{32} \cdot <b_1|c_2> + <c_1|b_3>$$

$$<c_2|c_3> = 0 = a_{31} \cdot <c_2|c_1> + a_{32} \cdot b_2|c_2> + <c_2|b_3>$$

$$a_{31} = -<b_1|b_3> \tag{18c}$$

$$a_{32} = -<b_2|b_3>$$

For equ.17d one obtains $$<c_1|c_4> = 0 = \tag{18d}$$

$$a_{41} \cdot <c_1|c_1> + a_{42} \cdot <c_1|c_2> + a_{43} \cdot <c_1|c_3> + <c_1|b_4>$$

$$<c_2|c_4> = 0 =$$

$$a_{41} \cdot <c_2|c_1> + a_{42} \cdot <c_2|c_2> + a_{43} \cdot <c_2|c_3> + <c_2|b_4>$$

$$<c_3|c_4> = 0 =$$

$$a_{41} \cdot <c_3|c_1> + a_{42} \cdot <c_3|c_2> + a_{43} \cdot <c_3|c_3> + <c_3|b_4>$$

$$a_{41} = -<c_1|b_4>$$
$$a_{42} = -<c_2|b_4>$$
$$a_{43} = -<c_3|b_4>$$

and generally:

$$a(m,j) = -<c_j|b_m>, \; m = 1 \ldots Z, \; j = 1 \ldots m-1. \tag{18e}$$

In order to form an orthonormal set of functions $|c_m>$, the $a_{mi}$ (equ.18e) must be divided by their norm factors. With these factors a new set of coefficients is calculated by $$a_{1,1} = <b_1|b_1>^{-\frac{1}{2}} = \left( \int_{-1}^{1} b_1(t') \cdot b_1(t') \cdot dt' \right)^{-\frac{1}{2}} \tag{19b}$$

where $||b_1|| = <b_1|b_1>$ denotes the norm.

$$a_{m,j} = \frac{a_{m,j}}{\left( <b_m|b_m> - \sum_{i=1}^{j} a_{mi}^2 \right)^{\frac{1}{2}}} \tag{19b}$$

$$j = 1, 2, \ldots, m-1$$
$$m = 2, 2, \ldots, Z$$

$$a_{m,m} = \frac{1}{\left( <b_m|b_m> - \sum_{i=1}^{m-1} a_{mi}^2 \right)^{\frac{1}{2}}}, \tag{19c}$$

$$m = 2, 2, \ldots, Z$$

Hence, the set of equ.17 can now be rewritten:

$$|c_1> = a_{11} \cdot |b_1> \tag{20a}$$
$$|c_2> = a_{21} \cdot |c_1> + a_{22} \cdot |b_2> \tag{20b}$$
$$|c_3> = a_{31} \cdot |c_1> + a_{32} \cdot |c_2> + a_{33} \cdot |b_3> \tag{20c}$$
$$|c_4> = a_{41} \cdot |c_1> + a_{42} \cdot |c_2> + a_{43} \cdot |c_3> + a_{44} \cdot |b_4> \tag{20d}$$

This function set can easily be rearranged to $$|c_1> = \tau_{11} \cdot |b_1> \tag{21a}$$
$$|c_2> = \tau_{21} \cdot |b_1> + \tau_{22} \cdot |b_2> \tag{21b}$$
$$|c_3> = \tau_{31} \cdot |b_1> + \tau_{32} \cdot |b_2> + \tau_{33} \cdot |b_3> \tag{21c}$$
$$|c_4> = \tau_{41} \cdot |b_1> + \tau_{42} \cdot |b_2> + \tau_{43} \cdot |b_3> + \tau_{44} \cdot 0|b_4> \tag{21d}$$

or $$|c_m> = \sum_{i=1}^{m} \tau_{mi} \cdot |b_i>, \; m = 1, 2, \ldots, Z \tag{22}$$

where the $\tau_{mi}$ are given by:

$$\tau_{11} = a_{11} \tag{23}$$
$$\tau_{21} = a_{21} \cdot a_{11}$$
$$\tau_{22} = a_{22}$$
$$\tau_{31} = a_{31} \cdot a_{11} + a_{32} \cdot a_{21} \cdot a_{11}$$
$$\tau_{32} = a_{32} \cdot a_{21}$$
$$\tau_{33} = a_{33}$$
$$\tau_{41} = a_{41} \cdot a_{11} + a_{42} \cdot a_{21} \cdot a_{11} + a_{43} \cdot a_{31} \cdot a_{11} + a_{43} \cdot a_{32} \cdot a_{21} \cdot a_{11}$$
$$\tau_{42} = a_{42} \cdot a_{22} + a_{43} \cdot a_{32} \cdot a_{22}$$
$$\tau_{43} = a_{43} \cdot a_{33}$$
$$\tau_{44} = a_{44}$$

It should be noted that an orthogonal function system, if multiplied by an arbitrary constant $k \neq 0$, remains an orthogonal function system. Thus, the coefficients $\tau_{mi}$ calculated from equ.23 can be used to construct a second set of functions using the Legendre polynomials calculated in equ.15

$$|d_m> = \sum_{i=1}^{m} \tau_{mi} \cdot |p_i> \tag{24a}$$

or equivalently $$d_m(t) = \sum_{i=1}^{m} \tau_{mi} \cdot p_i(t) \tag{24b}$$

which is also an orthogonal function system. The $|c_m>$ and $|d_m>$ are now being used to invert the integral equ.14. For this purpose start with the completeness or closure condition as described in Liboff, *Introductory Quantum Mechanics*. Holden-Day, California (1980)

$$\sum_{m=1}^{Z} |c_m><c_m| = 1 \tag{25}$$

(note that $|c_m><c_m|$ is an operator). Now it can be written $|H_L>$ as the identity $$|H_L> = \sum_{m=1}^{Z} |c_m><c_m|H_L>. \tag{26}$$

With insertion of equ.22 into equ.26, it is found $$|H_L\rangle = \sum_{m=1}^{Z} |c_m\rangle \cdot \sum_{n=1}^{m} \tau_{mn} \langle b_n|H_L\rangle. \quad (27)$$

With equ.16 follows $$|H_L\rangle = \sum_{m=1}^{Z} |c_m\rangle \cdot \sum_{n=1}^{m} \tau_{mn} \langle p_n|B|H_L\rangle \quad (28)$$

and using equ.24 and equ.14 the final result is $$|H_L\rangle = \sum_{m=1}^{Z} |c_m\rangle \langle d_m|I\rangle. \quad (29)$$

The expression for accumulative residence time distribution function $|H_L\rangle$ can be written for computer implementation in the final form $$H_L(x, y, t_n) = \sum_{m=1}^{Z} c_m(t_n) \cdot \left( \sum_{n=1}^{U} d_m(t_n) \cdot I(x, y, t_n) \cdot \Delta t \right) \quad (30)$$

The LRF can be calculated by numerical differentiation of equ.24

$$h(x, y, t) = \frac{\partial H_L(x, y, t)}{\partial T}$$

using following five point formula as described in Hildebrand, *Introduction to Numerical Analysis*, McGraw-Hill, New York (1974)

$$H_0' = \frac{1}{10 \cdot \Delta t}(-2 \cdot H_{-2} - H_{-1} + H_1 + 2 \cdot H_2). \quad (31)$$

According to the definitions given in equ.3 and equ.4 the partition blood volume can be determined by $$c(x,y) = H(x,y,t=0) \quad (32)$$

III. Implementation

Computer implementation of the DOP method is carried out by the following step-by-step procedure.

1. Calculate the functions $|C_m\rangle$ according to equ.1-5-23 where the $|c_m\rangle$ represent a Z·U matrix, Z denotes the number of polynomials, and U the number of images:

$$\begin{matrix} c_1(t_1) & c_1(t_2) & c_1(t_3) & \ldots & c_1(t_U) \\ c_2(t_1) & c_2(t_2) & c_2(t_3) & \ldots & c_2(t_U) \\ c_3(t_1) & c_3(t_2) & \ldots & & \\ \cdot & \cdot & & & \\ \cdot & \cdot & & & \\ \cdot & \cdot & & & \\ c_Z(t_1) & c_Z(t_2) & c_Z(t_3) & \ldots & c_Z(t_U) \end{matrix} \quad (33)$$

2. Calculate the orthogonal set of functions $|d_m\rangle$ according to equ.24 with $$\begin{matrix} d_1(t_1) & d_1(t_2) & d_1(t_3) & \ldots & d_1(t_U) \\ d_2(t_1) & d_2(t_2) & d_2(t_3) & \ldots & d_2(t_U) \\ d_3(t_1) & d_3(t_2) & \ldots & & \\ \cdot & \cdot & & & \\ \cdot & \cdot & & & \\ \cdot & \cdot & & & \\ d_Z(t_1) & d_Z(t_2) & d_Z(t_3) & \ldots & d_Z(t_U) \end{matrix} \quad (34)$$

3. If the scintigraphic images are not recorded at uniform time intervals, integrate and interpolate the scintigrams according to equ.8-2.

4. Calculate a new set of values $|f_m\rangle$ representing the second sum term in equ.29:

$$f_1(x, y) = \sum_{i=1}^{U} d_1(t_i) \cdot I(x, y) \quad (35)$$

$$f_2(x, y) = \sum_{i=1}^{U} d_2(t_i) \cdot I(x, y)$$

$$f_Z(x, y) = \sum_{i=1}^{U} d_Z(t_i) \cdot I(x, y).$$

5. Calculate equ.29 in the form:

$$H(x, y, t_i) = \sum_{m=1}^{Z} c_m(t_i) \cdot f_m(x, y). \quad (36)$$

6. Finally calculate the linear response function h by numerical differentiation according to equ.31.

In steps 1 and 2, no image data is required. The elements of $|c_m\rangle$ and $|d_m\rangle$ are only dependent on the input function and the type of polynomials. The computation can be performed in the host computer within a few seconds. Use of an array processor can speed this phase of the implementation, but this is not the major computational load of the method. Steps 3, 4 and 5 require access to the entire image set of 50-150 images. In the mini-computers, typically used in nuclear medicine, it is usually not possible to have all of these images resident in memory at one time. To avoid multiple disk transfers of the data set, it has been suggested to depict a subset of the image data (e.g. 1/16 of each image) for complete data processing through steps 3-6 which are the number "crunching" intensive portion of the method. To test out the concept of the invention, these have been implemented on an array processor (Analogic, AP 400).

IV. Results

Comparison of DOP with other Deconvolution Methods

Time activity curves were computer simulated in order to compare DOP with the Fourier deconvolution, and discrete deconvolution or the matrix method. Let $\Delta t$ denote the time interval between consecutive time samples, so that the sequence of calculated values is $$B_n = B(n \cdot \Delta t), n = 0,1,2,3, \ldots, N$$

$$h_n = h(n \cdot \Delta t) = h(t) \quad (37)$$

For simplicity, N was set to 64. The input function $B_n$ and the linear response function h were computed as $B_n = t_n \cdot a \cdot exp(-b \cdot t_n)$ with $a=10.0$, $b=0.25$
(arbitrarily)

$h(t_n) = c \cdot exp(-d \cdot t_n)$ with $c=0.25$, $d=0.1$ (38)

Figure 1A:
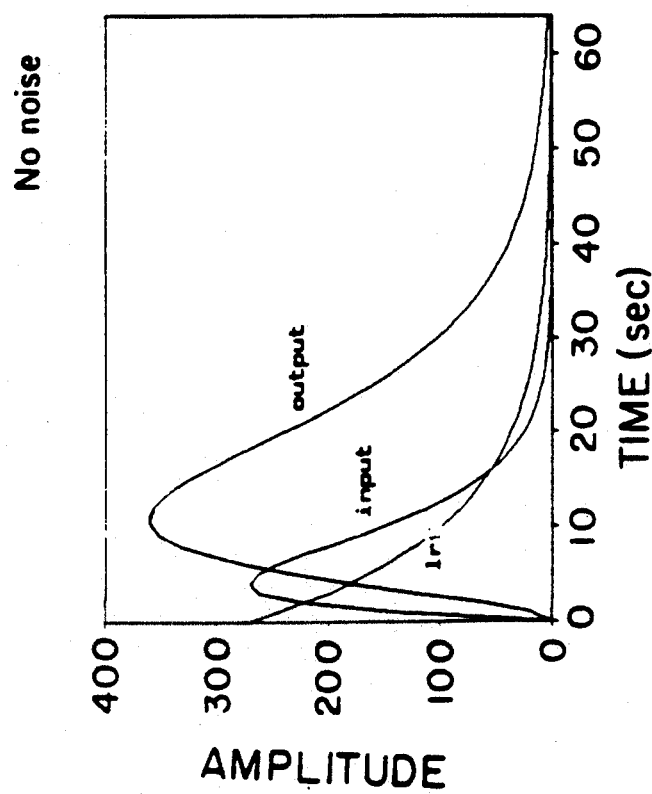
Figure 1D:
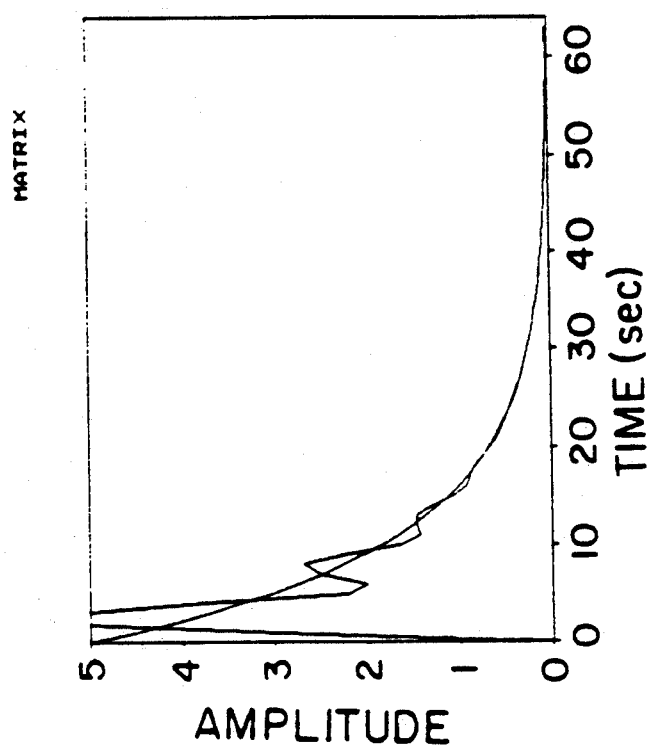
Figure 1C:
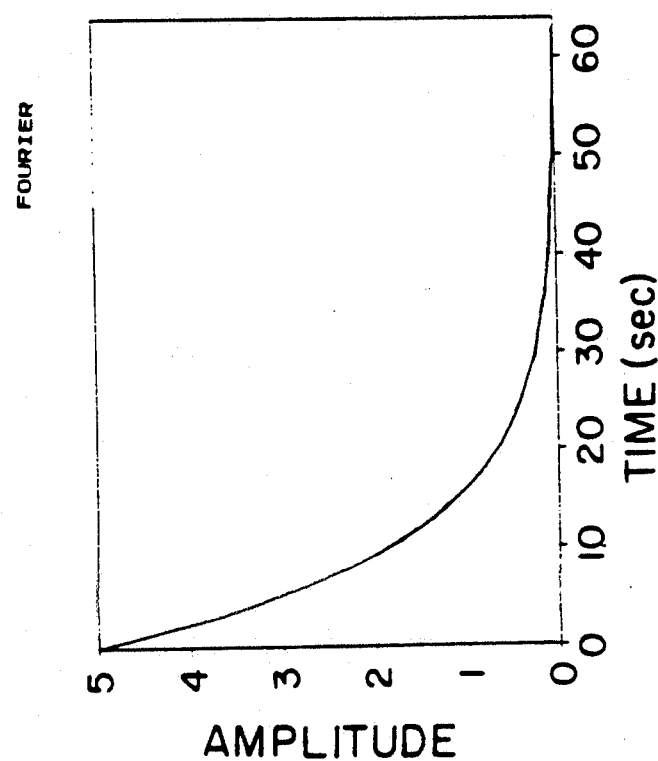

The output function $A(t_n)$ was calculated by numerical convolution of $B_n$ with $h(t_n)$ (FIG. 1A). Because the Fourier method as well as the discrete deconvolution method do not handle implicitly the presence of blood volume (delta functional partition in the linear response function), the contribution of blood volume (c) in equ.2 was set to zero in all calculations. Consequently, the LRF $|h>$ can be calculated immediately by retaining the output function $|A>$ instead of calculating its integral $|I>$.

Figure 2B:
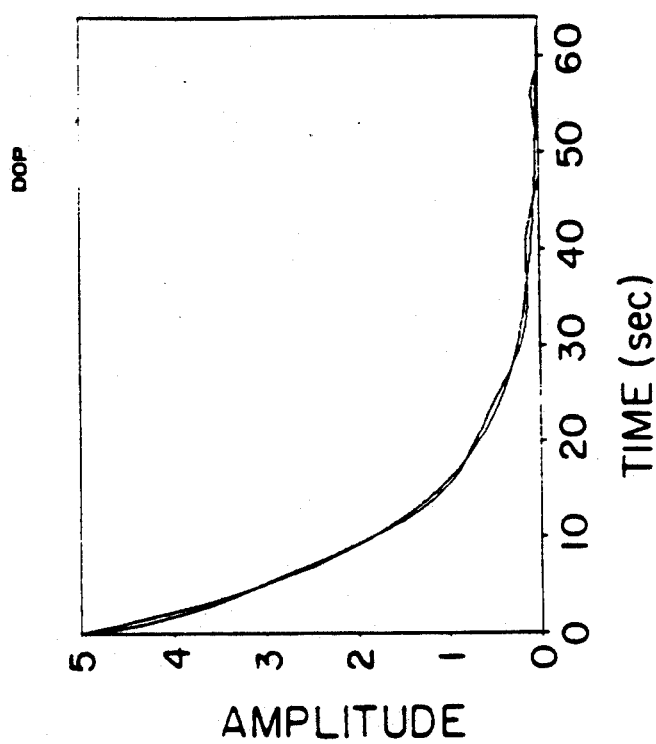
FIG. 2. Linear response functions calculated at a noise level of 1,000 counts. A: Time activity curves of the LRF, the input function I and organ output function O. Noise was added to the input function I and organ output function O. B-D: LRF calculated by the DOP method to compare with results obtained in the prior art.
Figure 2A:
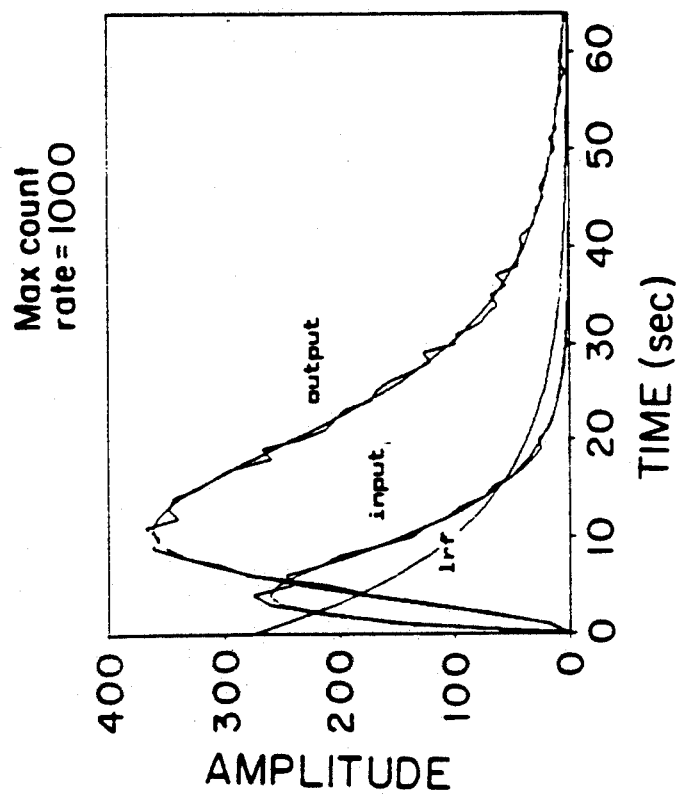
Figure 2D:
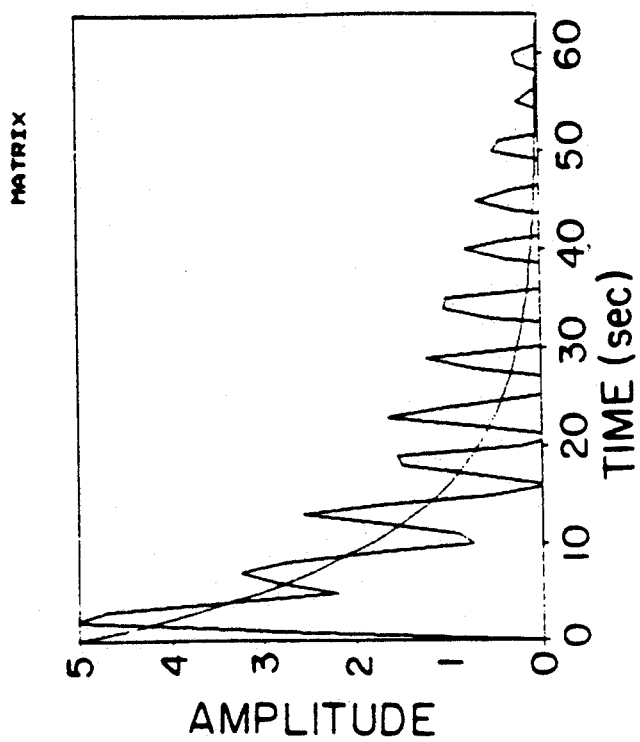
Figure 2C:
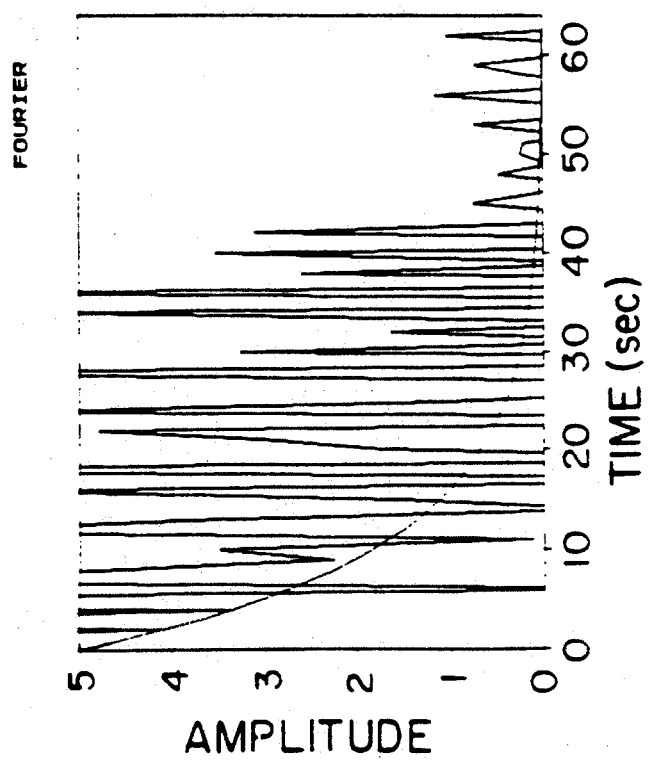
Figure 3A:
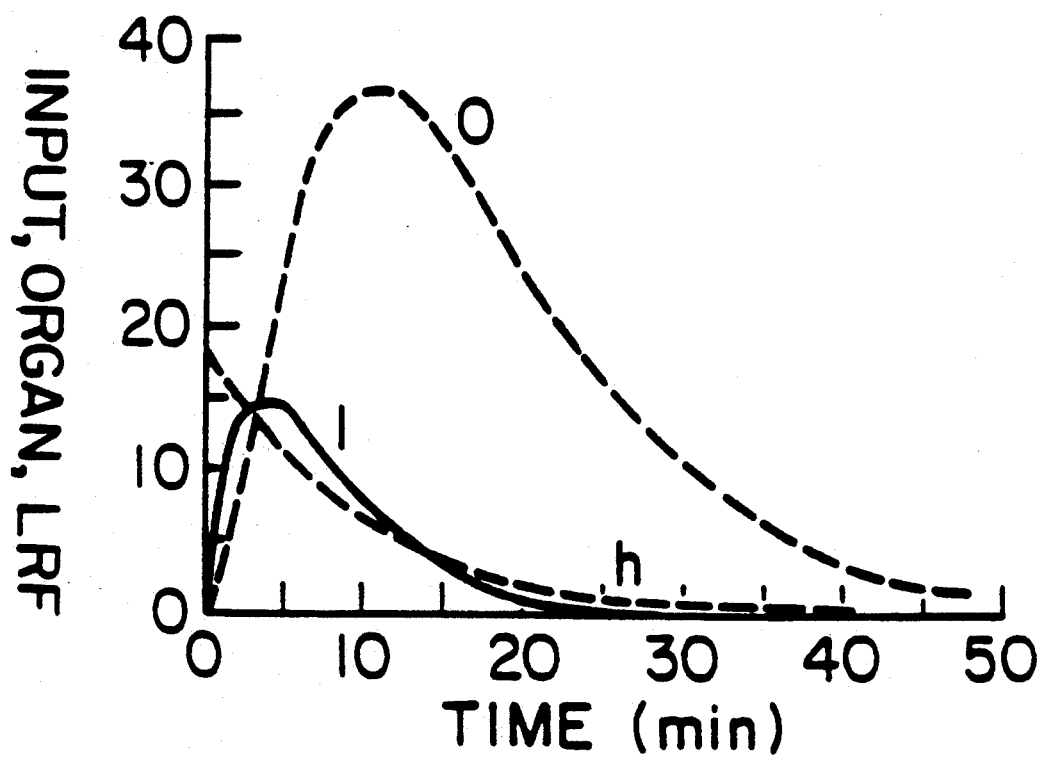
FIG. 3. Computer simulated curves for the linear response function h, the blood input function I, and the organ output function O. A: no noise added, B: noise added only to the organ output function.
Figure 3B:
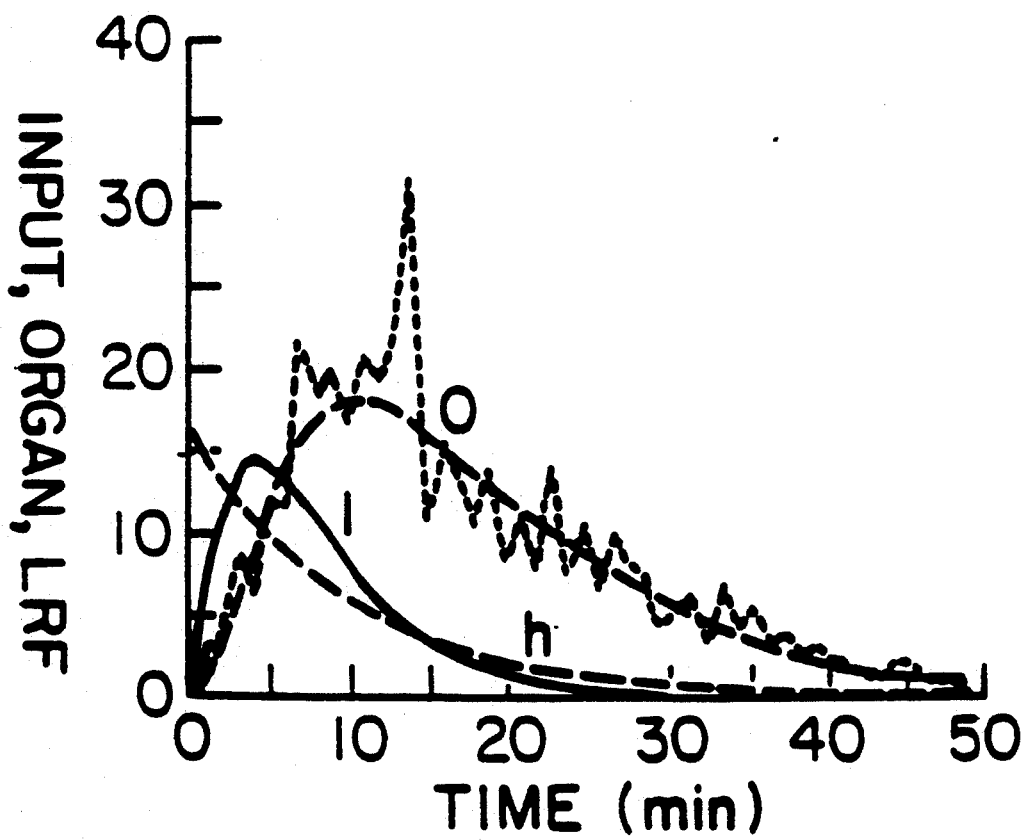

FIG. 1 shows the results of applying the DOP, the Fourier and the discrete deconvolution method in calculating the linear response function from the input and the output curves. Deconvolution by the DOP method (FIG. 1B) and the Fourier method (FIG. 1C) reproduced the LRF exactly. When the LRF was derived with the discrete deconvolution method, an oscillating curve, which is especially distorted in the first half, was obtained (FIG. 1D). To compare the effect of noise on each of these methods, count-dependent Poisson noise was added to the data points of the input and output curves before deconvolution (FIGS. 2A, 3A, 4A). The input and output curves were scaled to produce count rates of 1000 counts in their peak values. For each data point, a random number generator was used to select a value from a Poisson distribution having a mean value equal to the original value stored in each data point. Lo, Ph.D. Thesis, University of Southern California (1979). These curves were then deconvolved by different deconvolution methods (FIGS. 2-4, B-D). The LRF calculated with the DOP method performed much better at all noise levels than the LRFs calculated with Fourier- and discrete-deconvoluton methods. It is significant that very small amounts of noise at 50,000 counts distorted the LRFs calculated by the Fourier method. In general, the DOP mechanism was superior to the other methods in that it demonstrated the smallest systematic and statistical errors over the range of noise levels tested.

The Degree of Orthogonal Polynomials (Z) and Partition Blood Volume (c)

The calculation of the LRF (or its integral) according to equ.30 requires the finite summation $m = 1 \ldots Z$ of orthogonal functions $|d_m>$ and $|c_m>$. The number of polynomial (Z) used determines the performance of the resulting LRF. This approach is analogous to the problem of Fourier analysis of multi-gated cardiac studies. The question is how many Fourier harmonics are needed to fit the time activity curve and yet smooth noise. Bacharach et al. (1985), "Optimum Fourier filtering of cardiac data: a minimum-error method", J. Nucl. Med., 24:1176-1184 (1983). King et al. proposed a nonstationary temporal Wiener filter to produce an "optimal" suppression of noise in pixel time activity curves. King and Miller, "Use of nonstationary temporal Wiener filter in nuclear medicine", Eur. J. Nucl. Med., 10:458-461 (1985). In order to investigate a similar "multi-harmonic" effect with the DOP method, a computer-simulated blood input and organ output curves as well as the organ linear response functions using the same parameters as given in equ.38. were computed. FIGS. 3A and B shows the curves for the case of no added Poisson noise and FIG. 3B shows the curves when Poisson noise is added in sets of 50 data points each. FIGS. 4A, C, E show the computer simulated LRFs overlaid by the LRFs calculated by the DOP method for the data in FIG. 3A (no-noise). The parameter varied was the number of polynomials which ranged from 5 to 20. In all three calculations the blood volume partition was set to zero. The method of computation converged quickly and there was practically no difference between simulated and calculated LRF. In the absence of noise, the quality of the calculated LRF is independent of the degree of polynomials (Z=5-20). The performance of the DOP method changes slightly when a partition blood volume $c \cdot B(t)$ (blood background) was added to the output function $A(t)$. The partition blood volume $c(x,y) \cdot B(t)$ is the amount of radioactivity contributed by the blood in tissues surrounding the organ or tissue of interest. The total activity measured by the gamma camera at the time t in the pixel x,y is $A(x,y,t) + c(x,y) \cdot B(t)$. When in vivo measurements are made, c must be $0 < c < 1$. To demonstrate the impact of this contribution, we discussed the extreme situations, $c=0$, which means that there is no contribution from extraneous tissue activity, and $c=0.5$, which we think is, from the biologic point of view, the worst case situation or nearly so.

Figure 4B:
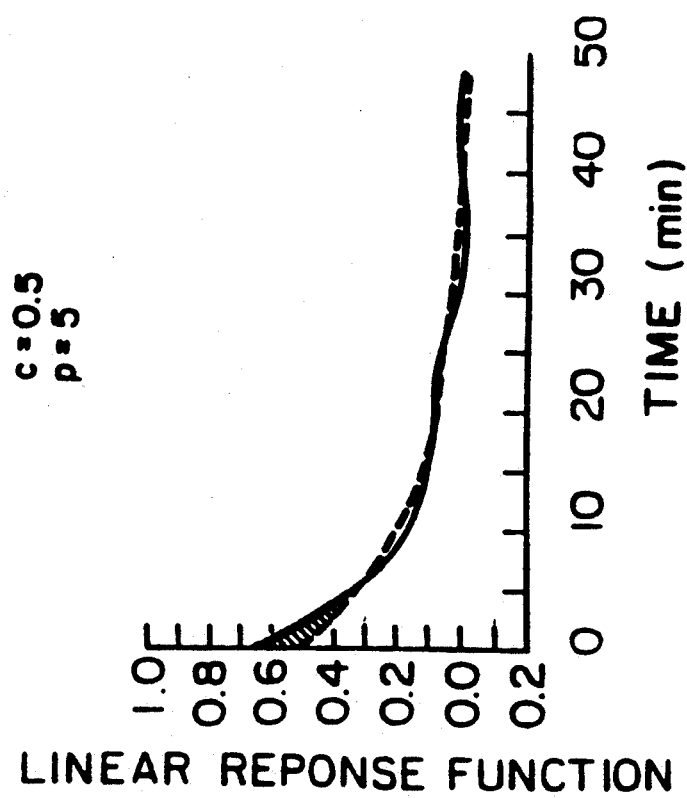
FIG. 4. Linear response functions calculated by the DOP method. Input and output functions did not contain noise components (FIG. 3A). Left side of FIGS. 4A, C, E: partition blood volume was set to zero. The parameter p=5,10,20 denotes the number of polynomials used. The DOP algorithm converged quickly and remained also stable when high numbers of polynomials were used. Right side of FIGS. B, D, F: partition blood volume (or background) c*B(t) was added to the organ output function O(t) before deconvolution. The new organ output function was calculated by O'(t)=O(t)+0.5*B(t). The DOP method needed almost 15-20 polynomials to reconstruct the theoretically expected delta-functional partition c*δ(t) in the linear response function and an error free organ linear response function.
Figure 4A:
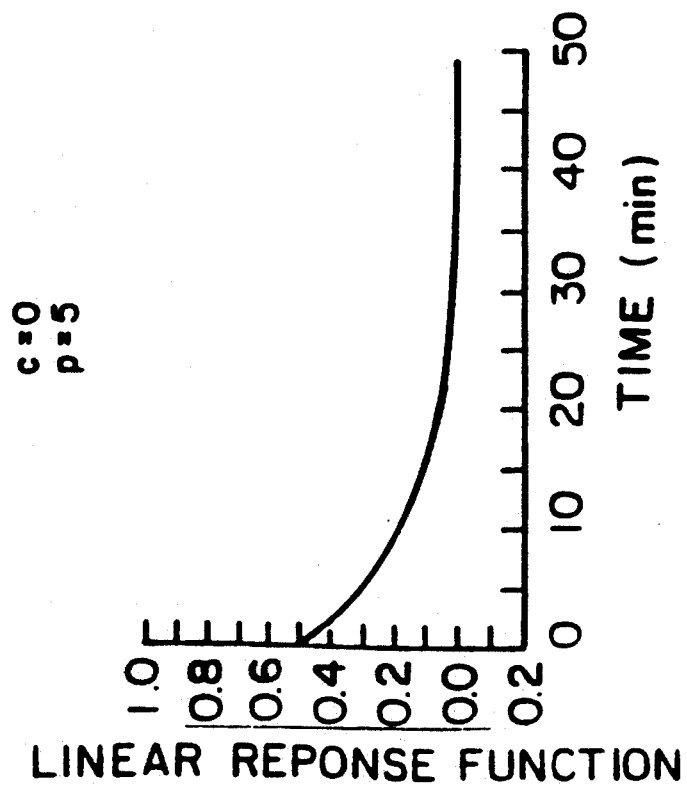
Figure 4D:
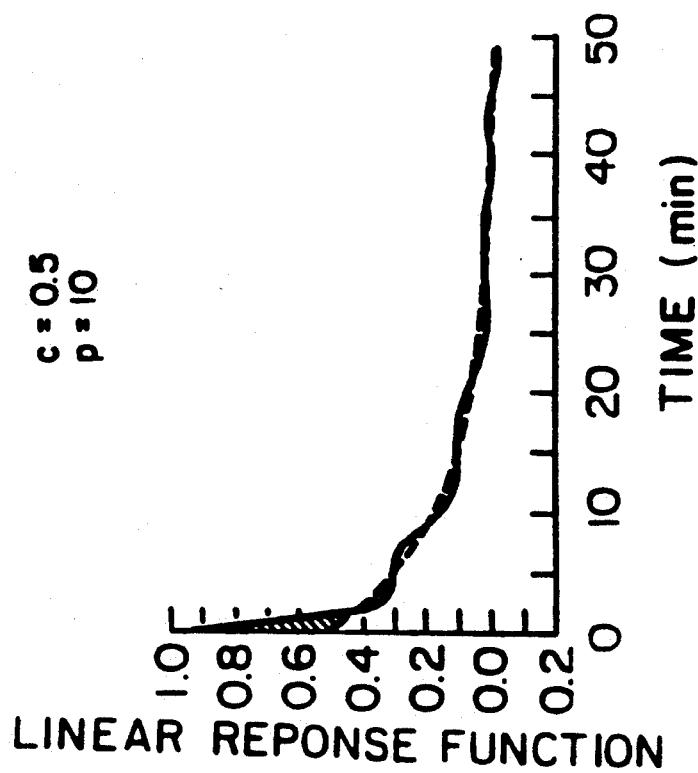
Figure 4C:
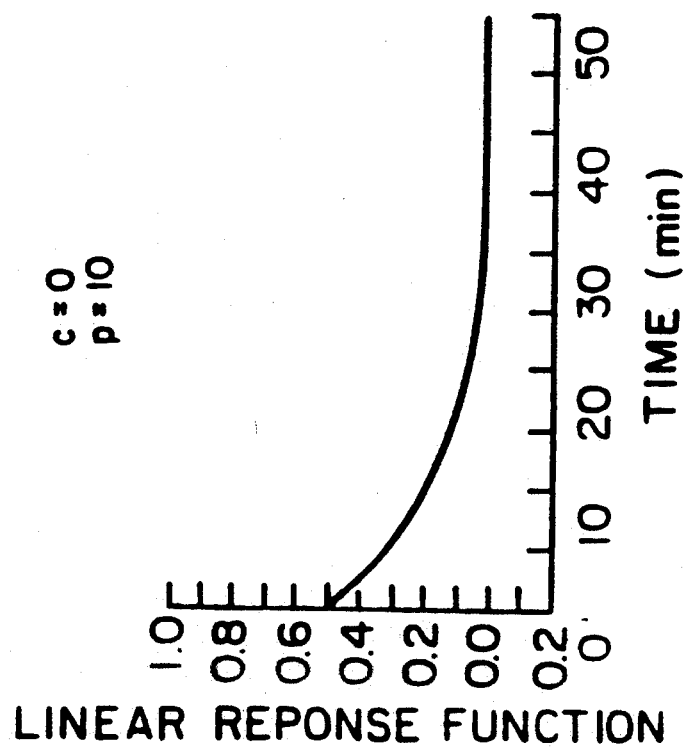
Figure 4F:
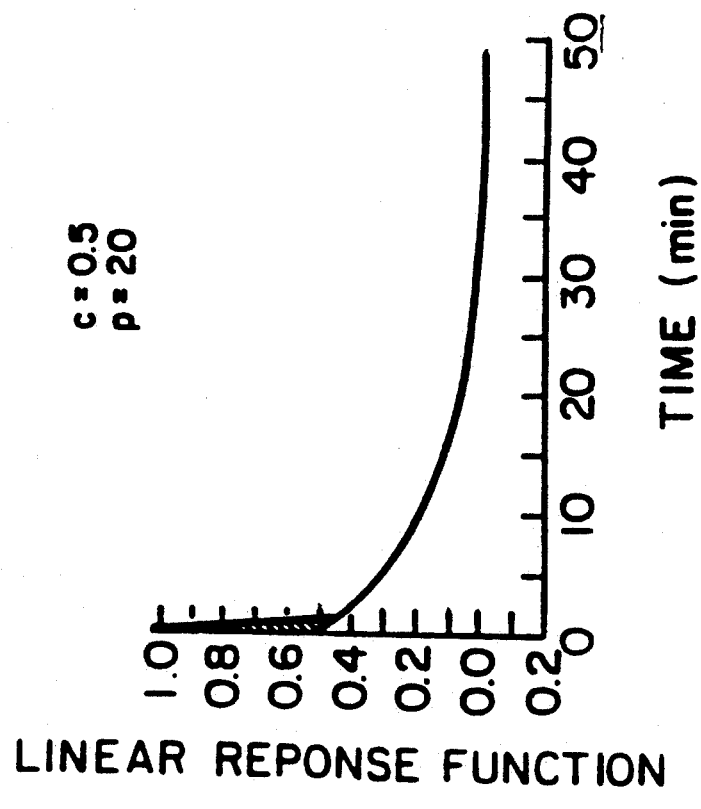
Figure 4E:
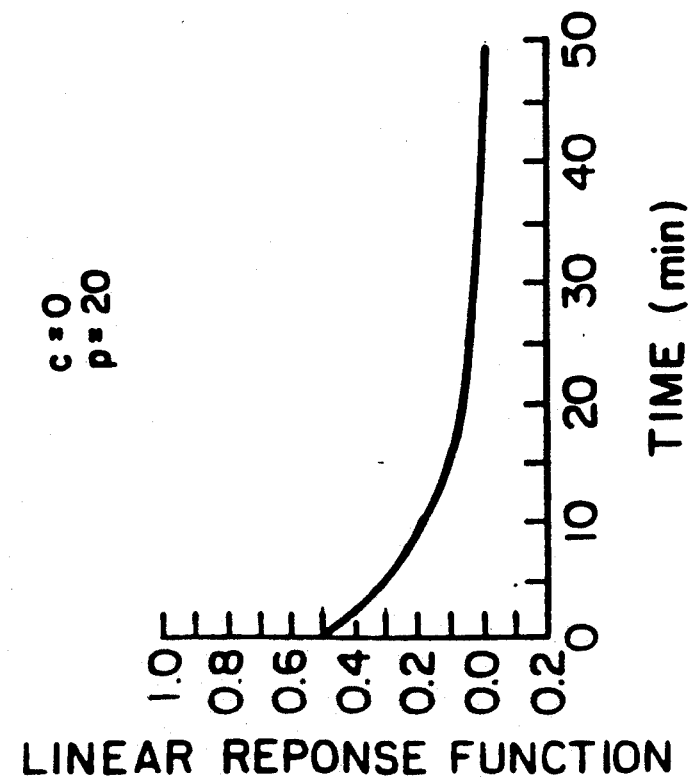

FIGS. 4B, D, F show the resulting LRFs obtained after having added blood background. Parameter was again the number of polynomials (Z). The DOP method now converged much slower than in the absence of blood background. In order to obtain a perfect reproduction of the calculated LRF, at least 15-20 polynomials were necessary. It should be noted that the delta functional partition $c \cdot \delta(t)$ represented by the dashed area in FIGS. 4B, D, F resulted from the deconvolution process, and did not distort the time course of the LRF. The curve in FIG. 4F can be interpreted as the sum of the "true" organ response $h(t)$ and a delta functional partition $c \cdot \delta(t)$ (see also equ.2).

Figure 5B:
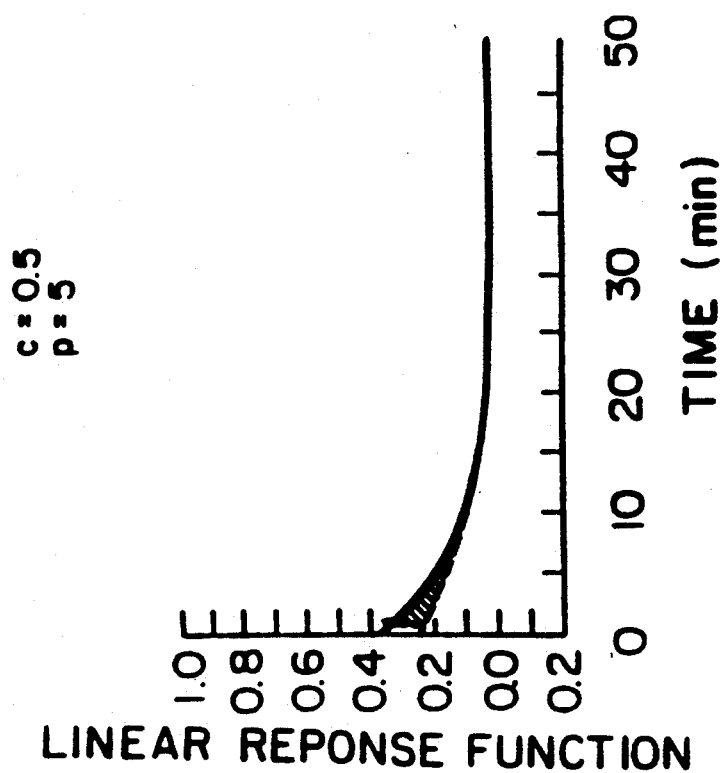
FIG. 5. Linear response functions calculated by the DOP method. Noise was added to the output function (FIG. 3B). Left side of FIG. A, C, E: partition blood volume was set to zero. The parameter p=5,10,20 denotes the number of polynomials used. There is an "optimal" number of polynomials (typically Z=15) which reconstructs an oscillating but systematic error free LRF. Higher numbers of polynomials increase the amplitudes of inherent oscillations. Right side of FIGS. B, D, F: partition blood volume (or background) c*B(t) was added to the organ output function O(t) before deconvolution. The new organ output function was calculated by O'(t)=O(t)+0.5*B(t). The DOP method needed almost 10 polynomials to reconstruct an oscillating but systematic error free organ linear response function which is superimposed by the theoretically expected delta-functional partition c*δ(t). Increase of the number polynomials distorted both, the organ linear response and the partition blood volume value.
Figure 5A:
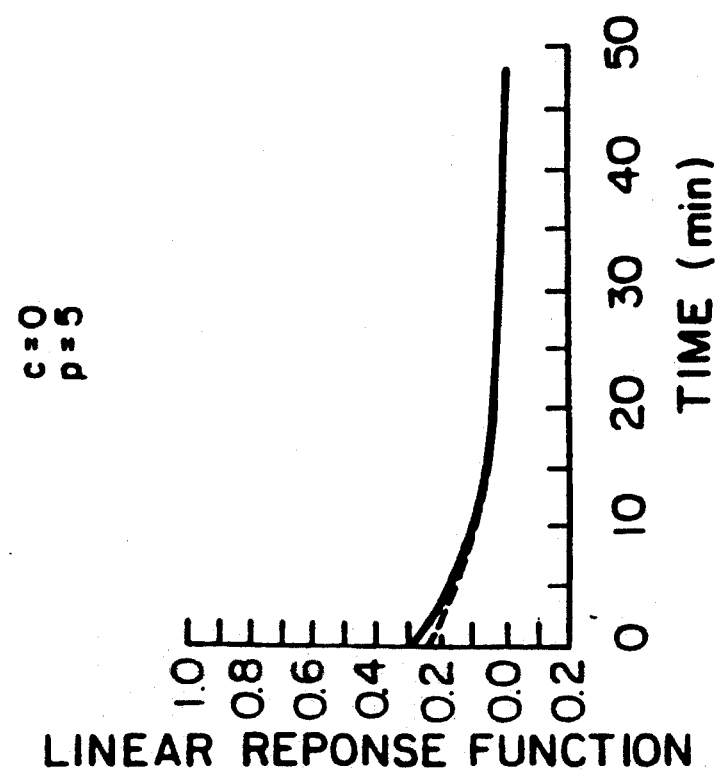
Figure 5D:
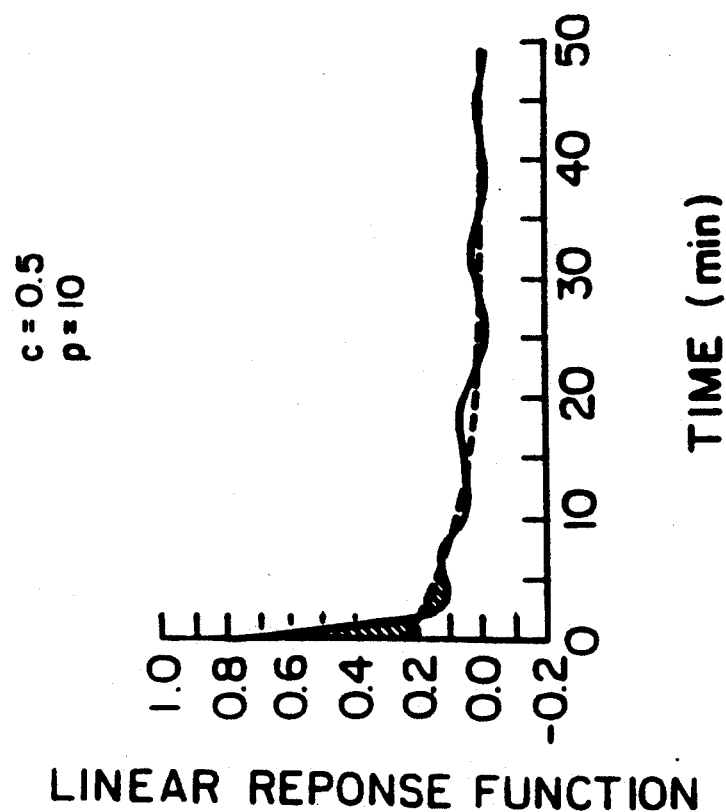
Figure 5C:
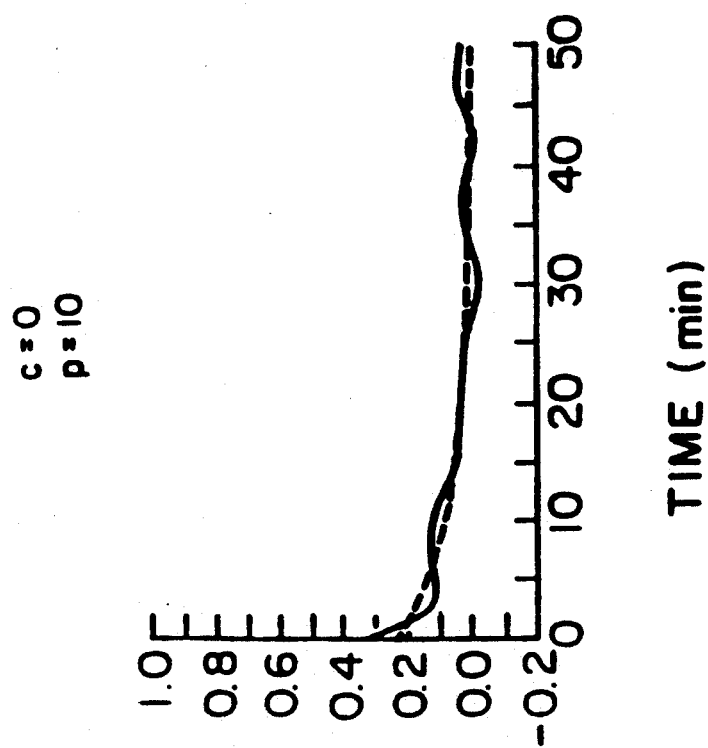
Figure 5F:
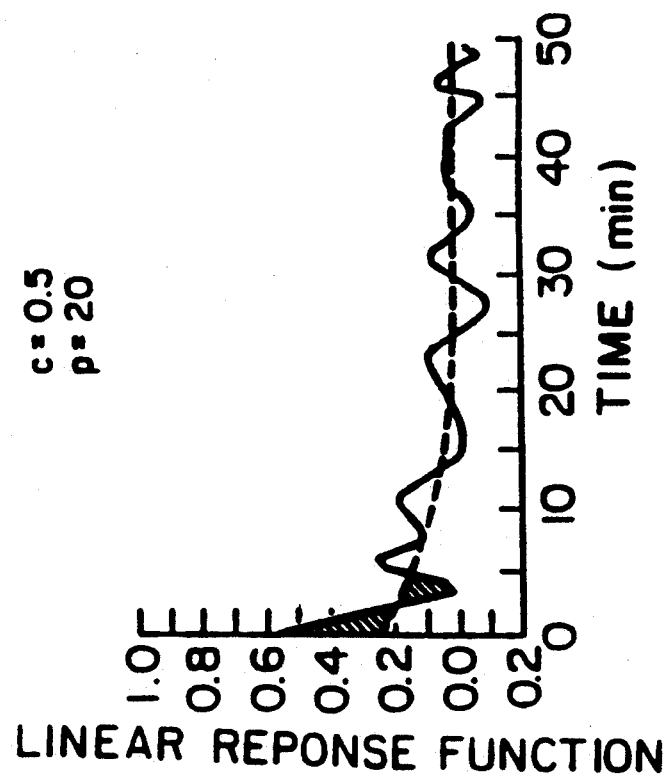
Figure 5E:
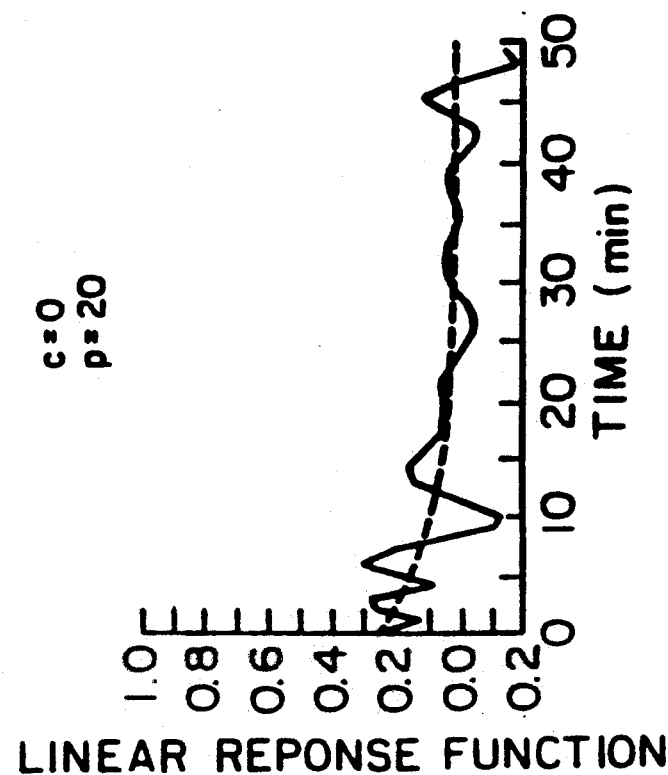

The rapid convergence of the DOP method is distorted by the presence of noise in the data. FIG. 5 shows the LRFs calculated from the blood input curve and the organ output curve seen in FIG. 3B. Noise was added only to the organ curve. Comparing the LRFs in FIGS. 5A, C, E with those in FIGS. 4A, C, E demonstrates that the presence of noise dramatically alters the convergence characteristics of the DOP method. Low numbers of polynomials (Z=5) produce systematic errors in the first half of the LRF (FIG. 5A). High numbers of polynomials (Z=20) amplify inherent oscillations in the LRF dramatically. In between these extremes an "optimal" number of polynomials can be determined which leads to a still oscillating but systematic error-free LRF (FIG. 5C). The presence of blood volume (blood background) does not change this behavior essentially as can be seen from FIGS. 5B, D, E. There is also an "optimal" number of polynomials which permits a systematic error free LRF. But in the presence of noise, it might be cumbersome to mathematically separate components of the "true" response from a possibly underlying blood background activity. Therefore, in all clinical studies, which are always contaminated with noise, it has been recommended to eliminate the delta functional partition of the LRF by integration of the organ output function followed by differentiation of the integral of the linear response function.

Data Acquisition

The acquisition mode of the dynamic scintigraphic study and the determination of the input function depends on the tracer used and the organ to be investigated. Thus it is described a data acquisition and processing of the input function for the clinical example used in this disclosure.

The gamma camera was positioned over the thyroid of the patient and images were recorded in 5 sec intervals for 100 sec, 10 sec intervals for 2 min, 20 sec intervals for 1 min, 1 min intervals for 4 min, and 2 min intervals for 18 min. Since simultaneous images of the heart and thyroid could not be recorded with the gamma camera available, an external scintillation detector was placed over the heart of the patient. The counts recorded by the probe were automatically written into one corner of the images. This was accomplished by a electronic switch and buffer system linking the gamma camera and the computer. Each counting event passing by the pulse height analyzer of the probe caused an x,y signal fitting in one of the corners of the gamma camera image. In order to prevent counting overflow, the coordinates were shifted sequentially pixel by pixel by stepwise electronic offset addition $\Delta x$, $\Delta y$ to the x and y position. The size of the total area thus casing the detector's events was a $8 \times 8$ matrix. Simultaneously with acquisition, blood samples were drawn at 5, 10 and 20 min after injection. The scintigraphic study was then interpolated, and the input function generated by drawing a region of interest over the $8 \times 8$ matrix. The input function recorded over the heart region mainly reflect the tracer's time course in the blood. Since $^{123}I$ is diffusible, the curve included activity which had accumulated in extra cardiac tissue. In order to overcome the problem of processing such a compound curve, the recorded curve from the cardiac region of interest was normalized with the 6 min plasma value. In a second step, the heart curve for times greater than 6 minutes was replaced by an exponential fit of the plasma values through 5, 10, 20 minutes. With the "corrected input" curve and the scintigraphic images, the linear response function (LRF) was calculated in each pixel as a function of time using calibration factors of the gamma camera $F_G$ and the well counter $F_W$ that were determined prior to patient study according the procedure described in the following section.

Calibration of the Gamma Camera and the Well-Counter

In many of our applications the gamma camera was calibrated by use of phantoms of the approximate shape of the organ being studied (thyroid phantom, Alderson liver and kidney phantom). These were filled with a known activity of the radionuclide used in the study, and placed in a scattering medium approximating the size and shape of the region of a patient being imaged at the approximate depths of the organ in this region. The calibration factor $F_G$(MBq*min/counts) was calculated by drawing a region of interest around the organ and dividing the known activity (MBq) by the corresponding count-rate (counts/min). The well counter was calibrated by counting a known activity in 1-2 ml solution and calculating the factor $F_W$(MBq*min/counts). The calibration of the gamma camera is only an approximation for any given patient when organ size and depths vary from that of those used to measure $F_G$. Methods have been developed for generating buildup factors to generate attenuation corrected images for use in absolute volume and activity measurements. Wu et al., "Tc-99m HIDA dosimetry in patients with various hepatic disorders", J. Nucl. Med., 25:905-912 (1984); Siegel et al., "The buildup factor: Effect of scatter on absolute volume determination", J. Nucl. Med., 26:390-394 (1985); and Keller et al., "Direct determination of the attenuation coefficient for radionuclide volume. measurements", J. Nucl. Med., 28:102-107 (1987).

Clinical Examples

Figure 6:
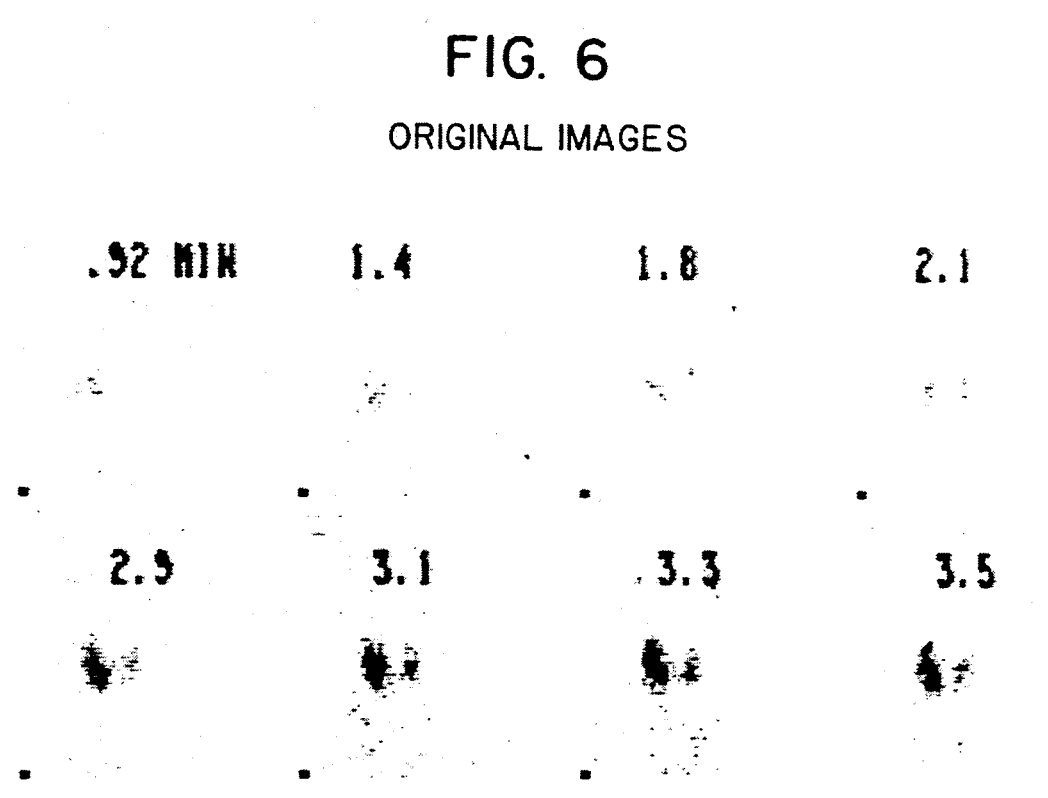
Figure 7:
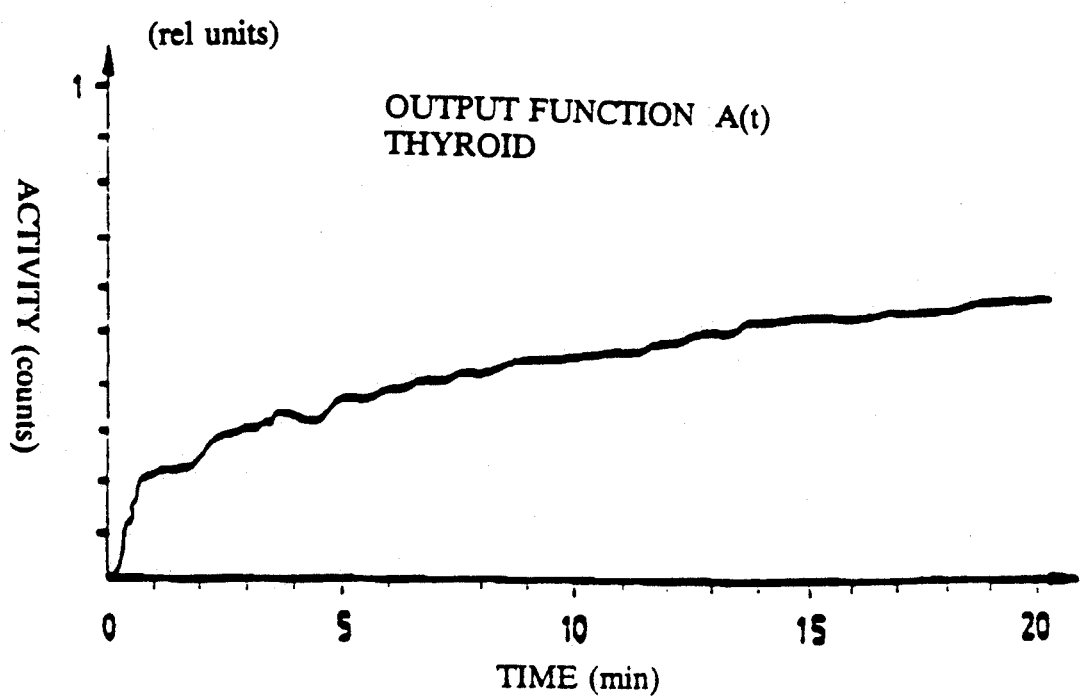
FIG. 7. Time activity curve from a region of interest including the entire thyroid gland. The curve represents the output function A(t) of the thyroid.
Figure 8:
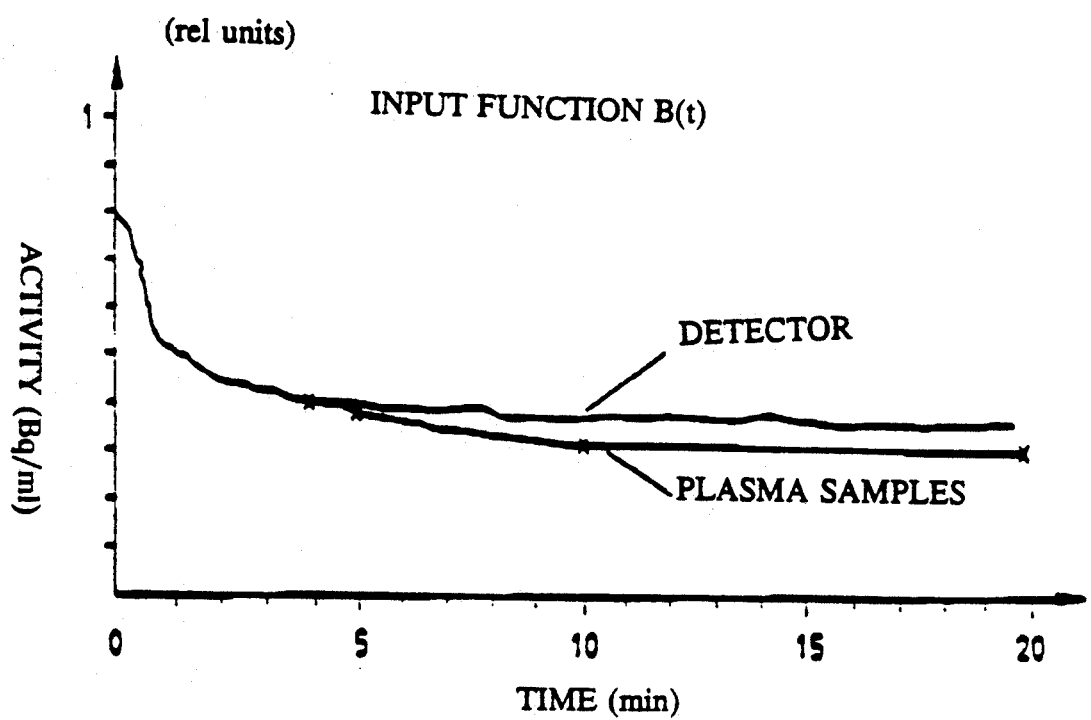
FIG. 8. Depicts a detector curve obtained by placing a scintillation detector over the heart to count the time activity course of the tracer in the blood pool. Blood samples were obtained 3.5, 5, 10 and 20 min after injection, and the activity calculated in 0.5-1 ml plasma. The discrete plasma values were interpolated by an exponential fit, and the plasma value at 5 min was used to normalize the detector curve at this time point. Detector values at times greater than 5 min were then replaced by values obtained from the interpolated plasma curve. This procedure corrected the detector curve for nontarget tissue activity and forms the input function B(t).

In FIG. 6 typical images from a dynamic $^{123}I$ thyroid study as described above are shown. The grey scale has been adjusted in each image to encompass exactly the same range of count rates, so that visual comparison of these images with the results from the deconvolution process can easily be made. In FIG. 7, the time activity curve from a region of interest (ROI) drawn over the entire thyroid is shown. This curve portrays the accumulation of the tracer into the thyroid. It should be noted that parameters like peak value, height, or slope of this curve are functions of at least two organs (the thyroid, and the kidneys) which clear the iodine from the blood with comparable rates. The activity in the patient's blood was monitored simultaneously with the acquisition of the scintigraphic data by the method described above. The upper curve in FIG. 8 served as a first order approximation of the input function. This curve was then corrected and normalized by plasma samples taken during the scintigraphic acquisition (see FIG. 8 lower curve).

Figure 9:
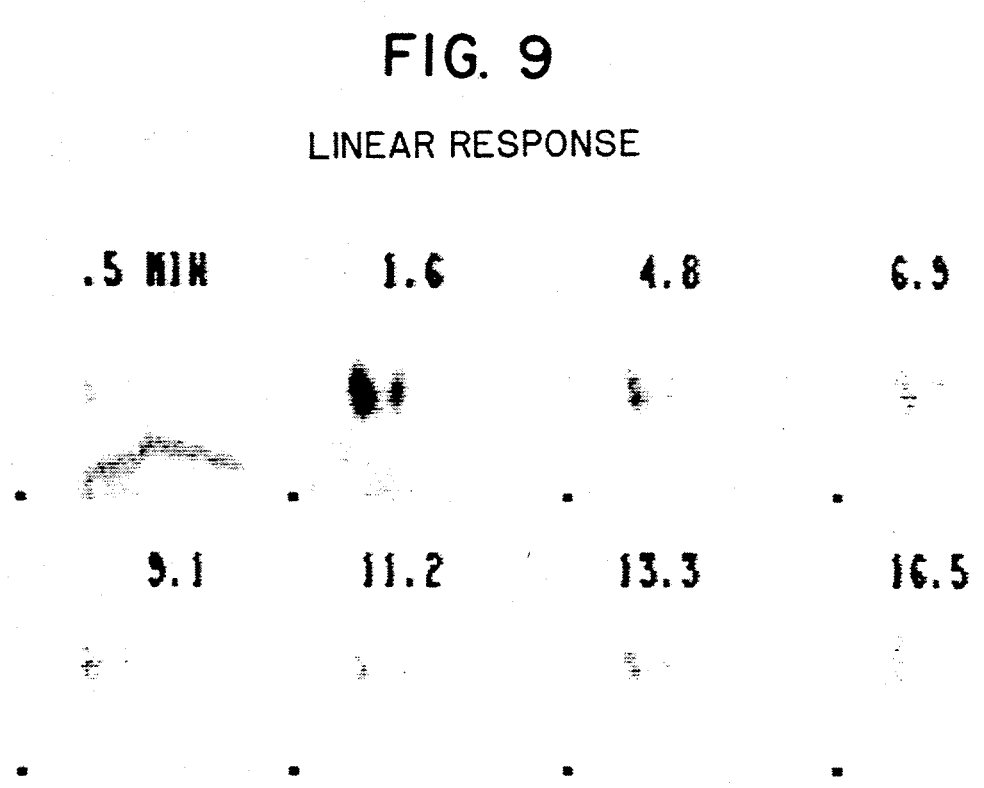
Figure 10:
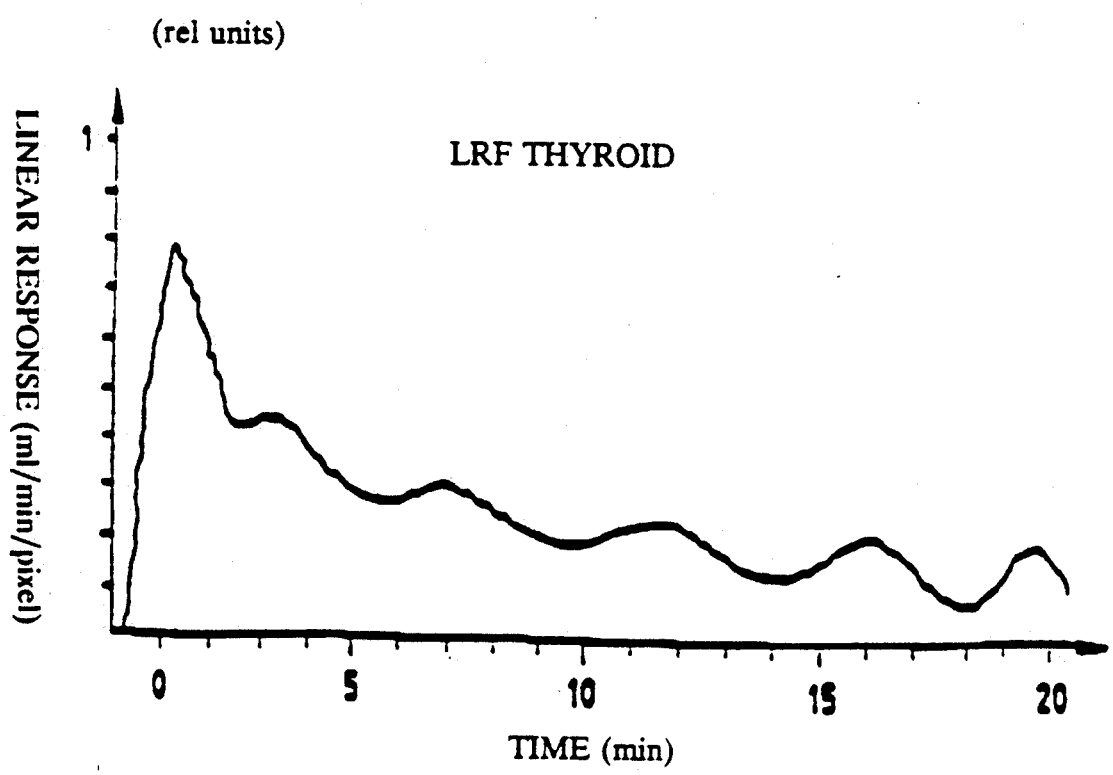
FIG. 10 shows a time course of the LRF values in the entire thyroid. The oscillations were caused by the polynomial approach of the deconvolution technique and are not related to physiological processes.

In FIG. 9, images of the LRF calculated from the organ and blood activity (input-output events) are shown. The 8 images are a subset of the total of 50 images produced and represent the first 6 minutes of the tracer kinetics. In order to compare the kinetic behavior of the LRF with the scintigraphic data, the grey scale has been adjusted in each image here as before. The LRF images show the response to a delta functional input of the tracer into the blood and, because no recirculation of the tracer in the blood is allowed, the dependence of the LRF on the kidneys or other organs was thus eliminated. This can be visualized by looking at the LRF images (FIG. 9) and at the time course of the LRF values in the entire thyroid (FIG. 10). The image and curve values commence with low values, rapidly reach a maximum, followed by a rapid and then a slower oscillating decline. This initial response leading to the peak value represents the rapid transfer of the tracer from the blood compartment to both thyroid and nonthyroid tissue spaces. The rapid decline from the peak is due to a rapid reflow of the tracer from the extracellular space into the blood. Thereafter, the LRF declines more slowly, at rate a. This part of the LRF can be approximated by a monoexponential function $A \cdot e^{-a \cdot t}$ where A represents the injected activity remaining in the thyroid most of which is trapped and organified (clearance). A was determined in each pixel x,y and presented the Iodine plasma clearance A(x,y) in a functional image. Montz and Stritzke (1982). The example demonstrated herein is physiologically abnormal because some of the trapped $^{123}I$ is being released rather than being retained and organified. If all of the trapped $^{123}I$ is retained, the rate constant would be zero and the LRF would show a constant plateau for $0 \leq t \leq T$, where t denotes the time, and T=25 min the duration of the study. We have not studied this process for longer than 25 minutes.

VI. Hardware Implementation

Figure 11:
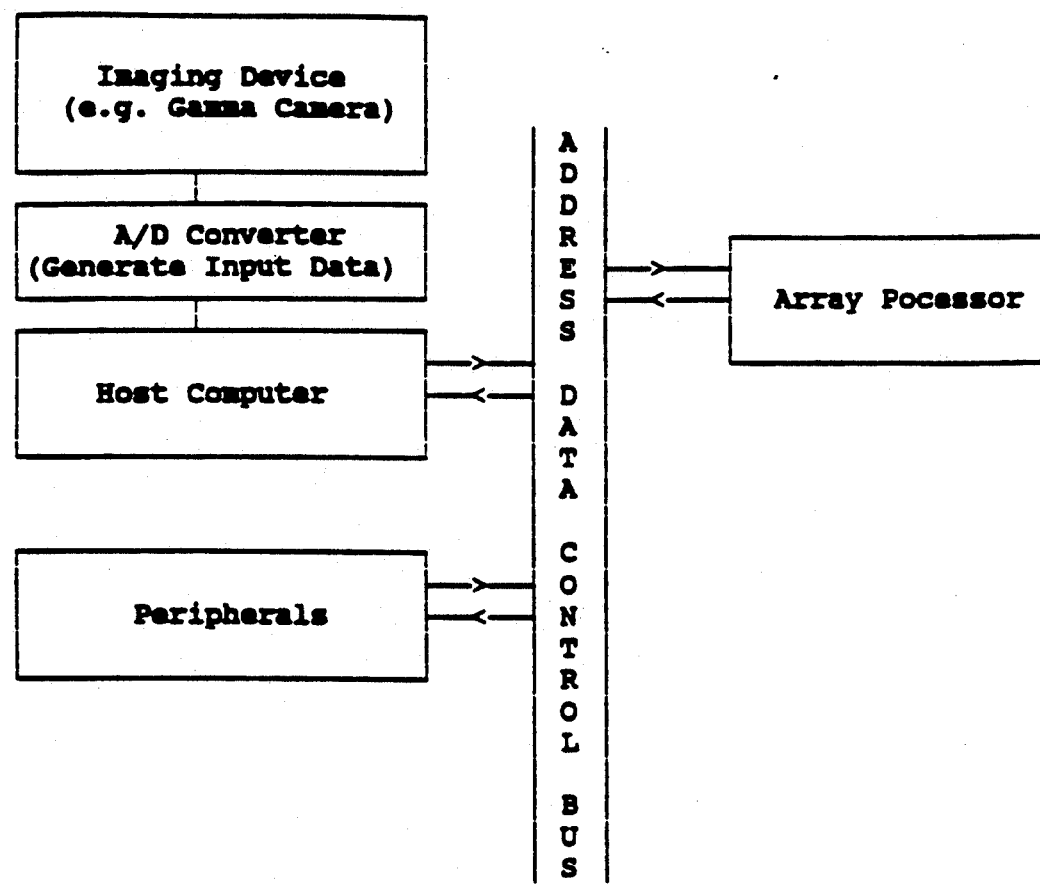
FIG. 11 outlines the hardware structure of an array processor working in conjunction with a general purpose host computer wherein the array processor is connected directly onto the data, address and control bus of the host to process the incoming data from the A/D converters efficiently.

It has been shown here that the approach based on deconvolution methods with orthogonal polynomials (DOP) leads to an estimation of the linear response function contained within the time sequence of the same, single pixel in the associated images. The DOP method described is best used with an array processor. The method has been divided into a preprocess step and the actual time consuming estimation of the LRF in each pixel. The preprocess step can be performed in the host computer and needs numerical values of a well defined input function. See FIG. 13 for the typical flow diagram of a program used to extract features from images of size 64 by 64 using a general purpose host computer, such as Digital Equipment's Corporation VAX 11/750. Conversely, for more efficient operation and reduced computation time, an array processor can be interfaced to the data/address/control bus of a general purpose host to perform those matrix computations for which the host is not optimized for. A hardware configuration for such a host/array processor combination is shown in FIG. 11, wherein the image is digitized by the analog to digital converter(s) and subsequently stored in the host's memory. Now the array processor has access to the data as well as the precomputed two dimensional matrixes $c_z$ and $d_z$ as outlined in equations 15 to 23, and 34.

Figure 12:
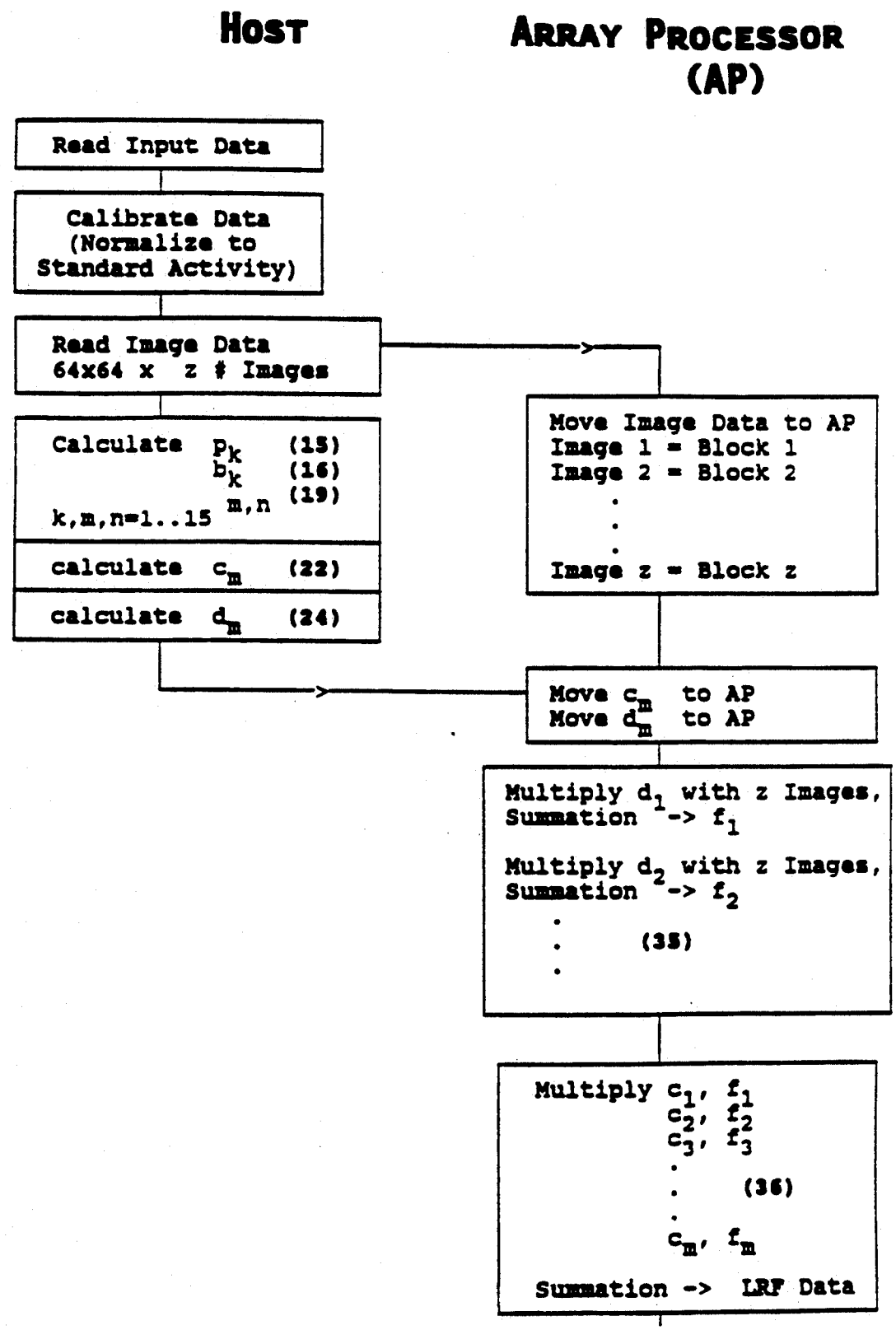
FIG. 12 details the software operations to be conducted by the array processor and the host processor to extract the information in the digitized images.
Figure 12:
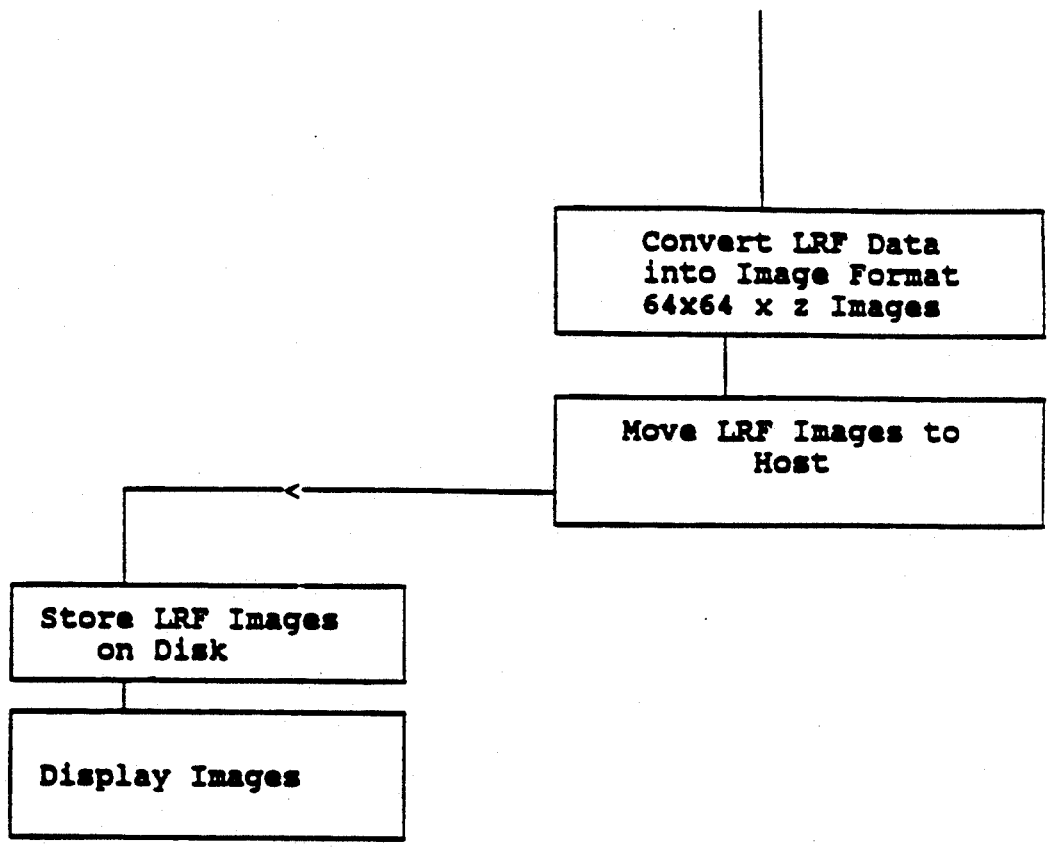

The host general purpose computer in accordance with FIG. 12 showing the software flow in a host/array processor combination then performs the computation of orthogonal functions of the degree Z, the estimation of an adjoint operator, and an orthonormalization process. This preprocess results in two Z*U matrices, where U is the number of the images and Z the degree or number of the polynomials used. The matrix values do not depend on any measurements of the organ data. Although the rest of the process needs only the operations of multiplication and summation of the image data with the matrices determined from the preprocess, it is time consuming and therefore assigned to the array processor for processing. For the computers usually available in nuclear medicine, the method can be performed in blocks of values. This is usually the preferred method because of limitations of the host's and array processor's memory. This causes some inefficiencies in terms of full computation speed of the array processor, but avoids multiple disk to memory transfers of the scintigraphic data. The computation is straight forward and does not need any a priori information in terms of shape and periodicity of the scintigraphic data. The LRF images were calculated using typically 15 Legendre polynomials and the scintigraphic images interpolated into 50 images. The computation time on a PDP-11/23 without hardware floating point arithmetic was about 3 hours. This time decreased to 45 minutes using a PDP-11/34 with floating point arithmetic and cache memory, and was further dramatically decreased by the implementation of the DOP method on a PDP-11/34 with floating point arithmetic, cache memory, and array processor. With the latter configuration, the computation intensive part of the method was reduced to 3 minutes for the full computation of the LRF in floating point format. The time to compute a LRF in 120 images (64×64 matrix size) on a VAX-11/750 with hardware floating point and 8MB of memory was 10–20 minutes depending on the clinical load on the computer.

Comparison with the Prior Art

Comparing the DOP method with the Fourier transform and discrete deconvolution methods, the most widely used tools in the literature for deconvolution purposes. Diffey et al. (1976); Alderson et al. (1979); Kuruc et al. (1983); Knesaurek and Spaventi, "Comparison of three deconvolution techniques in renography", Eur. J. Nucl. Med, 9:254–256 (1984); Jacquez, *Compartmental analysis in biology and medicine*, Elsevier Publishing Co, NY. (1972); Gremmel et al., "Auswertung von Isotopennephrogrammen durch die Entfaltungsmethode", Nucl. Med., 18:46–51 (1979); Valentinuzzi, "Discrete deconvolution", Med. Biol. Eng., 13:123–125 (1975); and Ham et al., "Radionuclide quantitation of left-to-right cardiac shunts using deconvolution analysis: Concise communication", J. Nucl. Med., 22:688–692 (1981). The results demonstrate that the DOP method is superior to these other methods, particularly when data are contaminated with noise. The difficulty in applying the technique of dividing Fourier transforms or discrete deconvolution is that the methods per se do not acknowledge the existence of noise in the data. Diffey et al. (1976); Hunt, "The inverse problem of radiography", Mathem. Biosc., 8:161–179 (1970). Kaplan et al. (1969) observed that the presence of even minor errors in the measured data result in large perturbations in the solution (ill-conditioned nature of the matrix approach). Kaplan et al., "The inverse problem of radioisotope diagnosis: A computational method for determining the location and size of tumors", Math. Biosc., 5:39–55 (1969). Diffey et al. (1976) proposed data bounding to contain noise components which exceed certain limits. Diffey et al. (1976). This is an iterative process reducing the adverse impact of noise. This kind of noise reduction, or simple smoothing techniques, may help. Nonetheless, it must be emphasized that the simple discrete deconvolution method is inherently inaccurate. One reason that the DOP method handles presence of noise very well may be explained by analyzing equ.30. Every value of the LRF (or its integral) in time calculated in a particular pixel is (among other terms) proportional to a sum term which represents the integral over all organ output data in time and in this particular pixel. Consequently, the statistical quality of the LRF at time $t_n$ is not only dependent on the statistical quality of the measured organ output function at $t_n$, but rather on the total count rates accumulated during the entire study.

Many methods have been investigated which seek to achieve other satisfactory solutions by the incorporation of a priori knowledge of the organ. These are expressed in mathematical form as a set of constraints, such as a combination of smoothness, monotonicity or non-negativity or total linear least squares (TLLS). Kuruc et al., "An improved deconvolution technique for the calculation of renal retention functions", Comp. Biom. Res., 15:46–56 (1982); and Van Huffel et al., "Reliable and efficient deconvolution technique based on total linear least squares for calculating the renal retention function", Med. & Biol. Eng. & Comp., 25:26–33 (1987). In general, incorporation of constraints leads to either an iterative or a regularized matrix technique. Hunt (1970); Kuruc et al. (1982); Van Huffel et al. (1987); Phillips, "A technique for the numerical solution of certain integral equations of the first kind", J. Assoc. Comput. Mach., 9:84–97 (1962); and Twomey, "The application of numerical filtering to the solution of integral equations encountered in indirect sensing measurements", J. Franklin Inst., 279:95-109 (1965). The calculation of the regularization parameters is either relatively time consuming or must be estimated empirically from simulation studies. The constraints applied are supposed to vary with the system studied and there is probably no optimal deconvolution applicable to the solution of every problem. Nimmon et al., "Practical application of deconvolution techniques to dynamic studies", In: Medical Radionuclide Imaging, IAEA, Wien 367-388 (1981).

Fleming and Goddard (1974) introduced a deconvolution technique for the renogram in which the Laplace Transform of the input function plays a role. Fleming and Goddard, "A technique for the deconvolution of the renogram", Phys. Med. Biol., 19:546-549 (1974). This means that a mathematical expression must be found which is not too complicated for the required operations and is a good approximation of the input function. Stekelenburg et al. (1978) and (1976) and Kenney (1975) suggested a two or three exponential approximation of the input function. Kenney, "Deconvolution analysis of the scintillation camera renogram", Br. J. Radiol., 48:481-486 (1975).

The choice of number of polynomials used is a consideration which still remains to be settled. A criterion which provides the right or optimal number of polynomials is certainly dependent on the type of study and the noise levels. This application does not attempt to fully evaluate this criterion. However, computer simulations show that, in the case of input-output events containing no noise components, DOP needs not more than 5 polynomials in order to calculate a systematic error-free LRF for the one case tested. With data containing noise components, there was noted an "optimal" number of polynomials which did minimize the amplitudes of inherent oscillations. This parameter has been determined experimentally when used in clinical studies. In studies like the $^{99m}$Tc-MDP bone, or $^{123}$I thyroid, or $^{99m}$Tc-HIDA hepatobliary scans, 15 polynomials fit the LRF without evidence of oscillations or oversmoothing the LRF. It has been shown, as described in Stritzke et al., "Performance of quantitative functional imaging using optimal two-dimensional restoration and temporal deconvolution of dynamic scintigraphic studies", Comp. Ass. Radiol. (CAR), Berlin (1987), that application of two-dimensional count and image dependent restoration filters significantly improved the quality of functional images derived from the LRF calculated according to the method described. King et al., "Digital restoration of Indium-111 and Iodine-123 SPECT images with optimized Metz filters", J. Nucl. Med., 27:1327-1336 (1986). Thus, in filtered $^{131}$I-hippuran studies 20 polynomials resulted in optimal fits.

The problem of how to handle contributions of blood-background or more accurate partition blood volume (see equ.2) measured simultaneously with the target organ activity in a deconvolution process has not been satisfactory addressed as yet in the literature. Chackett (1978) showed that Steckelenburg's (1978) and (1976) compartment analysis of the renogram can be modified to take into account the fact that the measured output function often includes a contribution directly from the input function. Chackett, "The application of transform methods to hippuran renograms", Phys. Med. Biol., 23:1199-1202 (1978). In the renogram case this comes about because the gamma camera placed over the kidneys inevitably measures extra-renal plasma activity. Chackett assumed, as in this disclosure, that this additional activity bears a constant proportionality to B(t). It was shown, as described in Stritzke et al., (1985), that a constant partition of the blood (or plasma) activity simultaneously measured with the target organ activity generally leads to a delta functional partition or singularity of the linear response function. This principally happens when diffusible tracers are being used and monitored by a single detector or gamma camera systems which are not able to distinguish regional blood and organ activity. With equ.1 and equ.2 one can write the relationship between measured activity, partition blood volume and blood input function as:

$$A(x, y, t) = c(x, y) \cdot B(t) = \int_0^t h(x, y, t - t') \cdot B(t') \cdot dt' \quad (39)$$

where the first term represents partition blood volume and the integral term the transfer of the tracer from blood to and through the cells of the target organ. Partition blood volume can be assumed to be zero when non-diffusible tracers are being used, like $^{99m}$Tc-labeled blood cells which do not leave the blood pool during the time of investigation. Then the integral term in equ.39, specifically the linear response function, describes flow and dispersion through the target organ.

It has been showed how to handle the sometimes inevitable singularity $\delta(t)$ in the linear response function. When diffusible tracers are being used, it might be recommended to apply the "integral" technique by using equ.14 in order to eliminate the $\delta(t)$. Sometimes it is more convenient to apply the equation $|A> = |B'H>$ (instead of equ.14) where B'(t) is given simply by the first derivative of the blood input function B(t). Thus the organ function $|A>$ needs not be integrated (which often saves computing time). If the user is assured that partition blood volume might not have a significant contribution to the organ linear response function, equ.14 can be replaced by $|A> = |B|h>$. The deconvolution process then returns the linear response function instead of its integral. This approach has been applied to measure blood flow and volume in a mechanical circulation phantom and in animals using technetium pertechnetate and technetium labeled red blood cells, respectively. Stritzke et al., "Non invasive assessment of absolute renal blood flow (RBF) by temporal deconvolution using orthogonal polynomials", J. Nucl. Med., 29:862-863 (1988).

From the above description of the invention it is apparent that there is provided a method as well as an apparatus having particular advantages before listed as desirable, but which can be clearly susceptible to simple modifications in form, proportion, number of parts and function without departing from the principle involved or sacrificing any of its advantages.

In order to comply with the language of the statutes the invention has been described in language specific to one area, that of scintigraphic imaging. It is to be understood that the invention is no limited to the specific features shown, but that the means comprised herein and disclosed are applicable to other fields, not limited to the ones enumerated before, namely seismic, radar etc.

The invention is therefore claimed in any of its forms or modifications within the legitimate and valid scope of the appended claims.

APPENDIX ¢

Figure 13:
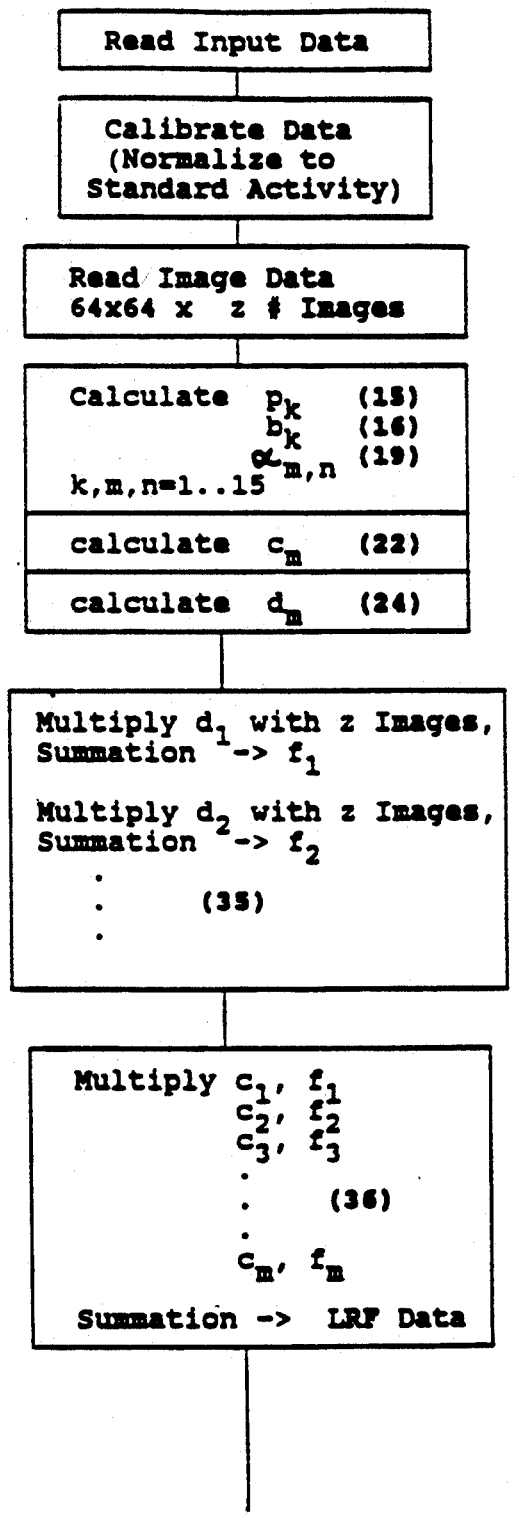
FIG. 13 outlines the flow diagram of the disclosed DOP method as implemented in a general purpose computer, such as the Digital Equipment Corporation VAX 11/750.
Figure 13:
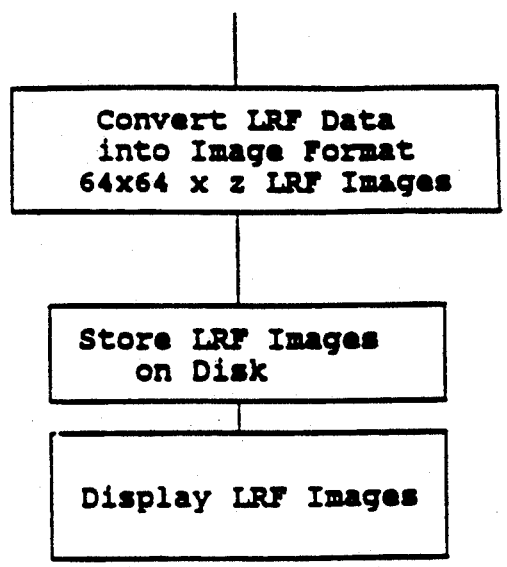

A FORTRAN program source listing detailing the extraction of LRU's from scintigraphic images using a general purpose computer is enclosed herein. The same subroutines outlined here can be modified and adapted by one skilled in the art for operation on an array processor linked to a conventional computer functioning as a "front end" or a "host" to the array processor. Figure 13 gives a streamlined view of the operation of the DOP method within a host mainframe computer.

```
C** PROGRAM TO CONTROL DECONVOLUTION PROCESS

PROGRAM LRFS

CHARACTER NAM*64,INAME*64,EXT*3,RESP*1,OPT*1
      INTEGER*2 LOC
      BYTE ENTER
```

```
        WRITE(*,1)'ENTER THE CURVE FILE, WITH EXTENSION:'
        READ(*,1) NAM
1       FORMAT(A)
        WRITE(*,1)'ENTER THE IMAGE FILE''S EXTENSION:'
        READ(*,2)EXT
2       FORMAT(A3)
        LOC = INDEX(NAM,'.')
        INAME = NAM(1:LOC)//EXT
C                                               ! SKIP OR
        TYPE *,'LRF1 :',NAM
        CALL INPSUB(NAM,LOC)                    ! CREATE <NAME>.DTA FILE
        TYPE *,'LRF1 :',NAM

WRITE(*,*)'MERGE AORTIC AND HEART CURVES [Y/N]'
        READ(5,6601)ENTER
6601    FORMAT(A1)
        IF (ENTER.EQ.'Y') THEN
           CALL CURV_SUB4(NAM,LOC,OPT)
        ELSE
           CALL CURV_SUB2(NAM,LOC,OPT)          ! READ <NAME>.DTA FILE
                                                ! CREATE <NAME>.CRV FILE
        ENDIF

CALL MAIN_SUB1(NAM,INAME,LOC)
        END
```

```
            Digital Equipment Corporation - VAX/VMS Version V5.0

ANALYSIS

INPSUB

FR3 00000

C**************************
C--- SUBPROGRAM TO CONTROL INPUT--
C--- TO WRITE DATAFILE FOR USE IN --
C---   CURVSUB
C
        SUBROUTINE INPSUB(NAME,LOC)

CHARACTER NAME*64,FNAME*64
        REAL*4 PLSMPL(10),TIME(10),FACTOR,MIN

INTEGER*4 NUM
        INTEGER*2 LOC
        WRITE(*,*)'SKIP WITH [RET] OR'
        WRITE(*,*)'ENTER THE NUMBER OF PLASMA SAMPLES '
        READ(5,100) NSMPL
100     FORMAT(I2)
        IF (NSMPL.LE.0.OR.NSMPL.GT.10) GOTO 102
```

```
        DO 1 I = 1,NSMPL
        WRITE(*,*)'ENTER THE TIME IN MINUTES OF THE NUMBER ',I,
     1      'BLOOD SAMPLE, [USE DECIMAL POINTS]'
        READ(*,*) TIME(I)
        WRITE(*,*)'ENTER THE BLOOD VALUE IN CPM OF THE NUMBER ',I,
     1      'BLOOD SAMPLE, [USE DECIMAL POINTS]'
        READ(*,*)FLSMPL(I)
        WRITE(*,*)
1       CONTINUE
2       WRITE(*,*)'ENTER THE NUMBER OF THE INCORRECTLY ENTERED SAMPLE
     1      OR [0] TO CONTINUE'
        READ(*,*) I
        IF(I.LT.1.OR.I.GT.10)GOTO3
        WRITE(*,*)'ENTER THE TIME OF THE ',I,'TH SAMPLE'
        READ(*,*)TIME(I)
        WRITE(*,*)'ENTER THE BLOOD VALUE OF THE ',I,'TH SAMPLE'
        READ(*,*)FLSMPL(I)
        GOTO2
3       WRITE(*,*)'IN HOW MANY ML WHERE THE SAMPLES'
        READ(*,*) ML
        WRITE(*,*)'ENTER THE HEMATOCRIT IN %'
        READ(*,*)HCT
        HCT = HCT/100.
        WRITE(*,*)'ENTER THE WELL COUNTER SENSITIVITY(NANOCURIE*CTS/MIN)'
        READ(*,*)SW
        WRITE(*,*)'ENTER THE GAMMA CAMERA SENSITIVITY(NANAOCURIE*CTS/MIN)'
        READ(*,*)SG
        FACTOR = SW/SG
        DO 4 I = 1,NSMPL
        FLSMPL(I) = FACTOR*FLSMPL(I)/((1.-HCT)*ML)
4       CONTINUE
        WRITE(*,*)'FOR HOW MANY MINUTES WAS THE STUDY PERFORMED'
        READ(*,*)MIN
C
C--- WRITE DATA FILE TO DISK
C
        FNAME = NAME(1:LCC)//'.DTA'
        CALL LIB$GET_LUN(NUM)
        OPEN(NUM,FILE=FNAME,STATUS='NEW',IOSTAT=IOS)
        IF(IOS.NE.0)GOTO 101
        WRITE(NUM,*,IOSTAT=IOS) NSMPL,MIN
        WRITE(NUM,*,IOSTAT=IOS) (FLSMPL(I),I=1,NSMPL)
        WRITE(NUM,*,IOSTAT=IOS) (TIME(I),I=1,NSMPL)
        CLOSE(NUM)
        IF(IOS.NE.0)GOTO101
        GOTO 102
101     WRITE(*,*)'ERROR OPENING/READING DATA FILE'
        WRITE(*,*)' ERROR NUMBER ',IOS
102     RETURN
        END
```

```
555555555555555555555555555555555555555555555555555555555555555555555555555555
5555555555555555555555 Digital Equipment Corporation - VAX/VMS Version V5.0  5555555555555555555
555555555555555555555555555555555555555555555555555555555555555555555555555555
```

```
              AAA   N   N   AAA   L         Y   Y   SSSS   III   SSSS
             A   A  NN  N  A   A  L          Y Y   S       I    S
             A   A  N N N  A   A  L           Y    SSS     I    SSS
             AAAAA  N  NN  AAAAA  L           Y       S    I       S
             A   A  N   N  A   A  LLLLL       Y    SSSS   III   SSSS

CCCCCCCC  UU    UU  RRRRRRR   VV    VV              SSSSSSS  UU    UU  RRRRRRR   22222
   CCCCCCCC  UU    UU  RRRRRRR   VV    VV              SSSSSSS  UU    UU  RRRRRRR   22222
   CC        UU    UU  RR    RR  VV    VV              SS       UU    UU  RR   RR        22
   CC        UU    UU  RR    RR  VV    VV              SS       UU    UU  RR   RR        22
   CC        UU    UU  RRRRRRR   VV    VV              SSSSSS   UU    UU  RRRRRRR       22
   CC        UU    UU  RRRRRRR   VV    VV              SSSSSS   UU    UU  RRRRRRR      22
   CC        UU    UU  RR  RR     VV  VV                    SS  UU    UU  RR   RR     22
   CC        UU    UU  RR   RR    VV  VV               SS   SS  UU    UU  RR   RR    22
   CCCCCCCC  UUUUUUUU  RR    RR    VVVV     ---------  SSSSSSS  UUUUUUUU  RR    RR  2222222
   CCCCCCCC  UUUUUUUU  RR    RR    VVVV     ---------  SSSSSSS  UUUUUUUU  RR    RR  2222222

FFFFFFFFFF   000000   RRRRRRR    1111    44    44    7777777
              FFFFFFFFFF   000000   RRRRRRR    1111    44    44    7777777
              FF           00   00  RR   RR    1111    44    44         77
              FF           00   00  RR   RR    1111    44    44         77
              FF           00   00  RR   RR            44    44        77
              FF           00   00  RR   RR            44    44        77
              FFFFFFFF     00   00  RRRRRRR    1111   4444444444      77
              FFFFFFFF     00   00  RRRRRRR    1111   4444444444      77
              FF           00   00  RR   RR    1111         44       77
              FF           00   00  RR   RR    1111         44       77
              FF           00   00  RR   RR                 44      77
              FF           00   00  RR   RR     11          44   - 77
              FF           000000   RR   RR     11          44     77
              FF           000000   RR   RR     11          44     77
```

```
C************************
C***** PROGRAM TO READ AND NORMALIZE CURVES
C***** GENERATED FROM MICRODELTA FOR DCF *******
C*****************************************
C*** BY PETER STRITZKE ******
C***********
        SUBROUTINE CURV_SUB2(NAME,LOC,OPT)
C       ****************************
C
        INCLUDE 'HEAD_CONV.FOR' ! DECLARATIONS AND EQUIV

C       *****************
        CHARACTER NAME*64,DATFL*64,OPT*1
C
        REAL*4 C(128),C1(128),X(128),C_OLD(128),P_K(128)
        REAL*4 CBUFF(128),C111(128)
        REAL*4 FLGNFR(10),TIME(10),NORMFACT,MIN,P_BUFF(20),CBU(128)
        INTEGER*2 STEP, NUM,LOC,IOS
        INTEGER*4 CHAN
        BYTE ICHAR
C       *****************

CALL VTINIT
        CALL VTCLEAR(1)

C* OPEN CURVE FILE **
C***** CURVES ARE READ FROM [DELTA.IMAGES]
        TYPE *,'CURV_SUB2.FOR '
        WRITE(5,4157) NAME
4157    FORMAT(A25)
        CALL LIB$GET_LUN(CHAN)
        OPEN (UNIT=CHAN,FILE=NAME,ACCESS='DIRECT',
     1      STATUS='OLD',RECORDTYPE='FIXED',IOSTAT=IOS)
        IF(IOS.NE.0)GOTO 100
C*******

C****** READ HEADER INFORMATION
        READ(CHAN,REC=1)RECONE
        READ(CHAN,REC=2)RECTWO

C****** READ CURVE ONE
        READ(CHAN,REC=3)C
        CLOSE (CHAN)
C
C
        TYPE 5,PATNAM,PATNUM,EXT,DAT,ACQ,VNUM,IMGTYP,STUDY,TAPID
10      FORMAT(2X,18A1,1X,6A1,1X,3A1,2X,8A1,2X,10A1,2X,2A1,1X,A1,1X,10A1
     1      2X,8A1//)
        TYPE 6,TOTGP,G1NFRM,G1FRMR,G1GPAU,G2NFRM,G2FRMR,G2GPAU,G3NFRM,G3FRMR
6       FORMAT(' Total #Groups:',I6/
     1      ' Group-1 #Frames:',I6/
     2      ' Group-1 Frame rate (sec/frame):',F6.2/
     3      ' Group-1 Pause to next group (sec):',F6.2/
     4      ' Group-2 #Frames:',I6/
     5      ' Group-2 Frame rate (sec/frame):',F6.2/
     6      ' Group-2 Pause to next group (sec):',F6.2/
     7      ' Group-3 #Frames:',I6/
     8      ' Group-3 Frame rate (sec/frame):',F6.2/)

GNFRM(1)=G1NFRM
        GNFRM(2)=G2NFRM
        GNFRM(3)=G3NFRM
        GFRMR(1)=G1FRMR
        GFRMR(2)=G2FRMR
        GFRMR(3)=G3FRMR
        GGPAU(1)=G1GPAU
        GGPAU(2)=G2GPAU
        GGPAU(3)=0

TOTFRM=G1NFRM+G2NFRM+G3NFRM
C
        T=0
        NFR=0
        DO 8 I=1,TOTGP
        DO 10 J=1,GNFRM(I)
        NFR=NFR+1
```

```
              T=T+GFRMR(I)
              X(NFR)=T/60.                    ! TIME IN MINUTES
              W1=60.*C(NFR)/GFRMR(I)          ! COUNTS/MIN
              C1(NFR)=W1      !
C
              TYPE *,'I,X,Y,DELTA T ',NFR,X(NFR),C1(NFR),GFRMR(I)
10            CONTINUE
              X(NFR)=X(NFR)+GFRAU(I)
C             CONTINUE
C
C*********
C***************
C****** READ DATA GENERATED BY INFSUB
C***** FOR NORMALIZATION OF BLOOD-POOL CURVE
C*************
              DATFL = NAME(1:LOC)//'.DTA'
              CALL LIB$GET_LUN(CHAN)
              OPEN(UNIT=CHAN,FILE=DATFL,STATUS='OLD',IOSTAT=IOS)
              IF(IOS.NE.0)GOTO 108
C*
              CALL DATRD(PLSMPL,TIME,NSMPL,MIN,IOS,CHAN)
              IF(IOS.NE.0)GOTO 104
              CLOSE(CHAN)
C
C---- NORMALIZE THE CURVE TO FIRST PLASMA SAMPLE---
C
C
C
              KT=TOTFRM                       ! IMPORTANT
C
              DO 1515 I=1,TOTFRM  ! FIND TIME POINT FOR NORMALIZATION
              IF(X(I).GE.TIME(1)) GOTO 1516
1515          CONTINUE
              TYPE *,' NO NORMALIZATION PERFORMED'
              GOTO 2725
1516          CONTINUE
              IF1=I                           ! TIME POINT FOR NORMALIZATION
              TAF=PLSMPL(1)/C1(IF1)           ! # SAMPLES = 1
              DO 1517 J=1,TOTFRM
              C1(J)=C1(J)*FN   ! NORMALIZE INPUT P&T CURVE
              TYPE *,'OLD,NEW',J,X(J),C1(J),W1
              C1(J)=W1
1517          CONTINUE
C
              IF(NSMPL.EQ.1) GOTO 2725        ! NF ! NUMBER PLASMA SAMPLES >1
C
C
              DO 2737 I=1,TOTFRM  ! GET WEIGHTS TO 1.
              C_OLD(I)=C1(I)                  ! SAVE OLD CURVE FOR GRAPH
2737          P_K(I)=1.                       ! WEIGHTS
              DO 2736 I=1,NSMPL               ! LOGARITHMN PLASMA VALUES
              type *,'plasma i,time plasma,wei ',i,TIME(i),PLSMPL(i),P_K(i)
2736          P_BUFF(I)=ALOG(PLSMPL(I))
C
C
              CALL DG2(NSMPL,TIME,P_BUFF,P_K,AA,BB)  ! Y= AA * X + BB
              BB=EXP(BB)
C
C
              DO 2735 I=IF1,TOTFRM            ! REPLACE OLD CURVE BY NEW PLASMA
              C1(I)=BB*EXP(AA*X(I))           ! VALUES FOR TIMES t>=TF
C             TYPE *,'T,O,K',I,X(I),C_OLD(I),C1(I)
2735          CONTINUE
CX            QMIN=-1.E20
CX            DO 4900 I=1,TOTFRM              ! LOOK FOR MAXIMUM
CX            IF(C1(I).GT.QMIN) GOTO 4901
CX            GOTO 4900
CX4901        KMAX=I
CX4900        CONTINUE
C
CX            DO 4903 J=1,2
CX            DO 4902 I=KMAX+2,TOTFRM-2
C             CBU(I)=(-6.*C1(I-2)+24.*C1(I-1)+34.*C1(I)+24.*C1(I+1)-6.*C1(I+2))/70.
CX4902        CONTINUE
C
CX            DO 2745 I=KMAX+2,TOTFRM-2       ! CREATE PLASMA CURVES
CX            W=-6.*CBU(I-2)+24.*CBU(I-1)+34.*CBU(I)+24.*CBU(I+1)-6.*CBU(I+2)
CX2745        C1(I)=W/70.
```

```
2X4903  CONTINUE
C
        DO 2740 I=1,TOTFRM       ! CREATE PLASMA CURVE
2740    CBUFF(I)=BB*EXP(AA*X(I)) ! FOR GRAPH
C
        NT=TOTFRM                ! IMPORTANT
        CALL PLOT_C3(NT,X,C_OLD,CBUFF,C1)
        ICHAR=ITTINR()

CALL VTCLEAR(1)
2725    CONTINUE      ! # SAMPLES >=1  DONE
C

C
        CALL VTCLEAR(1)
        WRITE(5,8819)
8819    FORMAT(' ARTIFICIAL DECAY (KIFFORAH) Y/N :',$)
        ICHAR=ITTINR()
        IF(ICHAR.EQ.'Y') THEN
8812      CONTINUE
          WRITE(5,8816)
8816      FORMAT(' IN VITRO VALUE B,A (F-F? ):$)
          READ(5,8814)BAMP,AMP
8814      FORMAT(2F)
          DO I=1,NT
            C111(I)=C1(I)
          ENDDO ! I
          DO I=1,NT
            C111(I)=C1(I)-C1(I)*BAMP*(1.-EXP(-AMP*X(I)))
          ENDDO ! I

CALL PLOT_C3(NT,X,C1,C1,C111)

ICHAR=ITTINR()
          CALL VTCLEAR(1)

IF(ICHAR.EQ.'B') THEN
            GOTO 8812
          ENDIF

C         SAVE=C1(NT-2)/C111(NT-2)
C         DO I=1,NT
C           C1(I)=C111(I)*SAVE
C         ENDDO ! I

ENDIF

C--------------------------------------------------
C---- WRITE CURVE TO DISK IN 'NAME'.CRV -----
C--------------------------------------------------
2200    CALL LIB$GET_LUN(CHAN)
        OPEN(UNIT=CHAN,FILE=NAME(1:LOC)//'.CRV',STATUS='NEW',IOSTAT=IOS)
        IF(IOSTAT.NE.0)GOTO 105
        FAK=SECNR(1)/60.         ! DO NOT CONVERT TIME VECTOR
                                  ! TO MINUTES
        TYPE *,'FACTOR CORRECT IMAGE COUNTS > ',FAK
        CALL CRVWRT(X,C1,IOSTAT,NT,FAK,CHAN)
        IF(IOSTAT.NE.0)GOTO 106
        CLOSE(CHAN)
        GOTO 1702
C--------------------------------------------------
C -- ERROR MESSAGES --------------------------------
C--------------------------------------------------
100     WRITE(*,*)'ERROR OPENING MICRODELTA CURVE FILE'
        GOTO 1987
101     WRITE(*,*)'ERROR READING NON-CURVE DATA'
        GOTO 1987
102     WRITE(*,*)'ERROR READING CURVE DATA'
        GOTO 1987
103     WRITE(*,*)'ERROR OPENING DATA FILE FOR NORMALIZATION'
        GOTO 1987
104     WRITE(*,*)'ERROR READING DATA FILE FOR NORMALIZATION'
        GOTO 1987
105     WRITE(*,*)'ERROR OPENING OUPUT FILE'
        GOTO 1987
106     WRITE(*,*)'ERROR WRITING OUTPUT FILE'
        GOTO 1987
1987    WRITE(*,*)'THE ERROR NUMBER IS:',IOS
1702    RETURN
        END
```

```
                    AAA   N   N   AAA      L        Y   Y   SSSS    III    SSSS
                    A A   NN  N  A   A     L         Y Y   S         I    S
                    A P   N N N  A   A     L          Y    SSS       I     SSS
                   AAAAA  N  NN  AAAAA     L          Y       S      I       S
                   A   A  N   N  A   A     L          Y        S     I        S
                   A   A  N   N  A   A     LLLLL      Y     SSSS    III    SSSS

RRRRRRRR    000000    UU     UU  TTTTTTTTTT   IIIIII   NN      NN  EEEEEEEEE
        RRRRRRRR    000000    UU     UU  TTTTTTTTTT   IIIIII   NN      NN  EEEEEEEEE
        RR    RR   00    00   UU     UU      TT         II     NNN     NN  EE
        RR    RR   00    00   UU     UU      TT         II     NN      NN  EE
        RR    RR   00    00   UU     UU      TT         II     NNNN    NN  EE
        RR    RR   00    00   UU     UU      TT         II     NNNN    NN  EE
        RRRRRRRR   00    00   UU     UU      TT         II     NN NN   NN  EEEEEEE
        RRRRRRRR   00    00   UU     UU      TT         II     NN  NN  NN  EEEEEEE
        RR  RR     00    00   UU     UU      TT         II     NN   NN NN  EE
        RR   RR    00    00   UU     UU      TT         II     NN   NNNN   EE
        RR    RR   00    00   UU     UU      TT         II     NN    NNN   EE
        RR    RR   000000     UUUUUUUUU      TT       IIIIII   NN     NN   EEEEEEEEE
        RR    RR   000000     UUUUUUUUU      TT       IIIIII   NN     NN   EEEEEEEEE

FFFFFFFFF   000000    RRRRRRRR    1111      11     333333    222222
            FFFFFFFFF   000000    RRRRRRRR    1111      11     333333    222222
            FF         00    00   RR    RR    1111     1111      33   33     22
            FF         00    00   RR    RR    1111     1111      33   33     22
            FF         00    00   RR    RR     11       11             33     22
            FFFFFFFF   00    00   RRRRRRRR     11       11           33       22
            FFFFFFFF   00    00   RRRRRRRR     11       11           33       22
            FF         00    00   RR  RR       11       11          33       22
            FF         00    00   RR   RR      11       11         33       22
            FF         00    00   RR    RR     11       11        33       22
       .... FF         00    00   RR    RR     11       11       33       22
       .... FF         000000     RR    RR     11     111111    333333   22222222
            FF         000000     RR    RR     11     111111    333333   22222222
```

C ROUTINES FOR READING, AND WRITING STUFF...
C ALL I/O ROUTINES FOR ICP PROGRAMS ARE FOUND
C IN THIS FILE
C
C
CC======ROUTINE TO READ NON-IMAGE BLOCKS======
        SUBROUTINE HEADRD(RECONE,RECTWO,BLOCK,IOS,NUM)

BYTE RECONE(512),RECTWO(512)
        BYTE BL(512),BLOCK(5120)
        INTEGER*4 NUM
        INTEGER*2 IOS,ISKIP,IJ,I,J
        READ(NUM,REC=1,ERR=99,IOSTAT=IOS) RECONE
        READ(NUM,REC=2,ERR=99,IOSTAT=IOS) RECTWO

ISKIP = RECONE(37) - 3
        DO 1 I = 1,ISKIP
        READ(NUM,REC=I+2,ERR=99,IOSTAT=IOS) BL
        IJ=(I-1)*512
        DO 2 J = 1,512
        BLOCK(IJ+J) = BL(J)
2       CONTINUE
1       CONTINUE
99      RETURN
        END

C------
C------
C  ROUTINE TO READ BYTE IMAGE DATA
        SUBROUTINE BYTERD(IMAGEK,IMCNT,DAT1,IOS,CHAN)
        BYTE DAT(512)
        BYTE IMAGEK
        INTEGER*4 CHAN
        INTEGER*2 A1(512),IOS

IR = IMCNT
        DO 1 N =1,IMCNT
        DO 2 J = 1,63,8
        READ(CHAN,REC=IR,ERR=99,IOSTAT=IOS)A
```

```
            DO 20 L = 1, 512
                AI(L)=A(L)
20          CONTINUE
            DO 3 I = 1,64
                DATR(I,J,M)   = FLOAT(AI(I))
                DATR(I,J+1,M) = FLOAT(AI(I+64))
                DATR(I,J+2,M) = FLOAT(AI(I+128))
                DATR(I,J+3,M) = FLOAT(AI(I+192))
                DATR(I,J+4,M) = FLOAT(AI(I+256))
                DATR(I,J+5,M) = FLOAT(AI(I+320))
                DATR(I,J+6,M) = FLOAT(AI(I+384))
                DATR(I,J+7,M) = FLOAT(AI(I+448))
3           CONTINUE
            IR = IR +1
2       CONTINUE
1   CONTINUE
99  RETURN
    END
C------------------------------------------------
C----READ INTEGER IMAGE DATA
C
    SUBROUTINE INTRD(IMAGBK,IMGWRT,DATR,IOS,CHAN)
    INTEGER*4 CHAN
    INTEGER*2 A(256),A1(256),IR
    REAL*4 DATR(64,64,120)
    BYTE IMAGBK
    IR = IMAGBK
    DO 1 M = 1,IMGWRT
        DO 2 J = 1,63,8
            READ(CHAN,REC=IR,ERR=99,IOSTAT=IOS) A
            READ(CHAN,REC=IR+1,ERR=99,IOSTAT=IOS) A1
            DO 3 I = 1,64
                DATR(I,J,M)   = FLOAT(A(I))
                DATR(I,J+1,M) = FLOAT(A(I+64))
                DATR(I,J+2,M) = FLOAT(A(I+128))
                DATR(I,J+3,M) = FLOAT(A(I+192))
                DATR(I,J+4,M) = FLOAT(A1(I))
                DATR(I,J+5,M) = FLOAT(A1(I+64))
                DATR(I,J+6,M) = FLOAT(A1(I+128))
                DATR(I,J+7,M) = FLOAT(A1(I+192))
3           CONTINUE
            IR=IR+2
2       CONTINUE
1   CONTINUE
99  RETURN
    END
C------------------------------------------------
C
C
C
C----WRITE NON-IMAGE DATA TO DISK
    SUBROUTINE NIWRITE(RECONE,RECTWO,BLOCK,NUMUSE,IMAGBK,IOS,CHAN)
    BYTE RECONE(512),RECTWO(512),BLOCK(5120),BL(512)
    INTEGER*2 ISKIP,I,J,II,NUMUSE,IOS,IMAGBK
    INTEGER*4 CHAN
C
    WRITE(CHAN,REC=1,ERR=99,IOSTAT=IOS) RECONE
    WRITE(CHAN,REC=2,ERR=99,IOSTAT=IOS) RECTWO
    ISKIP = RECONE(37)
    DO 1 I = 1, (ISKIP-3)
        IJ=(I-1)*512
        DO 2 J =1,512
            BL(J) = BLOCK (J+IJ)
2       CONTINUE
        II = I + 2
        WRITE(CHAN,REC=II,ERR=99,IOSTAT=IOS) BL
1   CONTINUE
99  RETURN
    END

C------------------------------------------------
C----WRITE PROCESSED BYTE DATA TO DISK
    SUBROUTINE BWRITE(DATR,IOS,IMAGBK,IMG,CUTOFF,SCALE,num)
    INTEGER*2 A(512),CUTOFF
    INTEGER*2 I,J,M,II,ims,IOS
    INTEGER*4 num
    BYTE IMAGBK,BA(512)
    REAL*4 SCALE,DATR(64,64,120)
    II = IMAGBK
    DO 1 M = CUTOFF, IMG
```

```
              DO 2 J = 1,63,8
                DO 3 I = 1,64
                  A(I) = IFIX(SCALE*DATR(I,J,M))
                  A(I+64) = IFIX(SCALE*DATR(I,J+1,M))
                  A(I+128) = IFIX(SCALE*DATR(I,J+2,M))
                  A(I+192) = IFIX(SCALE*DATR(I,J+3,M))
                  A(I+256) = IFIX(SCALE*DATR(I,J+4,M))
                  A(I+320) = IFIX(SCALE*DATR(I,J+5,M))
                  A(I+384) = IFIX(SCALE*DATR(I,J+6,M))
                  A(I+448) = IFIX(SCALE*DATR(I,J+7,M))
3               CONTINUE
                DO 5 Z = 1,512
                  if(a(z).gt.127)then
                     a(z) = 127
                  endif
                  BA(Z) = A(Z)
5               continue
                WRITE(num,REC=II,ERR=99,IOSTAT=IOS) BA
                II = II + 1
2             CONTINUE
1           CONTINUE
99        RETURN
          END
C
C
C------------------------------------
C--WRITE INTEGER DATA TO DISK--------
C
          SUBROUTINE IWRITE(DATR,IOS,IMAGBK,IMGWRT,CUTOFF,SCALE,num)

INTEGER*4 num
          INTEGER*2 A(256),A1(256),I,II,IOS,IMGWRT,J,M,IMAGBK,CUTOFF
          REAL*4 SCALE,DATR(64,64,120)
          II = IMAGBK
          DO 1 M = CUTOFF,IMGWRT
            DO 2 J = 1,63,8
              DO 3 I = 1,64
                A(I) = IFIX(SCALE*DATR(I,J,M))
                A(I+64) = IFIX(SCALE*DATR(I,J+1,M))
                A(I+128) = IFIX(SCALE*DATR(I,J+2,M))
                A(I+192) = IFIX(SCALE*DATR(I,J+3,M))
                A1(I) = IFIX(SCALE*DATR(I,J+4,M))
                A1(I+64) = IFIX(SCALE*DATR(I,J+5,M))
                A1(I+128) = IFIX(SCALE*DATR(I,J+6,M))
                A1(I+192) = IFIX(SCALE*DATR(I,J+7,M))
3             CONTINUE
              WRITE(num,REC=II,ERR=99,IOSTAT=IOS)A
              WRITE(num,REC=II+1,ERR=99,IOSTAT=IOS)A1
              II = II + 2
2           CONTINUE
1         CONTINUE
99        RETURN
          END
C
C*******************************************
C******* ROUTINE FOR READING HEADER AND ADMIN. BLOCKS
C*******************************
          SUBROUTINE ADMINRD(REC1,REC2,IOS,CHAN)
          integer*2 num,ios
          INTEGER*4 CHAN
          BYTE REC1(512),REC2(512)

READ(CHAN,REC = 1,IOSTAT = IOS)REC1
          READ(CHAN,REC = 2,IOSTAT = IOS)REC2

RETURN
          END
C*********************************************
C*******ROUTINE TO READ FIRST CURVE FROM CURVE FILE
C**GENERATED BY MICRODELTA*******
C*******
          SUBROUTINE CRVREAD(C1,IOS,CHAN)

REAL*4 C1(128)
          INTEGER*4 CHAN

READ(CHAN,REC = 3,IOSTAT = IOS) C1

RETURN
          END
C************************************************
```

```
C ROUTINE TO READ DATA FILES MADE
C BY INPSUB.FOR **************
C***
      SUBROUTINE DATRD(PLSMPL,TIME,NSMPL,MIN,IOS,CHAN)

REAL*4 PLSMPL(*),TIME(*),MIN
      INTEGER*4 CHAN

READ(CHAN,*,IOSTAT=IOS) NSMPL,MIN
      IF(IOS.NE.0)GOTO 99

READ(CHAN,*,IOSTAT=IOS) (PLSMPL(I), I = 1,NSMPL)
      READ(CHAN,*,IOSTAT=IOS) (TIME(I), I = 1,NSMPL)
C
C
97    RETURN
      END
C************************************************
C** ROUTINE TO WRITE CURVE TO DISK -----------
C****** AND GENERATE A TIME CURVE ---------
C
CX    SUBROUTINE CRVWRT(C1,IOS,NUMIMG,MIN,CHAN)
CX
CX    REAL*4 C1(120),MIN
CX    INTEGER*2 NUMIMG
CX    INTEGER*4 CHAN
C
CX    D = MIN*60/NUMIMG ! DELTA TIME
CX    DO 1 K = 1,NUMIMG
CX    WRITE(CHAN,*,IOSTAT=IOS) K*D,C1(K)
CX1   CONTINUE
CX    RETURN
CX    END
```

```
      SUBROUTINE CHEPOL(P,X,N)
C     **********************
      REAL*4 P(50),X
      INTEGER*2 N
      P(1)=1.
      P(2)=X
      DO 1 I=2,N
1     P(I+1)=2.*X*P(I)-P(I-1)
      RETURN
      END
```

```
        SUBROUTINE DG2(N,X,Y,P,A,B)
C
C
C       Y=A*X+B
C       *******
C
        REAL*4 X(1),Y(1),P(1),A,B
        INTEGER*2 N

H1=0.
        H2=0.
        DO 1 K=1,N
CX      type *,'k,x,y,p ',k,x(k),y(k),p(k)
        V=P(K)
        H1=H1+V
        H2=H2+V*X(K)
1       CONTINUE
        XQ=H2/H1
        H2=0.
        H3=0.
        H4=0.
        DO 2 K=1,N
        V=P(K)
        U=Y(K)
        W=X(K)-XQ
        H2=H2+U*U
        V=V*W
        U=H3+V*U
        H4=H4+V*W
2       CONTINUE
        A=H3/H4
        B=-XQ*A+H2/H1
        RETURN
        END
```

```fortran
      SUBROUTINE ORTH(THETA,PSI,N,L,AL,DX)
C     *********************************
      integer*2 n,L
      DIMENSION THETA(50,300),PSI(50,300),AL(50,50)
C
      L1=L-1
      S=.5*(THETA(1,1)2+THETA(1,L)2)
      DO 1 I=2,L1
1     S=S+THETA(1,I)**2
      S=1./SQRT(S*DX)
      DO 2 I=1,L
      PSI(1,I)=S*THETA(1,I)
2     CONTINUE
      AL(1,1)=S
      DO 3 M=2,N
      M1=M-1
      T=0.
      DO 4 J=1,M1
      S=-.5*(PSI(J,1)*THETA(M,1)+PSI(J,L)*THETA(M,L))
      DO 5 I=2,L1
5     S=S-PSI(J,I)*THETA(M,I)
      H=S*DX
      AL(M,J)=H
4     T=T+H*H
      S=.5*(THETA(M,1)2+THETA(M,L)2)
      DO 6 I=2,L1
6     S=S+THETA(M,I)**2
10    FORMAT(2E12.4,I10)
      W1=S*DX-T
      S=1./SQRT(W1)
      AL(M,M)=S
      DO 7 K=1,M1
      T=0.
      DO 8 J=K,M1
8     T=T+AL(M,J)*AL(J,K)
7     AL(M,K)=S*T
      DO 3 I=1,L
      S=0.
      DO 9 J=1,M
9     S=S+AL(M,J)*THETA(J,I)
      PSI(M,I)=S
3     CONTINUE
      RETURN
      END
```

```
      SUBROUTINE TRADJ(U0,U,PHI,THETA,N,L,DX)
C     *****************************
      integer*2 n,L
      DIMENSION THETA(50,300)
      DIMENSION U(300)
      REAL*4 PHI(50,300)
      L1=L-1
      DO 10 M=1,N
      DO 1 I=1,L1
      S=.5*(U(L-I+1)*PHI(M,L)+U(1)*PHI(M,I))
      I1=I+1
      IF(I1.GT.L1) GOTO 11
      DO 2 J=I1,L1
2     S=S+U(J-I+1)*PHI(M,J)
11    THETA(M,I)=U0*PHI(M,I)+S*DX
102   FORMAT(2I5,2E11.3)
1     CONTINUE
      THETA(M,L)=U0*PHI(M,L)
10    CONTINUE
      RETURN
      END
```

```
C----------------------------------------
C-M003 3*3 SMOOTHING OF A ARRAYSZ*ARRAYSZ ARRAY--------
C----------------------------------------
      SUBROUTINE SMOOTH1(DATR,M)
C
      INTEGER*2 IMGWRT,I,J,M,N
      REAL*4 DATR(64,64,120),TMPDATR(64,64)

NX = 64
      NY = 64
      NI = 50
C
      WF=1/16.
      DO 2 J=2,NY-1
        DO 3 I=2,NX-1
          TMPDATR(I,J) = (4.*DATR(I,J,M) +
     +     2.*(DATR(I+1,J,M)+
     *     DATR(I-1,J,M)+DATR(I,J+1,M)+DATR(I,J-1,M)) +
     *     (DATR(I-1,J-1,M)+DATR(I+1,J-1,M)
     *     +DATR(I+1,J+1,M)+
     *     DATR(I-1,J+1,M)))*WF
3       CONTINUE
2     CONTINUE
C
      DO 22 J=1,NY
        DO 23 I=1,NX
          DATR(NX,NY,M) = TMPDATR(NX,NY)
23      CONTINUE
22    CONTINUE
      RETURN
      END
```

```
C*************************************
C** ROUTINE TO WRITE CURVE TO DISK ----------
C******* AND GENERATE A TIME CURVE ----------
C
C------MODIFICATION 2/26/89 STRITZKE------
C      EXTRACTED FROM ROUTINE.FOR LIBRARY
C-----------------------

SUBROUTINE CRVWRT(X,C1,IOS,NUMIMG,FAK,CHAN)

REAL*4 C1(120),X(120),FAK
       INTEGER*2 numimg
       INTEGER*4 CHAN
C----
       DO 1 K = 1,NUMIMG
       T=X(K)
       CC=C1(K)*FAK            ! IS EQUIVALENT TO CONVERTING
                               ! OUTPUTFUNCTION FROM COUNTS/SEC
                               ! TO COUNTS/MIN
       WRITE(CHAN,*,IOSTAT=IOS) T,CC
1      CONTINUE
       RETURN
       END
```

```
C-----------------------------------
C-- PROGRAM TO FIND MAXIMUM VALUE --------
C-- AND COMPUTE SCALING FACTOR ----------
C-- WRITE MAXIMUM INTO CORNER OF EACH IMAGE---
C-- FOR MOVIE NORMALIZATION
C-----------------------------------
        SUBROUTINE SCALER(DATR,IMGWRT,CUTOFF,FACTOR,SCALE)
        REAL*4 DATR(64,64,120),SCALE,FACTOR,MAX
        INTEGER*2 IMGWRT,CUTOFF
        MAX = 0.
        DO 1 M = CUTOFF,IMGWRT
          DO 2 J = 1,64
            DO 3 K = 1,64
              IF (DATR(K,J,M).GT.MAX) THEN
                MAX = DATR(K,J,M)
              ENDIF
              IF (DATR(K,J,M).LT.0) DATR(K,J,M) = 0
3           CONTINUE
2         CONTINUE
1       CONTINUE
        SCALE=1.E8                    ! MODIFIED STRITZKE
C                                     ! 2/28/89
        DO 1515 J=1,20
          IF(MAX*SCALE.LE.FACTOR) GOTO 1616
          SCALE=SCALE/10.
1515    CONTINUE
1616    CONTINUE
        MAX=MAX
        TYPE *,'MAXIMUM > ',MAX
C------------------------------------
C-- SCALING FACTOR COMPUTED
C-- NORMALIZATION BEGINS
        DO 4 M = CUTOFF,IMGWRT
          DATR(1,1,M) = MAX
          DATR(1,2,M) = MAX
          DATR(2,1,M) = MAX
          DATR(2,2,M) = MAX
4       CONTINUE
        RETURN
        END
```

```
C
C         REGIS_PLOT(Y,RYMAX,RYMIN,NPOINT,IXORIG,IYORIG,JYLEN,INC,INTENS)
C
C              - PLOT GRAPH
C
C
C              Y - REAL*4 VECTOR
C              RYMAX - Y AXIS MAXIMUM
C              RYMIN - Y AXIS MINIMUM
C              NPOINT - NUMBER OF POINTS TO PLOT
C              IXORIG - X AXIS ADDRESS OF GRAPH ORIGIN (0-799)
C              IYORIG - Y AXIS ADDRESS OF GRAPH ORIGIN (0-479)
C              JYLEN - Y AXIS LENGTH (FOR SCALING)
C              INC - X AXIS INCREMENT FOR PLOT
C              INTENS - INTENSITY LEVEL (0-3)
C
C
        SUBROUTINE REGIS_PLOT(Y,RYMAX,RYMIN,NPOINT,IXORIG,IYORIG,
     1  JYLEN,INC,INTENS,IPATRN)
C
        REAL*4 Y(1)
C
        IXPOS=IXORIG
        R=FLOAT(JYLEN)/(RYMAX-RYMIN)
        NO=IYORIG-IFIX((Y(1)-RYMIN)*R)
        CALL REGIS_POS(IXPOS,NO)
C
C
        DO 100 I=1,NPOINT
        IN=I+15
C
        N=IYORIG-IFIX((Y(I)-RYMIN)*R)
C
        CALL REGIS_VECT(IXPOS,N,INTENS,IPATRN)
C
100     IXPOS=IXPOS+INC
C
        CALL REGIS_SYNCH
C
        RETURN
        END
C
```

```
      SUBROUTINE CLEANUP64_2(DAT,NFRAME)
C***** CLEANUP (IE., ZERO) ANY SCATTERED UNSUPPRESSED PIXELS.
C*ZEROED: ANY PIXEL STANDING ALONE OR WITH ONE PIXEL IN 1 OF 4 DIRECTIONS
      IMPLICIT NONE
      INTEGER*2 NUMNONZ,I,J,NUMZEROED,NFRAME,K
      REAL*4 DAT(64,64,120),BUFF(64,64)

DO K=1,NFRAME              ! STEP THROUGH NFRAME IMAGES

DO J=1,64                  ! WRITE K TH IMAGE INTO BUFFER
        DO I=1,64
          BUFF(J,I)=DAT(J,I,K)
        ENDDO ! I
      ENDDO ! J

NUMZEROED = 0              !NUMBER OF PIXELS ZEROED IN FRAME M_OUT
      DO J=1,64
        DO I=1,64
          NUMNONZ = 0            !NUMBER OF NONZERO NEIGHBORS OF THIS PIXEL
          IF (DAT(I,J,K).NE.0) THEN
            IF (DAT(I+1,J,K).NE.0) THEN
              NUMNONZ = NUMNONZ + 1
            ENDIF
            IF (DAT(I-1,J,K).NE.0) THEN
              NUMNONZ = NUMNONZ + 1
            ENDIF
            IF (DAT(I,J+1,K).NE.0) THEN
              NUMNONZ = NUMNONZ + 1
            ENDIF
            IF (DAT(I,J-1,K).NE.0) THEN
              NUMNONZ = NUMNONZ + 1
            ENDIF
            IF (NUMNONZ.LE.1) THEN
              NUMZEROED = NUMZEROED + 1
              BUFF(I,J) = 0                   !ZERO THIS PIXEL
            ENDIF
          ENDIF !IF NONZERO PIXEL
        ENDDO !I=1,64
      ENDDO !J=1,64

WRITE(*,*)NUMZEROED,' PIX CLEANED UP IN FRAME ',K
```

```
        DO J=1,64                    ! WRITE K TH IMAGE BACK
        DO I=1,64
           DAT(J,I,K)=BUFF(J,I)
        ENDDO ! I
        ENDDO ! J

ENDDO ! K       STEPPED THROUGH NFRAME IMAGES
        RETURN
        END
C***************************************************************
```

```
        SUBROUTINE PLOT_C3(NT,XT,U,V1,V2)
C
C       ***********************************************
C       ROUTINE PLOTS 3 CURVES ON VT340
C
C       NT      = NUMBER DATA POINTS
C       XT(NT)  = TIME VECTOR
C       U(NT)   = CURVE 1
C       V1(NT)  = CURVE 2
C       V2(NT)  = CURVE 2
C
C       ***********************************************
C       NT DEFAULT IS INTEGER*4 -- IF NT FROM MAIN IS NOT
C       INTEGER*4,NT MUST BE DECLARED BELOW!
C       ***********************************************
        REAL*4 XT(1),U(1),V1(1),V2(1)
C
C
        W_INPUT=1.E-20
        W1_OUTPUT=1.E-20
        W2_OUTPUT=1.E-20
C
        DO 100 I=1,NT
D       TYPE *,XT(I),U(I),V1(I),V2(I)
        IF(U(I).GT.W_INPUT) W_INPUT=U(I)          ! LOOK
        IF(V1(I).GT.W1_OUTPUT) W1_OUTPUT=V1(I)    ! FOR MAX
        IF(V2(I).GT.W2_OUTPUT) W2_OUTPUT=V2(I)    ! FOR MAX
100     CONTINUE
C
C
        W_MAX=W1_OUTPUT
        IF(W2_OUTPUT.GT.W_MAX) W_MAX=W2_OUTPUT
        IF(W_INPUT.GT.W_MAX) W_MAX=W_INPUT
C
```

```
        CALL REGIS_INIT
        CALL REGIS_ERASE
        CALL REGIS_INTENS(2)      ! RED
C
        IXORIG=100
        IYORIG=400
        IXLEN=500
        IYLEN=350
C
        NTICK=IXLEN/NT
        IXLEN=NT*NTICK
C
        CALL REGIS_AXES(IXORIG,IYORIG,IXLEN,IYLEN)
CC      CALL REGIS_LABEL_X('TIME',IXORIG,IYORIG,IXLEN,XT(NT),0.,5)
CC      CALL REGIS_LABEL_X('TIME',IXORIG,IYORIG,IXLEN,XT(NT-1),XT(1),5)
        CALL REGIS_LABEL_X('TIME',IXORIG,IYORIG,IXLEN,XT(NT),XT(1),5)
        CALL REGIS_LABEL_Y('CPM',IXORIG,IYORIG,IYLEN,W_MAX,0.,5)
        CALL REGIS_INTENS(3)      ! GREEN
        CALL REGIS_PLOT(U,W_MAX,0,NT,IXORIG,IYORIG,IYLEN,NTICK+1,1,1)
        CALL REGIS_INTENS(4)      ! MAGENTA
        CALL REGIS_PLOT(V1,W_MAX,0,NT,IXORIG,IYORIG,IYLEN,NTICK+1,1,1)
        CALL REGIS_INTENS(5)      ! CYAN
        CALL REGIS_PLOT(V2,W_MAX,0,NT,IXORIG,IYORIG,IYLEN,NTICK+1,1,1)
C
        RETURN
        END
```

```
C-----------------------------------------------------------------
C
C       * VT200 TEXT ROUTINES *
C
C              VAX/VMS V4.1 FORTRAN
C
C-----------------------------------------------------------------
C
C       NOTE    THESE ROUTINES USE VT100 (VT200) ESCAPE SEQUENCES
C-----------------------------------------------------------------
C
C       CALL VTINIT
C
C          * THIS ROUTINE MUST BE CALLED FIRST *
C
C          - INITIALIZES VT200 AND MOVES CURSOR HOME (UPPER LEFT)
C          - CLEARS VT200 SCREEN
```

```
C
C------------------------------------------------------------
C
C       CALL VTCLEAR(LINE)
C
C               - CLEARS VT200 FROM LINE TO BOTTOM
C
C
C------------------------------------------------------------
C
C       CALL VTPOS(LINE,ICOL)
C
C               - MOVES CURSOR TO (LINE,ICOL)
C
C               LINE - Y POSITION, 1.(TOP) TO 24.(BOTTOM)
C               ICOL - X POSITION, 1.(LEFT) TO 80.(RIGHT)
C
C
C------------------------------------------------------------
C
C       CALL VTTEXT(LINE,ICOL,TEXT,NUM)
C
C               - MOVES CURSOR TO (LINE,ICOL) AND PRINTS TEXT
C
C               LINE - AS ABOVE
C               ICOL - AS ABOVE
C               TEXT - ASCII TEXT STRING
C               NUM  - NUMBER OF ASCII CHARACTERS IN TEXT TO OUTPUT
C
C
C------------------------------------------------------------
C
C       INTEGER FUNCTION VTGTXT(LINE,ICOL,PROMPT,NUMP,TEXT,NUMT)
C
C               - READ ASCII TEXT STRING WITH PROMPT
C               - MOVES CURSOR TO (LINE,ICOL) AND PRINTS PROMPT
C               - FUNCTION VALUE RETURNS NUMBER OF CHARACTERS READ
C               - <CR>, VTGTXT=0
C               - <CTRL/X>, VTGTXT=-1
C
C               LINE - AS ABOVE
C               ICOL - AS ABOVE
C               PROMPT - ASCII PROMPT STRING
C               NUMP - NUMBER OF ASCII CHARACTERS TO OUTPUT
C               TEXT - ASCII INPUT TEXT STRING
C               NUMT - MAXIMUM NUMBER OF ASCII CHARACTERS INPUT
C
C
C------------------------------------------------------------
C
C       CALL VTNUMB(LINE,ICOL,TEXT,NUM,NUMBER)
C
C               - READS ASCII TEXT AND CONVERTS TO INTEGER
C               - MOVES CURSOR TO (LINE,ICOL) AND PRINTS TEXT
C               - IF <CR> OR ERROR, NUMBER=-999
C
C               LINE - AS ABOVE
C               ICOL - AS ABOVE
C               TEXT - ASCII TEXT STRING
C               NUM  - NUMBER OF ASCII CHARACTERS IN TEXT TO OUTPUT
C               NUMBER - INTEGER NUMBER RETURNED
C
C
C------------------------------------------------------------
C
C       ICHAR=ITTINR()
C
C               - READS ONE ASCII CHARACTER FROM TERMINAL BUFFER
C
C
C------------------------------------------------------------
C
C       CALL PRINT(TEXT)
C
C               - OUTPUTS ASCII TEXT STRING AT CURRENT CURSOR POSITION
C
C
C------------------------------------------------------------
C
        SUBROUTINE VTINIT
C
```

```
        INTEGER*4 SYS$ASSIGN
        INTEGER*2 TT_IN_CHAN,TT_OUT_CHAN
C
        COMMON /VTCOM/ TT_IN_CHAN,TT_OUT_CHAN
C
        CALL SYS$ASSIGN('SYS$INPUT',TT_IN_CHAN,,)
        CALL SYS$ASSIGN('SYS$OUTPUT',TT_OUT_CHAN,,)
        CALL VTCLEAR(1)
C
        RETURN
        END
C
C***************************************************************
C
        SUBROUTINE VTCLEAR(LINE)
C
        BYTE CLR(4)
        DATA CLR/'33','[','J',0/
        CALL VTPOS(LINE,1)
        CALL PRINT(CLR)
        RETURN
        END
C
C***************************************************************
C
        SUBROUTINE VTPOS(LINE,ICOL)
C
        BYTE MOVE(9)
        DATA MOVE/'33','[','0','0',';','0','0','H',0/
C
        MOVE(3)=LINE/10
        MOVE(4)=48+LINE-MOVE(3)*10
        MOVE(3)=MOVE(3)+48
        MOVE(6)=ICOL/10
        MOVE(7)=48+ICOL-MOVE(6)*10
        MOVE(6)=MOVE(6)+48
        CALL PRINT(MOVE)
C
        RETURN
        END
C
C***************************************************************
C
        SUBROUTINE VTTEXT(LINE,ICOL,TEXT,NUM)
C
        BYTE TEXT(1)
C
        CALL VTPOS(LINE,ICOL)
        CALL PRINT(TEXT)
C
        RETURN
        END
C
C***************************************************************
C
        INTEGER FUNCTION VTGTXT(LINE,ICOL,PROMPT,NUMP,TEXT,NUMT)
C
        BYTE PROMPT(1),TEXT(1)
C
        CALL VTTEXT(LINE,ICOL,PROMPT,NUMP)
C
C       I=1
C
10      J=ITTINR(0)
        IF (J.EQ.127) GOTO 15
        IF (J.EQ.24) GOTO 30
        IF (J.EQ.'15) GOTO 20
        IF (J.LT.32) GOTO 10
C
        IF (I.GT.NUMT) GOTO 12
        CALL PRINT(J)
        TEXT(I)=J
        I=I+1
        GOTO 10
C
12      CALL PRINT(7)
        GOTO 10
C
15      I=I-1
        IF (I.EQ.0) GOTO 5
        CALL PRINT(8)
        CALL PRINT(' ')
```

```
        CALL PRINT(8)
        GOTO 10
C
20      VTGTXT=I-1
        GOTO 40
C
30      VTGTXT=-1
C
40      RETURN
        END
C
C*******************************************************************
C
        SUBROUTINE VTNUMB(LINE,ICOL,TEXT,NUM,NUMBER)
C
        CHARACTER*5 TEXT_NUM
        BYTE TEXT(1)
C
        CALL VTTEXT(LINE,ICOL,TEXT,NUM)
C
        READ (5,1) ILEN,TEXT_NUM
1       FORMAT(Q,A5)
C
        IF (ILEN.EQ.0) GOTO 10
        DECODE (ILEN,5,TEXT_NUM,ERR=10) NUMBER
5       FORMAT(I5)
        GOTO 20
C
10      NUMBER=-999
C
20      RETURN
        END
C
C*******************************************************************
C
        INTEGER FUNCTION ITTINR
C
        BYTE CHAR
C
        INTEGER*2 IOSB(4)
        INTEGER*4 SYS$QIOW,MODE
C
        INTEGER*2 TT_IN_CHAN,TT_OUT_CHAN
C
        COMMON /VTCOM/ TT_IN_CHAN,TT_OUT_CHAN
C
        INCLUDE '($IODEF)'
C
        MODE=IO$_READVBLK.OR.IO$M_NOECHO.OR.IO$M_CVTLOW.OR.IO$M_NOFILTR
C
        CALL SYS$QIOW(,%VAL(TT_IN_CHAN),%VAL(MODE)
     1  ,IOSB,,,%REF(CHAR),%VAL(1),,,,)
C
        ITTINR=CHAR
C
        RETURN
        END
C
C*******************************************************************
C
        SUBROUTINE PRINT(TEXT)
C
        INCLUDE '($IODEF)'
C
        INTEGER*2 IOSB(4)
        INTEGER*4 SYS$QIOW,PARAM4
C
        DATA PARAM4/0/
C
        INTEGER*2 TT_IN_CHAN,TT_OUT_CHAN
C
        COMMON /VTCOM/ TT_IN_CHAN,TT_OUT_CHAN
C
        BYTE TEXT(1)
C
        DO 5 I=1,80
5       IF (TEXT(I).LE.0) GOTO 10
        GOTO 20
C
10      L=I-1
        IF (L.LE.0) GOTO 20
```

```
        CALL SYS$QIOW(,%VAL(TT_OUT_CHAN),%VAL(IO$_WRITEVBLK)
    1   ,IOSB,,,%REF(TEXT),%VAL(L),,%VAL(PARAM4),,)
C
20      RETURN
        END
```

```
C**********************************
C**SUB-PROGRAM TO READ AND NORMALIZE CURVES
C**GENERATED FROM MICRODELTA FOR DGF.****
C****************************************
C** BY PETER STRITZKE*****
C*************
        SUBROUTINE CURV_SUB4(NAME,LOC,OPT)
C       *****************************
C
        INCLUDE 'HEAD_CONV.FOR' ! DECLARATIONS AND EQUIV

C       *****************
        CHARACTER NAME*64,DATFL*64,OPT*1
C

REAL*4 C1(128),C11(128),C111(128)       ! HEART CURVE
        REAL*4 C2(128),C22(128) ! AORTIC CURVE
        REAL*4 C(256)                   ! CAN ONLY READ 2 BUFFERS,
                                        ! TOTAL # DATA POINTS =256
C
        REAL*4 X(128),C_OLD(128),P_K(128)
        REAL*4 CBUFF(128)
        REAL*4 FLSMPL(10),TIME(10),NORMFACT,MIN, P_BUFF(20),CBU(128)
        INTEGER*2  STEP, NUM,LOC,IOS
        INTEGER*4 CHAN

BYTE ICHAR
C       ******************

CALL VTINIT
        CALL VTCLEAR(1)

C* OPEN CURVE FILE **
C***** CURVES ARE READ FROM [DELTA.IMAGES]
        TYPE *,'CURV_SUB4.FOR: > '
        WRITE(5,4157) NAME
4157    FORMAT(A)
        CALL LIB$GET_LUN(CHAN)
        OPEN (UNIT=CHAN,FILE=NAME,ACCESS='DIRECT',
    1       STATUS='OLD',RECORDTYPE ='FIXED',IOSTAT=IOS)
```

```
        IF(IOS.NE.0)GOTO 100
C********
C****** READ HEADER INFORMATION
        READ(CHAN,REC=1)RECONE
        READ(CHAN,REC=2)RECTWO

C****** READ CURVE ONE
        READ(CHAN,REC=3)CBUFF     ! HEART
        DO I=1,128
            C(I)=CBUFF(I)
C           TYPE *,I,C(I)
        ENDDO ! I

READ(CHAN,REC=4)CBUFF     ! AORTA
        DO I=128+1,256
            C(I)=CBUFF(I-128)
C           TYPE *,I,C(I)
        ENDDO ! I
        CLOSE (CHAN)
        GNFRM(1)=G1NFRM
        GNFRM(2)=G2NFRM
        GNFRM(3)=G3NFRM
        GFRMR(1)=G1FRMR
        GFRMR(2)=G2FRMR
        GFRMR(3)=G3FRMR
        GGPAU(1)=G1GPAU
        GGPAU(2)=G2GPAU
        GGPAU(3)=0.
        TOTFRM=G1NFRM+G2NFRM+G3NFRM
C
C       TYPE *,TOTGP,TOTFRM
        T=0.
        NFR=0
        DO I=1,TOTGP
            DO J=1,GNFRM(I)
                NFR=NFR+1
                T=T+GFRMR(I)
                X(NFR)=T/60.                    ! TIME IN MINUTES
                C1(NFR)=60.*C(NFR)/GFRMR(I)! COUNTS/MIN
                C2(NFR)=60.*C(NFR+TOTFRM)/GFRMR(I)! COUNTS/MIN
                C11(NFR)=C1(NFR)
                C22(NFR)=C2(NFR)
D               TYPE *,NFR,C1(NFR),C2(NFR)
            ENDDO ! J
            X(NFR)=X(NFR)+GGPAU(I)
        ENDDO ! I
C
        NT=TOTFRM                       ! IMPORTANT
C********
        TYPE *,' ENTER RANGE IN TIME FOR FIT'
        WRITE(5,44)
44      FORMAT(' IMAGE NUMBER 1 > ',$)
        READ(5,46)NT1
46      FORMAT(I)
        WRITE(5,45)
45      FORMAT(' TIME POINT 2 > ',$)
        READ(5,46)NT2

SU1=0.
        SU2=0.
        DO I=NT1,NT2
            SU1=SU1+C1(I)
            SU2=SU2+C2(I)
        ENDDO ! I
        SU1=SU1/(NT2-NT1+1)
        SU2=SU2/(NT2-NT1+1)

DO I=1,NT
            C1(I)=C1(I)*SU2/SU1
        ENDDO ! I
        N2=(NT1+NT2)/2
        DO I=1,N2
            C1(I)=C2(I)
        ENDDO ! I
D       TYPE *,' NO    TIME           HEART         AORTA         NEW'
        DO I=1,NT
            C(I)=C1(I)
            WRITE(5,47)I,X(I),C1(I),C2(I),C(I)
47          FORMAT(I3,E13.2,3F14.2)
```

```
              ENDDO ! I
              CALL PLOT_C3(NT,X,C11,C22,C)
              ICHAR=ITTINR()
              CALL VTCLEAR(1)

C*******************
C****** READ DATA GENERATED BY INPSUB
C***** FOR NORMALIZATION OF BLOOD-POOL CURVE
C****************
              DATFL = NAME(1:LOG)//'DTA'
              CALL LIB$GET_LUN(CHAN)
              OPEN(UNIT=CHAN,FILE=DATFL,STATUS='OLD',IOSTAT=IOS)
              IF(IOS.NE.0)GOTO103
C**
              CALL DATRD(PLSMPL,TIME,NSMPL,MIN,IOS,CHAN)
              IF(IOS.NE.0)GOTO 104
              CLOSE(CHAN)
C-----------------------
C--- NORMALIZE THE CURVE TO FIRST PLASMA SAMPLE--
C-----------------------
C
C
C                                                !
              DO 1515 I=1,TOTFRM  ! FIND TIME POINT FOR NORMALIZATION
              IF(X(I).GE.TIME(1)) GOTO 1516
1515          CONTINUE      !
              TYPE *,' NO NORMALIZATION PERFORMED!
              CALL PLOT_C3(NT,X,C,C,C)
              ICHAR=ITTINR()
              CALL VTCLEAR(1)
              GOTO 2728
1516          CONTINUE
              IF1=I                   ! TIME POINT FOR NORMALIZATION
              FAK=PLSMPL(1)/C1(IF1)   ! # SAMPLES = 1
              DO 1517 J=1,TOTFRM
              W1=C1(J)*FAK   ! NORMALIZE INPUT FKT DONE
D             TYPE *,'OLD,NEW',J,X(J),C1(J),W1
              C1(J)=W1
1517          CONTINUE
C
              IF(NSMPL.EQ.1) GOTO 2728       ! NP # NUMBER PLASMA SAMPLES =1
C
C
              DO 2737 I=1,TOTFRM  ! SET WEIGHTS TO 1.
              C_OLD(I)=C1(I)       ! SAVE OLD CURVE FOR GRAPH
2737          P_K(I)=1.           ! WEIGHTS
              DO 2738 I=1,NSMPL    ! LOGARITHMM PLASMA VALUES
D             type *,'plasma i time plasma wei ',i,TIME(i),PLSMPL(i),p_k(i)
2738          P_BUFF(I)=ALOG(PLSMPL(I))
C
C
              CALL DG2(NSMPL,TIME,P_BUFF,P_K,AA,BB)  ! Y= AA * X + BB
              BB=EXP(BB)       !
C
C
              DO 2739 I=IF1,TOTFRM    ! REPLACE OLD CURVE BY NEW PLASMA
              C1(I)=BB*EXP(AA*X(I))   ! VALUES FOR TIMES LATE
D             TYPE *,'T,U,K',I,X(I),C_OLD(I),C1(I)
2739          CONTINUE
C
CX            QMIN=-1.E20
CX            DO 4900 I=1,TOTFRM      ! LOOK FOR MAXIMUM
CX            IF(C1(I).GT.QMIN)GOTO 4901
CX            GOTO 4900
CX4901        KMAX=I
CX4900        CONTINUE
CX
CX            DO 4903 J=1,2
CX            DO 4902 I=KMAX+2,TOTFRM-2
CX            CBU(I)=(-6.*C1(I-2)+24.*C1(I-1)+34.*C1(I)+24.*C1(I+1)-6.*C1(I+2))/70.
CX4902        CONTINUE
CX
CX            DO 2749 I=KMAX+2,TOTFRM-2       ! CREATE PLASMA CURVEC
CX            W=-6.*CBU(I-2)+24.*CBU(I-1)+34.*CBU(I)+24.*CBU(I+1)-6.*CBU(I+2)
CX2749        C1(I)=W/70.
CX4903        CONTINUE
C
              DO 2740 I=1,TOTFRM      ! CREATE PLASMA CURVE
2740          CBUFF(I)=BB*EXP(AA*X(I))  ! FOR GRAPH
```

```
C
        NT=IOTERM                    ! IMPORTANT
        CALL PLOT_C3(NT,X,C_OLD,CBUFF,C1)
        ICHAR=ITTINR()
C
        CALL VTCLEAR(1)

2728    CONTINUE        ! # SAMPLES >=1  DONE
C
        CALL VTCLEAR(1)
        WRITE(5,8819)
8819    FORMAT(' ARTIFICIAL DECAY (HIPPURAN) Y/N ',$)
        ICHAR=ITTINR()
        IF(ICHAR.EQ.'Y') THEN
8812      WRITE(5,8818)
8818      FORMAT(' START WITH FRAME NR [I]',$)
          READ(5,8817)NST
8817      FORMAT(I)
          WRITE(5,8816)
8816      FORMAT(' THALF IN MINUTES [F] ',$)
          READ(5,8814)THALF
8814      FORMAT(F)

DO I=1,NT
            C111(I)=C1(I)
          ENDDO ! I
          DO I=NST,NT
            C111(I)=C1(I)*EXP(-0.693*X(I)/THALF)
          ENDDO ! I
          CALL PLOT_C3(NT,X,C1,C1,C111)
          ICHAR=ITTINR()
          CALL VTCLEAR(1)

IF(ICHAR.EQ.'B') THEN
            GOTO 8812
          ENDIF

DO I=1,NT
            C1(I)=C111(I)
          ENDDO ! I

ENDIF

C-----------------------------------------------------
C--- WRITE CURVE TO DISK IN 'NAME'.CRV -----
C-----------------------------------------------------
2000    CALL LIB$GET_LUN(CHAN)
        OPEN(UNIT=CHAN,FILE=NAME(1:LOC)//'CRV',STATUS='NEW',IOSTAT=IOS)
        IF(IOSTAT.NE.0)GOTO 105
        FAK=GFRMR(1)/60.              ! DO NOT CONVERT TIME VECTOR
                                      ! TO MINUTES
        TYPE *,'FACTOR CORRECT IMAGE COUNTS > ',FAK
        CALL CRVWRT(X,C1,IOSTAT,NT,FAK,CHAN)
        IF(IOSTAT.NE.0)GOTO 106
        CLOSE(CHAN)
        GOTO 1988
C-----------------------------------------------------
C--- ERROR MESSAGES ----------------------------------
C-----------------------------------------------------
100     WRITE(*,*)'ERROR OPENING MICRODELTA CURVE FILE'
        GOTO 1987
101     WRITE(*,*)'ERROR READING NON-CURVE DATA'
        GOTO 1987
102     WRITE(*,*)'ERROR READING CURVE DATA'
        GOTO 1987
103     WRITE(*,*)'ERROR OPENING DATA FILE FOR NORMALIZATION'
        GOTO 1987
104     WRITE(*,*)'ERROR READING DATA FILE FOR NORMALIZATION'
        GOTO 1987
105     WRITE(*,*)'ERROR OPENING OUPUT FILE'
        GOTO 1987
106     WRITE(*,*)'ERROR WRITNG OUTPUT FILE'
        GOTO 1987
1987    WRITE(*,*)'THE ERROR NUMBER IS',IOS
1988    RETURN
        END
```

```
        SUBROUTINE MAIN_SUB1(name,iname,LOC)

IMPLICIT NONE

CCC     VARIABLE DECLARATIONS
        CHARACTER iname*64,name*64,OPT2*1
        character*40 afile,bfile INTEGER*2 MODE,IOSTAT,CUTOFF,OPTION,NUMPOLY,MAXIMG
        INTEGER*2 IISPAC,IMGWRT,TOTBLK,IMAGBK,IMG,IFLAG,PROCOPT
        INTEGER*2 I,J,M,NK,NT,ISCALE,counter,NUMUSE,LOC,K,NFIT,NDEL
        INTEGER*2 NXL,NXR,NYB,NYT
        INTEGER*4 CHAN
        REAL*4 U(120),XT(120),V(120),SCALE,Q(120),DT,DATR(64,64,120)
        REAL*4 THETA(50,300),PSI(50,300),Y(120),MAX,RESULT(64,64,5)
        REAL*4 FACT,W(120),W1,XX(5),YY(5),PP(5),AK,BK,BUFF(64,64),DX
        BYTE RECONE(512),RECTWO(512)
        BYTE BLOCK(5120),VNUM(2),PATNAM(18),PATNUM(6)
        BYTE ACQ(10),IMGTYP,DAT(9),EXT(3),STUDY(10)
        BYTE TAPID(8),ANSWER,ANS EQUIVALENCE (PATNAM(1),RECONE(177)),(PATNUM(1),RECONE(195))
        EQUIVALENCE (ACQ(1),RECONE(211)),(IMGTYP,RECONE(239))
        EQUIVALENCE (STUDY(1),RECTWO(42)),(EXT(1),RECONE(254))
        EQUIVALENCE (IMGWRT,RECONE(39)),(IMAGBK,RECONE(37))
        EQUIVALENCE (IISPAC,RECONE(9)),(TOTBLK,RECONE(3))
        EQUIVALENCE (DAT(1),RECONE(236)),(EXT(1),RECONE(254))
        EQUIVALENCE (VNUM(1),RECONE(236)),(MAXIMG,RECONE(13))
        EQUIVALENCE (MODE,RECTWO(123))
C-----------------------------------------------------------------C
C       CALL LIB$GET_LUN(CHAN)
C       AFILE = '[ANALYSIS]'//INAME
        OPEN(UNIT=CHAN,FILE=INAME,STATUS='OLD',ACCESS='DIRECT',
     1       RECORDTYPE='FIXED',ERR=100)

CCCCC   READ NON-IMAGE BLOCKS
        CALL HEADRD(RECONE,RECTWO,BLOCK,IOSTAT,CHAN)
        IF (IOSTAT.NE.0) GOTO 105
C
C
CCC     DISPLAY HEADER INFORMATION FOR APPROVAL
        WRITE(*,2)PATNAM,PATNUM,EXT,DAT,ACQ,VNUM,IMGTYP,STUDY,TAPID
2       FORMAT(' PATIENT NAME-',18A1/' UNIT NUMBER-',6A1,'.X',3A1/
```

```
     1     ' DATE-',9A1/' ACQUISITION PROTOCOL-',10A1/' VIEW-',2A1/
     2     ' MATRIX TYPE-',A1/' STUDY TYPE-',10A1/' VIEW-',2A1/
     3     ' TAPE ID NUMBER-',8A1//)
           WRITE(*,3) IMGWRT,IMAGBK,IISPAC,TOTBLK
   3       FORMAT(' NUMBER OF IMAGES:         ',I6/
     1     ' START BLOCK OF IMAGE 1:          ',I6/
     2     ' IMAGE-IMAGE SPACE:               ',I6/
     3     ' TOTAL NUMBER OF BLOCKS:          ',I6//)
C
C
C
CCC   READ IMAGE BLOCKS(EITHER BYTE OR INTEGER)
           write(*,*)'THERE ARE ',IMGWRT,' IMAGES.'
           write(*,*)'DO YOU WANT TO USE THEM ALL?'
           READ(*,15)OPT2
           IF (OPT2.EQ.'N'.OR.OPT2.EQ.'n') THEN
                 WRITE(*,*)'ENTER HOW MANY IMAGES TO PROCESS'
                 READ(*,*)IMGWRT
           ENDIF
  15       FORMAT(A1)

IF (MODE.EQ.1)THEN

CALL BYTERD(IMAGBK,IMGWRT,DATR,IOSTAT,CHAN)
           ELSEIF (MODE.EQ.2)THEN
                 CALL INTRD(IMAGBK,IMGWRT,DATR,IOSTAT,CHAN)
           ELSE
                 IOSTAT = 1
           ENDIF
           IF (IOSTAT.NE.0)GOTO107
           CLOSE(CHAN)
           CALL LIB$GET_LUN(CHAN)

open(unit=CHAN,file=name(1:LOC)//'CRV',status='old')
C-------------------------------
CCC   PROCESS IMAGES (EITHER BYTE OF INTEGER)
CCC   read input and time vectors from disk ******
           DO 1000 I = 1,imgwrt
           read(CHAN,*)xt(I),u(I) !XT is time vector, U is input functION
           type *,' main read i,xt,u',i,xt(i),u(i)
 1000      CONTINUE
           close(CHAN)
C------------------------------------------------C
C== decide whether to do a deconvolution or load a study ==c
CCC decide on lag time and number of polynomials*******
           WRITE(*,*)'ENTER THE NUMBER OF POLYNOMIALS'
           READ(*,*)NUMPOLY
           WRITE(*,*)'ENTER A [0] TO USE ALL OF DATA'
           WRITE(*,*)'A [1] TO MANUALLY ENTER THE LAG TIME'
           WRITE(*,*)'A [2] TO CUTOFF UNTILL INPUT MAXIMUM'
           READ(*,*)OPTION
           IF(OPTION.EQ.1.OR.OPTION.EQ.2)THEN
                 CALL LAGTIME(XT,U,IMGWRT,OPTION,CUTOFF)
C-- WRITE NEW INPUT AND TIME VECTOR TO DISK --C
CC               CALL LIB$GET_LUN(CHAN)
CC               OPEN(UNIT=CHAN,FILE=NAME(1:LOC)//'CRV',STATUS='OLD')
CC               TYPE *,'OPTION [1-2]'
                 DO 1001 I = 1,IMGWRT-CUTOFF+1
                       TYPE *,'I,XT,U',I,XT(I),U(I)
CC                     WRITE(CHAN,*)XT(I),U(I)
 1001            CONTINUE
CC               CLOSE(CHAN)
           ENDIF
CCC -----------------------------
CCC === RESET NUMBER OF IMAGE PARAMETERS ===
CCC-- DEPENDING ON LAG TIME ---------
CCC ----- NUMUSE = NUMBER OF IMAGES USED ---
C------------------------------
           IF(OPTION.EQ.1.OR.OPTION.EQ.2) THEN
                 NUMUSE = IMGWRT - CUTOFF + 1
                 IMGWRT = NUMUSE
           ELSE
                 CUTOFF = 1
                 NUMUSE = IMGWRT
                 TYPE *,'OPTION [0]'
                 DO 5001 I = 1,IMGWRT
                       TYPE *,'I,XT,U',I,XT(I),U(I)
 5001            CONTINUE
           ENDIF
           WRITE(*,*)'DELAY INPUT FUNCTION Y/N ?'
           READ(5,8812)ANSWER
```

```
8812    FORMAT(A)
        IF(ANSWER.EQ.'Y') THEN
            WRITE(*,*)' NUMBER IMAGES TO BE DELAYED [I] >'
            READ(5,8813)NDEL
8813        FORMAT(I)
            DO I=1,IMGWRT
                Q(I)=0.
            ENDDO ! I

DO I=NDEL,IMGWRT
                Q(I)=XT(I-NDEL+1)
            ENDDO ! I
            TYPE *,'DELAY TIME AXIS'
            DO I=1,IMGWRT
                TYPE *,'I,TIME OLD, NEW',I,XT(I),Q(I)
                XT(I)=Q(I)
            ENDDO ! I
        ENDIF
C****************
CC**Call output independant dop
C****************
        TYPE *,'NUMUSE ',NUMUSE WRITE(5,816)
816     FORMAT(' MASK IMAGES Y/N > ',$)
        READ(5,817) ANS
817     FORMAT(A)
        IF(ANS.EQ.'Y') THEN
            WRITE(5,814)
814         FORMAT('Xleft,Xright,Ybottom,Ytop >',$)
            READ(5,815)NXL,NXR,NYB,NYT
815         FORMAT(4I4)
            DO I=1,64
                DO J=1,64
                    BUFF(I,J)=0.
                ENDDO ! J
            ENDDO ! I DO I=NXL,NXR
                DO J=NYB,NYT
                    BUFF(I,J)=1.
                ENDDO ! J
            ENDDO ! I DO M=1,IMGWRT
                DO I=1,64
                    DO J=1,64
                        DATR(I,J,M)=DATR(I,J,M)*BUFF(I,J)
                    ENDDO ! J
                ENDDO ! I
            ENDDO ! M
        ENDIF
        WRITE(5,712)
712     FORMAT(' CALCULATE h or H [h,H] > ',$)
        READ(5,8812)ANSWER
        IF(ANSWER.EQ.'H') THEN
            DO I=1,64
                DO J=1,64
                    BUFF(I,J)=0.
                ENDDO ! J
            ENDDO ! I DX=XT(2)-XT(1)
            TYPE *,'DX = ',DX
            DO M=1,IMGWRT
                TYPE *,'INT ',M
                DO I=1,64
                    DO J=1,64
                        BUFF(I,J)=BUFF(I,J) + DATR(I,J,M)*DX
                        DATR(I,J,M)=BUFF(I,J)
                    ENDDO ! J
                ENDDO ! I
            ENDDO ! M
        ENDIF CALL CLEANUP64_2(DATR,IMGWRT)
CCC     DO 145 M=1,IMGWRT
CCC     TYPE *,' SMOOTH > ',M
CCC145   CALL SMOOTH1(DATR,M)

CALL INFDOP(NUMUSE,NUMPOLY,XT,U,DT,THETA,PSI)
```

```
C*************************
C*** WRITE EACH OUTPUT VECTOR INTO A  REAL ELEMENT ARRAY
C* CHECK IF MAX IS 0 AND IF SO SKIP REST OF PROCESSING ON THAT ARRAY
C*************************
        TYPE *,'CUTOFF,IMGWRT ',CUTOFF,IMGWRT
C
        DO 18 I = 1,64
        DO 19 J = 1,64
            MAX = 0.
C           DO 20 M = CUTOFF, IMGWRT
            DO 20 M = 1, IMGWRT        ! STRITZKE 2/2/89
                V(M) = DATR(I,J,CUTOFF+M-1)     !  * *
                IF(V(M).GT.MAX)THEN
                    MAX = V(M)
                ENDIF
20          CONTINUE
C*************************
C*** HECK IF VECTOR IS ZERO AND IF SO
C*SKIP PROCESSING **
C*************************
            IF (MAX.EQ.0.)GOTO19
C-------------------------------------
C-- CONDITION DATA BEFORE PROCESSING 5-POINT SMOOTH--------
CCCCC       CALL SMOOTHER(V,W,NUMUSE)         ! V(I)-->W(I)
C---------- CALL OUTPUT DEPENDANT DOP
CCCCC       CALL OUTDOP(NUMUSE,NUMPOLY,DT,THETA,PSI,W,Y)
            CALL OUTDOP(NUMUSE,NUMPOLY,DT,THETA,PSI,V,Y)
C---- CALL 5 POINT SMOOTHING ROUTNE ON RESULT OF DOP------
CCCCC       CALL SMOOTHER(Y,Q,NUMUSE)
C--- WRITE DATA BACK INTO IMAGE ARRAY -------------
            DO 21 M = 1,IMGWRT
CCCCC           DATR(I,J,M) = Q(M)
                DATR(I,J,M) = Y(M)
21          CONTINUE
19      CONTINUE
        WRITE(*,*)I
18      CONTINUE

IMGWRT=IMGWRT-5       ! CUT OFF LAST IMAGES

CALL CLEANUP64_2(DATR,IMGWRT)

C---------------------------------
C-- CALL SCALER TO FIND FACTOR TO ALLOW DATA TO BE
C-- WRITTEN AS SIGNED BYTES OR INTEGERS TO DISK
C-- DIFFERENT SCALING DEPENDING ON BYTE OR WORD MODE
        IF (MODE.EQ.1)THEN
            FACT = 127.
        ELSE
            FACT = 5000.      ! STRITZKE 2/4/89
C           FACT = 32000.
        ENDIF

CALL SCALER(DATR,IMGWRT+1,FACT,SCALE) ! STRITZKE 2/2/89

C------ PROCESSING OVER, BEGIN WRITING STUDY TO MICRODELTA --
        CALL LIB$GET_LUN(CHAN)
CC      bfile = '[delta.images]'//name(1:LOC)//'X50'
        bfile = name(1:LOC)//'X50'
        OPEN(UNIT=CHAN,FILE=bfile,STATUS='NEW',RECL=128,
1       RECORDTYPE='FIXED',ACCESS='DIRECT',ERR=110)

CCC     WRITE NON-IMAGE BLOCK TO DISK
CCC     RESET HEADER/ADMIN BLOCK VARIABLES
CCC     TO REFLECT CHANGE IN NUMBER OF FRAMES
CCC
        IMG = IMGWRT
        NUMUSE=IMGWRT
        TYPE *,'STORE FINALLY',IMG,' IMAGES'
        RECTWO(125) = NUMUSE
        RECTWO(129) = NUMUSE
        IF(MODE.EQ.1) THEN
            TOTBLK = (NUMUSE*8) + (IMAGBK - 1)
        ELSE
            TOTBLK = (NUMUSE*16) + (IMAGBK - 1)
            TYPE *,'WRITE ',TOTBLK,' BLOCKS'
        ENDIF
        MAXIMG = NUMUSE
        CALL NIWRITE(RECONE,RECTWO,BLOCK,NUMUSE,IMAGBK,IOSTAT,CHAN)
        IF (IOSTAT.NE.0)GOTO115
```

```
CCCC    WRITE IMAGE DATA TO DISK
        IF (MODE.EQ.1) THEN
            TYPE *,'IMAGE SCALING FACTOR > ',SCALE
            CALL BWRITE(DATR,IOSTAT,IMAGBK,IMG,1,SCALE,CHAN)
        ELSE
            TYPE *,'START IMAGES AT BLOCK ',IMAGBK
            TYPE *,'WRITE ',IMG,' IMAGES'
            TYPE *,'IMAGE SCALING FACTOR > ',SCALE
            CALL IWRITE(DATR,IOSTAT,IMAGBK,IMG,1,SCALE,CHAN)
        ENDIF
        IF(IOSTAT.NE.0)GOTO1988
        CLOSE(CHAN)
C---------------------------------------------
C---IMAGES HAVE BEEN WRITTEN C
C----------------------------------------------C
C-- FUNCTIONAL IMAGES WRITTEN DATA TO DISK ---------------C
        GOTO1988
CCCC    ERROR MESSAGES
100     WRITE(*,*)'ERROR OPENING INPUT FILE'
        GOTO 1988
105     WRITE(*,*)'ERROR READING NON-IMAGE BLOCKS'
        WRITE(*,*)'THE ERROR IS ',IOSTAT
        GOTO1988
107     WRITE(*,*)'ERROR READING IMAGE BLOCKS'
        WRITE(*,*)'ERROR IS ',IOSTAT
        GOTO1988
110     WRITE(*,*)'ERROR OPENING OUTPUT FILE'
        GOTO 1988
115     WRITE(*,*)'ERROR WRITING TO OUPUT FILE'
        WRITE(*,*)'THE ERROR IS ',IOSTAT
        GOTO1988

1988    return
        END
```

```
C---------------------------------------------
C----- ROUTINES FOR PROCESSING DOP DATA
C---------------------------------------------
C
        subroutine INPDOP(NT,NK,XT,U,DT,THETA,PSI)
C       ***********************************
```

```
C
C       ROUTINE TO CALCULATE INPUT DEPENDANT CONVOLUTION
C
C       *****************************
C
C       MODEL: NONE
C
C       NK      = NUMBER POLYNOMIALS
C       NT      = max 300
C       XT(NT)  = Time
C       V(X,Y,NT)= Output         (V1,V2)
C       U(NT)   = Input
C       Y(NT)   = RESULT h(t) OR H((t)
C
C
        REAL*4 THETA(50,300),PSI(50,300),AL(50,50)
        REAL*4 U(120),XT(120),F(50)
C
        REAL*4 PHI(50,300),DNT,TT,SU,W1
        INTEGER*2 NK,NT
C
        U0=U(1)
        DNT=2./FLOAT(NT-1)                  ! TEST O.K.
C
        TT0=XT(1)
        DT=XT(2)-TT0
        TT=-1.
C
        DO 2 I=1,NT
        CALL CHEPOL(F,TT,NK)
            DO 3 J=1,NK
3               PHI(J,I)=F(J)
            TT=TT+DNT
2       CONTINUE
C
        CALL TRADJ(U0,U,PHI,THETA,NK,NT,DT)
        CALL ORTH(THETA,PSI,NK,NT,AL,DT)
            DO 4 I=1,NT
                DO 41 J=1,NK
                    THETA(J,I)=0.
                    DO 41 K=1,J
                        THETA(J,I)=THETA(J,I)+AL(J,K)*PHI(K,I)
41              CONTINUE
4       CONTINUE
C       open(UNIT=10,FILE='POLY.DAT',STATUS='NEW')
C       WRITE(10,*)DT
C       DO 10 I = 0,120,30
C       WRITE(10,*)(F(J+I),J=1,30)
C10     CONTINUE
C       DO 11 I =1,50
C           DO 12 J=1,300
C           WRITE(10,*)THETA(I,J),PSI(I,J)
C12         CONTINUE
C11     CONTINUE
        RETURN
        END
C------------------------------------------
C------------ ROUTINE TO CALCULATE THE
C------ OUTPUT CURVE DEPENDANT PART OF DOP
C       USE IN CONJUNCTION WITH INDOP
C------------------------------------------
        SUBROUTINE OUTDOP(NT,NK,DT,THETA,PSI,V,Y)

REAL*4 THETA(50,300),PSI(50,300),V(120)
        REAL*4 F(50),Y(120),DT
        integer*2 nt,nk DO 5 J=1,NK
        F(J)=.5*(THETA(J,1)*V(1)+THETA(J,NT)*V(NT))
            DO 6 I=2,NT-1
                F(J)=F(J)+THETA(J,I)*U(I)
6           CONTINUE
        F(J)=F(J)*DT
5       CONTINUE
C
        DO 857 I=1,NT
        Y(I) = 0.
        DO 7 J=1,NK
7           Y(I)=Y(I)+F(J)*PSI(J,I)
```

```
857       CONTINUE
C
          RETURN
          END
C-------------------------------------------
C------ SUBPROGRAM TO PERFORM A -------
C------ FIVE POINT SMOOTH -------------
C------ FIRST TWO POINTS ARE SET TO THE THIRD VALUE ---
C------ LAS TWO POINTS SET TO THIRD TO LAST VALUE -----
C-------------------------------------------
          SUBROUTINE SMOOTHER(V,Y,IMGWRT)

REAL*4  V(120),Y(120)
          INTEGER*2 IMGWRT
          DO 1 I = 3,(IMGWRT-2)
          Y(I) = 1./70.*(-6.*V(I-2)+24.*V(I-1)+36.*V(I)+24.
     1    *V(I+1)-6.*V(I+2))
 1        CONTINUE
          Y(1) = Y(3)
          Y(2) = Y(3)
          Y(IMGWRT) = Y(IMGWRT-2)
          Y(IMGWRT-1) = Y(IMGWRT-2)
          RETURN
          END
C-------------------------------------------
C-- PROGRAM TO FIND MAXIMUM VALUE --------
C-- AND COMPUTE SCALING FACTOR ----------
C-- WRITE MAXIMUM INTO CORNER OF EACH IMAGE ---
C-- FOR MOVIE NORMALIZATION --------------
C------
CX        SUBROUTINE SCALER(DATR,IMGWRT,CUTOFF,FACTOR,SCALE)
CX        REAL*4 DATR(64,64,120),SCALE,FACTOR,MAX
CX        INTEGER*2 IMGWRT,CUTOFF
CX        MAX = 0.
CX        DO 1 M = CUTOFF,IMGWRT
CX          DO 2 J = 1,64
CX          DO 3 K = 1,64
CX          IF (DATR(K,J,M).GT.MAX) THEN
CX              MAX = DATR(K,J,M)
CX          ENDIF
CX          IF (DATR(K,J,M).LT.0) DATR(K,J,M) = 0
CX3         CONTINUE
CX2       CONTINUE
CX1       CONTINUE
CX        SCALE=1.E8                     ! MODIFIED STRITZKE
C                                        ! 2/28/89
CX            DO 1515 J=1,20
CX            IF(MAX*SCALE.LE.FACTOR) GOTO 1616
CX1515         SCALE=SCALE/10.
CX1616     CONTINUE
CX        MAX=MAX*SCALE
C-------------------------------------------
C--- SCALING FACTOR COMPUTED
C--- NORMALIZATION BEGINS
CX        DO 4 M = CUTOFF,IMGWRT
CX        DATR(1,1,M) = MAX
CX        DATR(1,2,M) = MAX
CX        DATR(2,1,M) = MAX
CX        DATR(2,2,M) = MAX
CX4       CONTINUE
CX        RETURN
CX        END
C
C-------------------------------------------
C - ROUTINE TO CORRECT FOR LAGTIME ----------
C--- EITHER MANUAL OR AUTOMATIC TO MAX -------
C--- OPTION = 1 MANUAL --------------------
C--- OPTION = 2 TO MAX --------------------
C-------------------------------------------
          SUBROUTINE LAGTIME(XT,U,IMGWRT,OPTION,CUTOFF)
C
          INTEGER*2 OPTION,IMGWRT,CUTOFF,DELTIME
          REAL*4 U(120),MAX,XT(120),XT1(120),U1(120)
C
          IF(OPTION.EQ.1) THEN
            WRITE(*,*)'ENTER THE FRAME TO BEGIN STUDY WITH'
            READ(*,*) CUTOFF
          ELSE
            MAX = 0.
            DO 1 I = 1,IMGWRT
            IF(U(I).GT.MAX)THEN
```

```
                  MAX = U(I)
                  CUTOFF = I
              ENDIF
1         CONTINUE
       ENDIF
       DO 2 I = CUTOFF , IMGWRT
          U1(i) = U(I)
          XT1(i) = XT(I)
2      CONTINUE
       DO 3 I = 1, IMGWRT-CUTOFF+1              ! STRITZKE 2/2/89
          U(I) = U1(I+CUTOFF-1)
          XT(I) = XT1(I+CUTOFF-1)
3      CONTINUE
       RETURN
       END
C---------------------------------------------------------------C
C------- ROUTINE TO GENERATE FUNCTIONAL IMAGES -----------------C
C------- OF MEAN TRANSIT TIME ON REAL ARRAYS -------------------C
C------- STUDIES MUST BE 64x64 AND CONSIST OF ------------------C
C------- NO MORE THAN 120 IMAGES -------------------------------C
C---------------------------------------------------------------C
C--- DATR = IMAGE DATA, IMGWRT = # OF IMAGES, XT = TIME VECTOR
       SUBROUTINE FUNCTIONAL(DATR,IMGWRT,XT,RESULT,NORM)
       REAL*4 SUM1,SUM2,RESULT(64,64,5),MAX,CUTOFF,MAX2
       REAL*4 DATR(64,64,120),XT(120),U(120)
       INTEGER*2 IMGWRT,Q,NORM
       CHARACTER*1 ROUND
C
       WRITE(*,*)'SHOULD NUMBERS BE SCALED UP BY A HUNDRED'
       WRITE(*,*)'TO AVOID LOSS OF DATA FROM ROUNDOFF.'
       READ(*,15) ROUND
15     FORMAT(A)
       MAX = 0.
       MAX2 = 0.
       Q = 0   !will keep count of any overflows
       DELTIME = XT(2) - XT(1)
C--------------------------------------------------C
CC-- CONDITION DATA,SET POINTS BELOW 5% OF MAX TO 0
       MAX2 = datr(1,1,1)
       CUTOFF = .04*MAX2
       DO 8 I = 1, 64
          DO 9 J = 1, 64
             DO 10 M = 1, IMGWRT - 5
                IF(DATR(I,J,M).LE.CUTOFF)DATR(I,J,M)=0.
10           CONTINUE
9         CONTINUE
8      CONTINUE
C--------------------------------------------------C
C-- BEGIN THE PROCESSING DO LOOPS
C--------------------------------------------------C
C-- WRITE A REAL ELEMENT VECTOR FOR EACH PIXEL----C
       DO 1 I = 1,64
          DO 2 J = 1,64
             MAX = 0
             DO 3 K = 1,IMGWRT - 5
                IF(DATR(I,J,1).GT.MAX)THEN
                   MAX = DATR(I,J,K)
                ENDIF
3            CONTINUE
             IF(MAX.EQ.0)GOTO 2
C--------------------------------------------------C
C---   SUMMATE H(n) x DT x XT(n) ----------C
C---   SUMMATE H(n) x DT
             SUM1 = 0.
             SUM2 = 0.
             DO 4 K = 1,IMGWRT - 5
                SUM1 = SUM1 + DATR(I,J,K)*DELTIME*XT(K)
                SUM2 = SUM2 + DATR(I,J,K)*DELTIME
4            CONTINUE
C--------------------------------------------------C
C--- MEAN TRANSIT TIME = SUM1/SUM2 --------C
C--- WRITE IT INTO RESULT ARRAY -----------C
             IF (ROUND.EQ.'Y'.OR.ROUND.EQ.'y') THEN
                RESULT(I,J,1) = 100.*(SUM1/SUM2)
                NORM = NORM * 100
             ELSE
                RESULT(I,J,1) = SUM1/SUM2
             ENDIF
             IF(RESULT(I,J,1).GT.32000) THEN
                RESULT(I,J,1) = 320000
                Q = Q + 1
```

```
      2           CONTINUE
      1       CONTINUE
              IF(Q.NE.0) WRITE(*,*)'WARNING ',Q,' OVERFLOWS.'
C------------------------------------------------C
C-- PUT NORM FACTOR IN ---C
              RESULT(1,1,1) = NORM
              RESULT(1,2,1) = NORM
              RESULT(2,1,1) = NORM
              RESULT(2,2,1) = NORM
              RETURN
              END
C------------------------------------------------C
C-- SUBROUTINE TO FIND TRANSFER FUNCITON ------C
C-- MAXIMUM AND WRITE RESULT TO MATRIX --------C
C-- THIS REPRESENTS ABSOLUTE FLOW -------------C
C-- THIS IMAGE GOES IN THE SECOND FRAME OF RESULT-C
C------------------------------------------------C
              SUBROUTINE FLOW(DATR,IMGWRT,RESULT,NORM)
C
              REAL*4 DATR(64,64,120),RESULT(64,64,5),MAX
              INTEGER*2 IMGWRT,NORM,Q
              CHARACTER*1 ROUND
C
              Q = 0
              WRITE(*,*)'SHOULD DATA BE SCALED BY A HUNDRED TO PREVENT'
              WRITE(*,*)'ROUNDOFF ERROR'
              READ(*,15)ROUND
      15      FORMAT(A)
              DO 1 I = 1, 64
                 DO 2 J = 1, 64
                    WRITE(*,*)I,J
                    MAX = 0.
                    DO 3 M = 1,IMGWRT
                       IF(DATR(I,J,M).GT.MAX) THEN
                          MAX = DATR(I,J,M)
                       ENDIF
      3             CONTINUE
                    IF(ROUND.EQ.'Y'.OR.ROUND.EQ.'y') THEN
                       RESULT(I,J,2) = 100* MAX
                       NORM = NORM *100
                    ELSE
                       RESULT(I,J,2) = MAX
                    ENDIF
                    IF (RESULT(I,J,2).GT.32000) THEN
                       RESULT(I,J,2) = 32000
                       Q = Q + 1
                    ENDIF
      2          CONTINUE
      1       CONTINUE
              IF(Q.NE.0)WRITE(*,*)'WARNING ',Q,' OVERFLOWS'
C- WRITE NORM FACTOR IN --------------
              RESULT(1,1,2) = NORM
              RESULT(1,2,2) = NORM
              RESULT(2,1,2) = NORM
              RESULT(2,2,2) = NORM
              RETURN
              END
C------------------------------------------------C
C--- SUBROUTINE TO AVERAGE LAST N-3 POINTS ----C
C--- AND GENERATE FUNCTIONAL IMAGE ----------C
C--- SHOULD FILL LOCATION 3 -----------------C
              SUBROUTINE ENDMEAN(DATR,IMGWRT,RESULT,NORM)
              REAL*4 DATR(64,64,120),RESULT(64,64,5),SUM,AVE
              INTEGER*2 IMGWRT,NORM,BEGIN,END,Q
              CHARACTER*1 ROUND
              Q = 0
      100     IFLAG = 0
              WRITE(*,*)'ENTER THE FRAME NUMBER TO BEGIN SUMMATION'
              READ(*,*) BEGIN
              WRITE(*,*)'ENTER THE FRAME NUMBER TO END SUMMATION'
              READ(*,*)END
              IF(END.LT.BEGIN)IFLAG = 1
              IF(END.GT.IMGWRT)IFLAG = 1
              IF(IFLAG.NE.0) GOTO 100
              WRITE(*,*)'SHOULD DATA BE SCALED BY A HUNDRED TO AVOID'
              WRITE(*,*)'ROUNDOFF ERROF'
              READ(*,15)ROUND
```

```
15      FORMAT(A)
        DO 1 I = 1, 64
           DO 2 J = 1, 64
              WRITE(*,*) I,J
              SUM = 0
              DO 3 M = BEGIN,END
                 SUM = SUM + DATR(I,J,M)
3             CONTINUE
              AVE = SUM/(END - BEGIN +1)
              IF (ROUND.EQ.'Y'.OR.ROUND.EQ.'w') THEN
                 RESULT(I,J,3) = 100*AVE
                 NORM = NORM*100
              ELSE
                 RESULT (I,J,3) = AVE
              ENDIF
              IF(RESULT(I,J,3).GT.32000)THEN
                 RESULT(I,J,3) = 32000
                 Q = Q + 1
              ENDIF
2          CONTINUE
1       CONTINUE
        IF(Q.NE.0)WRITE(*,*)'WARNING ',Q,' OVERFLOWS'
        RESULT(1,1,3) = NORM
        RESULT(1,2,3) = NORM
        RESULT(2,1,3) = NORM
        RESULT(2,2,3) = NORM
        RETURN
        END
```

```
C-----------------------------------------------------------------
C
C           REGIS_LIB  ---   VAX/VMS ReGIS GRAPHICS ROUTINES
C
C           FORTRAN-CALLABLE ROUTINES FOR IMAGE, GRAPHIC DISPLAY
C
C           NOTE -
C                  1. REGIS_INIT MUST BE CALLED FIRST !!
C
C                  2. IF RANDOM ERRORS OCCUR, TRY CALLING
C                     REGIS_SYNCH EVERY FEW CALLS TO RESYNCHRONIZE
C                     THE TERMINAL
C
C-----------------------------------------------------------------
C
C       REGIS_INIT
```

```
C           - INITIALIZE VT INTO ReGIS MODE
C
C-----------------------------------------------------------
C
C       REGIS_EXIT
C
C           - EXIT ReGIS MODE
C
C-----------------------------------------------------------
C
C       REGIS_SYNCH
C
C           - RESYNCHRONIZE ReGIS
C
C-----------------------------------------------------------
C
C       REGIS_ERASE
C
C           - CLEAR BIT PLANES
C
C-----------------------------------------------------------
C
C       REGIS_TEXT(TEXT,IXPOS,IYPOS)
C
C           - DISPLAY TEXT STRING
C
C           TEXT - ASCII TEXT STRING
C           IXPOS - X AXIS ADDRESS (0-799)
C           IYPOS - Y AXIS ADDRESS (0-479)
C
C-----------------------------------------------------------
C
C       REGIS_IMAGE(IMAGE,IXY,INC,JX,JY,IBOX)
C
C           - DISPLAY IXY*IXY IMAGE ON VT
C
C           IMAGE - INTEGER*2 MATRIX TO BE DIPLAYED
C           IXY - LINEAR DIMENSION OF MATRIX
C           INC - PIXEL INCREMENT FOR DISPLAY (1,2,4,etc.)
C           JX - X AXIS ADDRESS TO START DISPLAY (0-799)
C           JY - Y AXIS ADDRESS TO START DISPLAY (0-479)
C           IBOX - IF .NE.0 DRAW BOX AROUND IMAGE
C
C
C       REGIS_AXES(IXORIG,IYORIG,JXLEN,JYLEN)
C
C           - DRAW AXES FOR GRAPH
C
C           IXORIG - X AXIS ADDRESS OF GRAPH ORIGIN (0-799)
C           IYORIG - Y AXIS ADDRESS OF GRAPH ORIGIN (0-479)
C           JXLEN - X AXIS LENGTH
C           JYLEN - Y AXIS LENGTH
C
C-----------------------------------------------------------
C
C       REGIS_LABEL_X(TEXT,IXORIG,IYORIG,JXLEN,RXMAX,RXMIN,INC)
C
C           - LABEL X AXIS
C
C           TEXT - ASCII STRING FOR LABEL
C           IXORIG - X AXIS ADDRESS OF GRAPH ORIGIN (0-799)
C           IYORIG - Y AXIS ADDRESS OF GRAPH ORIGIN (0-479)
C           JXLEN - X AXIS LENGTH
C           RXMAX - X AXIS MAXIMUM
C           RXMIN - X AXIS MINIMUM
C           INC - INCREMENT FOR NUMERIC LABEL (NO. OF TICKS)
C
C-----------------------------------------------------------
C
C       REGIS_LABEL_Y(TEXT,IXORIG,IYORIG,JYLEN,RYMAX,RYMIN,INC)
C
C           - LABEL Y AXIS
C
C           TEXT - ASCII STRING FOR LABEL
C           IXORIG - X AXIS ADDRESS OF GRAPH ORIGIN (0-799)
C           IYORIG - Y AXIS ADDRESS OF GRAPH ORIGIN (0-479)
C           JYLEN - Y AXIS LENGTH
C           RYMAX - Y AXIS MAXIMUM
C           RYMIN - Y AXIS MINIMUM
C           INC - INCREMENT FOR NUMERIC LABEL (NO. OF TICKS)
```

```
C------------------------------------------------------------
C
C       REGIS_PLOT(Y,RYMAX,RYMIN,NPOINT,IXORIG,IYORIG,JYLEN,INC,INTENS)
C
C               - PLOT GRAPH
C
C               Y - REAL*4 VECTOR
C               RYMAX - Y AXIS MAXIMUM
C               RYMIN - Y AXIS MINIMUM
C               NPOINT - NUMBER OF POINTS TO PLOT
C               IXORIG - X AXIS ADDRESS OF GRAPH ORIGIN (0-799)
C               IYORIG - Y AXIS ADDRESS OF GRAPH ORIGIN (0-479)
C               JYLEN - Y AXIS LENGTH (FOR SCALING)
C               INC - X AXIS INCREMENT FOR PLOT
C               INTENS - INTENSITY LEVEL (0-3)
C
C------------------------------------------------------------
C
C       REGIS_LINE(IXSTART,IYSTART,JXEND,JYEND)
C
C               - DRAW LINE
C
C               IXSTART - X AXIS ADDRESS OF LINE START (0-799)
C               IYSTART - Y AXIS ADDRESS OF LINE START (0-479)
C               JXEND - X AXIS ADDRESS OF LINE END (0-799)
C               JYEND - Y AXIS ADDRESS OF LINE END (0-479)
C
C------------------------------------------------------------
C
C       REGIS_POS(IXPOS,IYPOS)
C
C               - POSITION CURSOR
C
C               IXPOS - X AXIS ADDRESS (0-799)
C               IYPOS - Y AXIS ADDRESS (0-479)
C
C------------------------------------------------------------
C
C       REGIS_BOX(IXLL,IYLL,JXUR,JYUR)
C
C               - DRAW BOX
C
C               IXLL - X AXIS ADDRESS OF LOWER LEFT CORNER (0-799)
C               IYLL - Y AXIS ADDRESS OF LOWER LEFT CORNER (0-479)
C               JXUR - X AXIS ADDRESS OF UPPER RIGHT CORNER (0-799)
C               JYUR - Y AXIS ADDRESS OF UPPER RIGHT CORNER (0-479)
C
C------------------------------------------------------------
C
C       REGIS_CIRCLE(IXCEN,IYCEN,JRADIUS)
C
C               - DRAW CIRCLE
C
C               IXCEN - X AXIS ADDRESS OF CENTER OF CIRCLE (0-799)
C               IYCEN - Y AXIS ADDRESS OF CENTER OF CIRCLE (0-479)
C               JRADIUS - RADIUS OF CIRCLE
C
C------------------------------------------------------------
C
C       REGIS_INTENS(INTENS)
C
C               - SET INTENSITY LEVEL FOR DRAWING
C
C               INTENS - INTENSITY LEVEL (0-3)
C
C------------------------------------------------------------
C
C       REGIS_PIXEL(IXPIX,IYPIX,INTENS)
C
C               - DRAW PIXEL
C
C               IXPIX - X AXIS ADDRESS OF PIXEL (0-799)
C               IYPIX - Y AXIS ADDRESS OF PIXEL (0-479)
C               INTENS - INTENSITY LEVEL (0-3)
C
C------------------------------------------------------------
C
C       CALL REGIS_PRINT(TEXT)
C
C               - OUTPUTS ASCII TEXT STRING AT CURRENT
C                 CURSOR POSITION TO SYS$OUTPUT
```

```
C          TEXT - ASCII TEXT STRING
C
C-----------------------------------------------------------
C
C          CALL REGIS_BINASC(NUM,ASCI,NCHR)
C
C               - CONVERTS INTEGER NUMBER TO ASCII STRING
C
C          NUM  - POSITIVE INTEGER*4 VALUE
C          ASCI - ASCII TEXT STRING TO RECEIVE RESULT
C          NCHR - NUMBER OF CHARACTERS TO CONVERT
C
C-----------------------------------------------------------
C
       SUBROUTINE REGIS_INIT
C
       BYTE REGIS(5)
       DATA REGIS/"33,'P','1','P',0/
C
       INTEGER*4 SYS$ASSIGN
       INTEGER*2 TT_IN_CHAN,TT_OUT_CHAN
C
       COMMON /REGIS_CHAN/ TT_IN_CHAN,TT_OUT_CHAN
C
       CALL SYS$ASSIGN('SYS$INPUT',TT_IN_CHAN,,)
       CALL SYS$ASSIGN('SYS$OUTPUT',TT_OUT_CHAN,,)
C
       CALL REGIS_PRINT(REGIS)
       RETURN
       END
C
C-----------------------------------------------------------
C
       SUBROUTINE REGIS_EXIT
C
       BYTE REGIS(3)
       DATA REGIS/"33,'\',0/
C
       CALL REGIS_PRINT(REGIS)
       RETURN
       END
C
C-----------------------------------------------------------
C
       SUBROUTINE REGIS_SYNCH
C
       CALL REGIS_PRINT(';')
       RETURN
       END
C
C-----------------------------------------------------------
C
       SUBROUTINE REGIS_ERASE
C
       CALL REGIS_PRINT('S(E)')
       RETURN
       END
C
C-----------------------------------------------------------
C
       SUBROUTINE REGIS_TEXT(TEXT,IXPOS,IYPOS)
C
       BYTE TEXT(1),CR(4)
C
       DATA CR/"15,'T',"47,0/
C
       CALL REGIS_POS(IXPOS,IYPOS)
C
       CALL REGIS_PRINT(CR)
       CALL REGIS_PRINT(TEXT)
       CALL REGIS_PRINT(CR(3))
C
       RETURN
       END
C
C-----------------------------------------------------------
C
CY     SUBROUTINE REGIS_IMAGE(IMAGE,IXY,INC,JX,JY,IBOX)
C
CX     INTEGER*2 IMAGE(IXY,IXY)
```

```
        JINC=INC
        KINC=-INC

MAX=MAXVECS(IMAGE,IXY*IXY)
        SCALE=4./FLOAT(MAX)
        NBOX=INC*IXY-1

JE=JX+(IXY-1)*JINC
        KE=JY+(IXY-1)*KINC

IF (IBOX.EQ.0) GOTO 10

CALL REGIS_INTENS(3)
        CALL REGIS_BOX(JX,JY,JX+NBOX,JY-NBOX)
10      J1=1

DO 110 J=JY,KE,KINC
        I1=1

DO 100 I=JX,JE,JINC
        N=IFIX(FLOAT(IMAGE(I1,J1))*SCALE)
        IF (N.LE.0) GOTO 100
        IF (N.GT.3) N=3

CALL REGIS_PIXEL(I,J,N)

100     I1=I1+1
110     J1=J1+1

IF (IBOX.EQ.0) GOTO 200
        CALL REGIS_INTENS(3)
        CALL REGIS_BOX(JX,JY,JX+NBOX,JY-NBOX)
200     CALL REGIS_SYNCH
        RETURN
        END

SUBROUTINE REGIS_AXES(IXORIG,IYORIG,JXLEN,JYLEN)

CALL REGIS_LINE(IXORIG,IYORIG,IXORIG,IYORIG-JYLEN)
        CALL REGIS_LINE(IXORIG,IYORIG,IXORIG+JXLEN,IYORIG)

RETURN
        END

SUBROUTINE REGIS_LABEL_X(TEXT,IXORIG,IYORIG,JXLEN,
     1  RXMAX,RXMIN,INC)

BYTE TEXT(1),TNUM(6),ENUM(9)

DATA TNUM/'','','','','0',0/
        DATA ENUM/'(','*','1','0','^','0','0',')',0/

RN=FLOAT(JXLEN)/FLOAT(INC)

XPOS=FLOAT(IXORIG)
        IYPOS=IYORIG

DO 10 I=1,INC+1

IXPOS=IFIX(XPOS+.5)
        CALL REGIS_POS(IXPOS,IYPOS)
        CALL REGIS_PRINT('VE,+101')
10      XPOS=XPOS+RN

XPOS=FLOAT(IXORIG+JXLEN-25)
        IYPOS=IYORIG+10
        R=RXMAX
        RINC=(RXMAX-RXMIN)/FLOAT(INC)

RX=ABS(RXMAX)
        SCALE=100.
        ISCALE=0
```

```
  10      IF (RX.LT.10.) GOTO 14
          RX=RX*.1
          ISCALE=ISCALE+1
          SCALE=SCALE*.1
          GOTO 13
  14      IF (RX.GT.1.) GOTO 16
          RX=RX*10.
          ISCALE=ISCALE-1
          SCALE=SCALE*10.
          GOTO 13
C
  16      DO 20 I=1,INC+1
C
          J=IFIX(R*SCALE)
          CALL REGIS_BINASC(IABS(J),TNUM(2),L3)
          TNUM(1)=' '
          IF (J.LT.0) TNUM(1)='-'
          TNUM(2)=TNUM(3)
          TNUM(3)=','
          IXPOS=IFIX(XPOS+.5)
          CALL REGIS_TEXT(TNUM,IXPOS,IYPOS)
C
          R=R-RINC
  20      XPOS=XPOS-RN
C
          IYPOS=IYORIG+45
          DO 30 I=1,80
  30      IF (TEXT(I).LE.0) GOTO 40
          GOTO 50
  40      I=9*(I-1)
          IE=I/20
          IF (ISCALE.NE.0) I=I+72
          IXPOS=IXORIG+(JXLEN-I)/2
C
          CALL REGIS_TEXT(TEXT,IXPOS,IYPOS)
          IF (ISCALE.EQ.0) GOTO 50
          CALL REGIS_BINASC(IABS(ISCALE),ENUM(5),L3)
          IF (ISCALE.LT.0) ENUM(4)='-'
          CALL REGIS_TEXT(ENUM,IXPOS+IE,IYPOS)
  50      CALL REGIS_SYNCH
          RETURN
          END
C
C
C
          SUBROUTINE REGIS_LABEL_Y(TEXT,IXORIG,IYORIG,JYLEN,
         &   RYMAX,RYMIN,INC)
C
          BYTE TEXT(19),TNUM(5),ENUM(11)
C
          DATA TNUM/' ','1',' ','0','0','0'/
          DATA ENUM/' ',' ',' ',' ','E',' ',' ',' ','0',' ',' '/
C
          RN=FLOAT(JYLEN)/FLOAT(INC)
C
          IXPOS=IXORIG
          YPOS=FLOAT(IYORIG)
C
          DO 10 I=1,INC+1
C
          IYPOS=IFIX(YPOS+.5)
          CALL REGIS_POS(IXPOS,IYPOS)
          CALL REGIS_PRINT('VT-103')
  10      YPOS=YPOS-RN

IXPOS=IXORIG-63
          YPOS=FLOAT(IYORIG-JYLEN-10)
          R=RYMAX
          RINC=(RYMAX-RYMIN)/FLOAT(INC)

RY=ABS(RYMAX)
          SCALE=100.
          ISCALE=0
          NEG=0

IF (RY.LT.10.) GOTO 14
          RY=RY*.1
          ISCALE=ISCALE+1
```

```
        SCALE=SCALE*.1
        GOTO 12
13      IF (RY.GT..1) GOTO 14
        Y=RY*10.
        ISCALE=ISCALE-1
        SCALE=SCALE*10.
        GOTO 14
C
16      DO 20 I=1,INC+1
C
        J=IFIX(R*SCALE)
        CALL REGIS_BINASC(IABS(J),TNUM(3),3)
        TNUM(1)=' '
        IF (J.GE.0) GOTO 18
        TNUM(1)='-'
        NEG=-1
18      TNUM(2)=TNUM(3)
        TNUM(3)=','
        IYPOS=IFIX(YPOS+.5)
        CALL REGIS_TEXT(TNUM,IXPOS,IYPOS)
C
        R=R+RINC
20      YPOS=YPOS+RN

IXPOS=IXORIG-80
        IF (NEG.LT.0) IXPOS=IXPOS-10
        DO 30 I=1,80
30      IF (TEXT(I).LE.0) GOTO 40
        GOTO 50
40      J=11*(I-1)
        IF (ISCALE.NE.0) J=J+88
        IYPOS=IYORIG-(JYLEN-1)/2
C
        CALL REGIS_POS(IXPOS,IYPOS)
        CALL REGIS_PRINT('T(B)(D,-1)(S24)')
        CALL REGIS_PRINT('*47')
        CALL REGIS_PRINT(TEXT)
        IF (ISCALE.EQ.0) GOTO 45
        CALL REGIS_BINASC(IABS(ISCALE),ENUM(3),2)
        IF (ISCALE.LT.0) ENUM(3)='-'
        CALL REGIS_PRINT(ENUM)
        CALL REGIS_PRINT(' (E)')
45      CALL REGIS_SYNCH
        RETURN
        END
C
C
C---------------------------------------------------------
CCC     SUBROUTINE REGIS_PLOT(Y,RYMAX,RYMIN,NPOINT,IXORIG,IYORIG,
CCC    1           JYLEN,INC,INTENS,IPATRN)
C
CCC     REAL*4 Y(1)
C
CCC     IXPOS=IXORIG
CCC     N=IYORIG-IFIX((Y(1)-RYMIN)*R)
CCC     CALL REGIS_POS(IXPOS,N)
C
CCC     R=FLOAT(JYLEN)/(RYMAX-RYMIN)
C
CCC     DO 100 I=1,NPOINT
CCC     IN=I+15
C
CCC     N=IYORIG-IFIX((Y(I)-RYMIN)*R)
C
CCC     CALL REGIS_VECT(IXPOS,N,INTENS,IPATRN)
C
CCC100  IXPOS=IXPOS+INC
C
CCC     CALL REGIS_SYNCH
C
CCC     RETURN
CCC     END
C
C---------------------------------------------------------
        SUBROUTINE REGIS_LINE(IXSTART,IYSTART,IXEND,IYEND)

BYTE LINE(11)
        BYTE PATT(6)
C
```

```
      DATA PATT/'W','(',',',',',',',',',',',',',0/

DATA LINE/'V','E','0','0','0',',','0','0','0','3',0/

CALL REGIS_PRINT(PATT)
      CALL REGIS_POS(IXSTART,IYSTART)
      CALL REGIS_BINASC(JXEND,LINE(3),3)
      CALL REGIS_BINASC(JYEND,LINE(7),3)
      CALL REGIS_PRINT(LINE)
C
      RETURN
      END
C
C-----------------------------------------------------------
C
      SUBROUTINE REGIS_POS(IXPOS,IYPOS)
C
      BYTE POSIT(11)
C
      DATA POSIT/'P','E','0','0','0',',','0','0','0','3',0/
C
      CALL REGIS_BINASC(IXPOS,POSIT(3),3)
      CALL REGIS_BINASC(IYPOS,POSIT(7),3)
      CALL REGIS_PRINT(POSIT)
C
      RETURN
      END
C
C-----------------------------------------------------------
C
      SUBROUTINE REGIS_BOX(IXLL,IYLL,JXUR,JYUR)
C
      CALL REGIS_LINE(IXLL,IYLL,IXLL,JYUR)
      CALL REGIS_LINE(IXLL,JYUR,JXUR,JYUR)
      CALL REGIS_LINE(JXUR,JYUR,JXUR,IYLL)
      CALL REGIS_LINE(JXUR,IYLL,IXLL,IYLL)
C
      RETURN
      END
C
C-----------------------------------------------------------
C
      SUBROUTINE REGIS_CIRCLE(IXCEN,IYCEN,IRADIUS)
C
      BYTE CIRCLE(8)
C
      DATA CIRCLE/'C','E','+','0','0','0','3',0/
C
      CALL REGIS_POS(IXCEN,IYCEN)
      CALL REGIS_BINASC(IRADIUS,CIRCLE(4),3)
      CALL REGIS_PRINT(CIRCLE)
C
      RETURN
      END
C
      SUBROUTINE REGIS_INTENS(INTEN)
C
      BYTE INTENS(6)
C
      DATA INTENS/'W','(','I','0',')',0/
C
      INTENS(4)=48+INTEN
      CALL REGIS_PRINT(INTENS)
C
      RETURN
      END
C
      SUBROUTINE REGIS_PIXEL(IXPIX,IYPIX,INTENS)
C
      BYTE PIXEL(4)
C
      DATA PIXEL/'V','(',')',0/
C
      CALL REGIS_POS(IXPIX,IYPIX)
      CALL REGIS_INTENS(INTENS)
      CALL REGIS_PRINT(PIXEL)
```

```
        RETURN
        END
C
C
        SUBROUTINE REGIS_VECT(IXPOS,IYPOS,INTENS,IPATRN)
C
        BYTE VECT(11)
        BYTE PAT(6)
C
        DATA PAT/'W',',','P',']','1',0/
        DATA VECT/'V','[','0','0','0',',','0','0','0',']',0/
C
        CALL REGIS_BINASC(IXPOS,VECT(3),3)
        CALL REGIS_BINASC(IYPOS,VECT(7),3)
        CALL REGIS_BINASC(IPATRN,PAT(5),1)
        CALL REGIS_PRINT(PAT)
        CALL REGIS_PRINT(VECT)
C
        RETURN
        END
C
        SUBROUTINE REGIS_KEY(NUM,TEXT1,TEXT2,TEXT3)
C
        BYTE TEXT1(1),TEXT2(1),TEXT3(1)
C
        CALL REGIS_POS(600,200)
        CALL REGIS_VECT(650,200,3,1)
        CALL REGIS_TEXT(TEXT1,670,195)
        IF(NUM.EQ.1)GOTO 148
        CALL REGIS_POS(600,225)
        CALL REGIS_VECT(650,225,3,2)
        CALL REGIS_TEXT(TEXT2,670,220)
        IF(NUM.EQ.2)GOTO 148
        CALL REGIS_POS(600,250)
        CALL REGIS_VECT(650,250,3,3)
        CALL REGIS_TEXT(TEXT3,670,245)
148     RETURN
        END
C
C
C
        SUBROUTINE REGIS_PRINT(TEXT)
C
        INCLUDE '($IODEF)'
C
        INTEGER*2 IOSB(4)
        INTEGER*4 SYS$QIOW,PARAM4
C
        DATA PARAM4/0/

INTEGER*2 TT_IN_CHAN,TT_OUT_CHAN

COMMON /REGIS_CHAN/ TT_IN_CHAN,TT_OUT_CHAN
C
        BYTE TEXT(1)

DO 5 I=1,80
5       IF (TEXT(I).LE.0) GOTO 10
        GOTO 20
C
10      L=I-1
        IF (L.LE.0) GOTO 20
        CALL SYS$QIOW(,%VAL(TT_OUT_CHAN),%VAL(IO$_WRITEVBLK)
     1  ,IOSB,,,%REF(TEXT),%VAL(L),,%VAL(PARAM4),,)
C
20      RETURN
        END
C
C
C
        SUBROUTINE REGIS_BINASC(NUM,ASCI,NCHR)
C
        BYTE ASCI(1),CHAR(6)
C
        IF (NCHR.GT.6) GOTO 100
C
        DO 1 I=1,NCHR
1       ASCI(I)='0'
C
        I=NUM
        K=0
        L=NCHR
```

```
C
    10        IJ=0
C
    20        I=I-10
              IF (I.LT.0) GOTO 30
              IJ=IJ+1
              GOTO 20
C
    30        I=I+10
              K=K+1
              CHAR(K)=I+48
              IF (IJ.EQ.0) GOTO 40
              I=IJ
              GOTO 10
C
    40        IF (K.GT.NCHR) GOTO 100
C
              I=1
C
    50        ASCI(L)=CHAR(I)
              L=L-1
              I=I+1
              IF (I.LE.K) GOTO 50
C
    100       RETURN
              END
```

I claim:

1. An apparatus for the extraction of blood flow rate in an internal organ of a human body by analysis of a time sequence of scintigraphic images taken from the internal organ comprising:
   means for digitizing scinitgraphic data, whose amplitude represents the time sequence of activity of a radioactive tracer in the internal organ;
   means for storing and retrieving a first plurality of orthonormal functions $c_z$;
   means for storing and retrieving a second plurality of orthonormal functions $d_z$ having the same number of elements as function $c_z$;
   means for calculating a set of values $f_z$ from the product of the elements of $d_z$ and the amplitude value of each pixel of each of said images; and
   means for calculating said blood flow rate from the sum of the products of each individual element of $c_z$ and $f_z$.

2. A method of extracting information about blood flow rate in an internal organ from a sequence of digitized scintigraphic images comprising the steps of:
   injecting a radioactive tracer into the blood stream;
   monitoring scintigraphic activity at an area of interest;
   digitizing said scintigraphic activity, whose amplitude represents the time sequence of concentration of said tracer in the blood stream at said area of interest to form a time sequence of images;
   identifying a first plurality of orthonormal functions $c_z$ having a number of elements equal to the product of the number of images times the number of orthonormal polynomials used within said $c_z$ functions
   applying a second plurality of orthonormal functions $d_z$ having the same number of elements as said function cz to calculate a set of values $f_z$ from the product of the elements of $d_z$ and the amplitude value of each pixel of each of said images; and
   calculating said blood flow rate from the sum of the products of each individual element of $c_z$ and $f_z$.

3. An apparatus for extraction of features of a portion of space by analyzing a time sequence of RADAR system acquired impages, comprising:
   means for digitizing RADAR system acquired data in the form of images, said images having pixels whose amplitudes represent the amount of microwave energy returned from the portion of space;
   means for computing a first plurality of orthonormal functions, each of said first orthonormal functions having a plurality of first elements, said functions derived from known characterisitcis of said RADAR system;
   means for computing a second plurality of orthonormal functions, each of said second orthonormal functions having a plurality of second elements;
   means for computing a first product for each pixel element contained in said sequence of images, said first product being computed from each second element of said second plurality of orthonormal functions and pixels from said images; and
   means for computing a sum of a second product, said second product computed from each first element of said first orthonormal functions and each element of said first product.

4. A method for the extraction of features contained within a time sequence of RADAR system acquired images, comprising:
   digitizing RADAR system acquired data in the form of images, said images having pixels whose amplitudes represent the amount of microwave energy returned from a portion of space;
   computing a first plurality of orthonormal functions, each of said first orthonormal functions having a plurality of first elements, said functions derived from known characteristics of said RADAR system;
   computing a second plurality of orthonormal functions, each of said second orthonormal functions having a plurality of second elements;
   computing a first product for each pixel element contained in said sequence of images, said first product computed from each second element of said second orthonormal functions and pixels from said images;
   computing a sum of a second product, said second product computed from each first element of said first orthonormal functions and each element of said first product.

5. An apparatus for the extraction of geophysical details about a selected area by analyzing a time sequence of seismic images comprising:

means for collecting and digitizing seismic data in the form of seismic images, said seismic images having pixels whose amplitudes represent the amount of shock energy returned from the selected area;

means for computing a first plurality of orthonormal functions, each of said first orthonormal functions having a plurality of first elements, said functions being related to the known transfer function of said means for collecting seismic data;

means for computing a second plurality of orthonormal functions, each of said second orthonormal functions having a plurality of second elements;

means for computing a first product for each pixel element contained in said sequence of images, said first product being computed from each second element of said second plurality of orthonormal functions and pixels from said images; and means for computing a sum of a second product, said second product computed from each first element of said first orthonormal functions and each element of said first product.

6. A method for the extraction of geophysical details contained within a time sequence of seismic images acquired with a means for collecting seismic data, comprising:

collecting and digitizing seismic data in the form of images, said images having pixels whose amplitudes represent the amount of shock energy returned from an area to be surveyed;

computing a first plurality of orthonormal functions, each of said first orthonormal functions having a plurality of first elements, said first orthonormal functions being related to the known transfer function of said means for collecting seismic data;

computing a second plurality of orthonormal functions, each of said second functions having a pluurality of second elements;

computing a first product for each pixel element contained in said sequence of images, said first product computed from each second element of said second orthonormal functions and pixels from said images;

computing a sum of a second product, said second product computed from each first element of said first orthonormal functions and each element of said first product.

* * * * *

UNITED STATES PATENT AND TRADEMARK OFFICE
CERTIFICATE OF CORRECTION

PATENT NO. : 5,249,122

DATED : September 28, 1993

INVENTOR(S) : Peter Stritzke

It is certified that error appears in the above-indentified patent and that said Letters Patent is hereby corrected as shown below:

On title page, item [57] Abstract, "disclose" should read --discloses--;

Col. 2, line 45, "present the" should read --the present--;

Col. 7, line 5, that portion of equ. 8 reading "$(x,y,t_n°$" should read --$(x,y,t_n°)$--;

Col. 7, line 16, "$U.t \leq T$" should read --$U.\Delta t \leq T$--;

Col. 7, line 35, "$1(x,y,t_n)=En \cdot I°(x,y,t_N°) \; \beta_n \cdot I°(x,y,t_n°) \cdot$" should read --$I(x,y,t_n)=\alpha_n \cdot I°(x,y,t_{n+1}°)+\beta_n \cdot I°(x,y,t_n°) \cdot$--;

Col. 7, following line 55, insert --Here it is introduced a notation that proves to be a powerful tool in solving our inverse problem, called Dirac notation. Given two functions k and g continuously dependent on a set of variables $k=k(t)$ and $g=g(t)$, and defined in the interval $a \leq t \leq b$, the scalar or inner product will then be given by $$<k|g> = \int_a^b k(t') \cdot g(t') \cdot dt' \qquad (A.1)$$

One may then interpret the $|g>$ (or ket) as a column matrix with the components $g_i$ and $<k|$ (or bra) as a row matrix with the components $k_i$ [20]. Assuming the functions $<k|$ and $|g>$ to be elements of the Hilbert space [linearity, existence of scalar product (equ.A.1), existence of a length (norm), and completeness], the functions $<k|$ and $|g>$ can be called vectors. This is due to the similarity of this concept to the

UNITED STATES PATENT AND TRADEMARK OFFICE
CERTIFICATE OF CORRECTION

PATENT NO. : 5,249,122

DATED : September 28, 1993

INVENTOR(S) : Peter Stritzke

It is certified that error appears in the above-indentified patent and that said Letters Patent is hereby corrected as shown below:

definition of two finite-dimensional vectors. Let h be a linear operator acting on $|g\rangle$. This may be written in either of two equivalent ways $|h|g\rangle$ or $|hg\rangle$. The operator $|h|$ can be quite general, and this operation is given as $$|h|g\rangle = \int_0^t h(t-t') \cdot g(t') \cdot dt' \qquad (A.2)$$

The relation $$\langle h|g| = \langle g|h|^+ \qquad (A.3)$$

is often called the "turn over rule", where $|h|^+$ is called the adjoint operator to $|h|$. In the following it will be shown how to derive the adjoint operator from equ.A1 and equ.A2. With these equations it follows that $$\langle k|h|g\rangle = \int_0^T k(t) \cdot \int_0^t h(t-t') \cdot g(t') \cdot dt \cdot 'dt \qquad (A.4)$$

By exchanging the order of integration (Fubinis theorem [20]) equ.A4 can be written as $$\langle k|h|g\rangle = \int_0^T g(t') \cdot dt' \cdot \int_{t'}^T h(t-t') \cdot k(t) \cdot dt \qquad (A.5)$$

and by exchanging the variables $t' \cdot dt'$ with $t \cdot dt$ it follows

UNITED STATES PATENT AND TRADEMARK OFFICE
CERTIFICATE OF CORRECTION

PATENT NO. : 5,249,122

DATED : September 28, 1993

INVENTOR(S) : Peter Stritzke

It is certified that error appears in the above-indentified patent and that said Letters Patent is hereby corrected as shown below:

$$<k|h|g> = \int_0^T g(t) \cdot dt \cdot \int_t^T h(t-t') \cdot k(t') \cdot dt' \quad (A.6)$$

Writing equ.A6 in Dirac notation one finds $$<k|h|g> = <g|h|^+k> \quad (A.7)$$

The comparison of equ.A7 with equ.A2 delivers the final formulation for the adjoint operator $|h|^+$:

$$|h|^+g> = \int_0^{T-t} h(t'-t) \cdot g(t') \cdot dt = \int_0^T h(t') \cdot g(t'+t) \cdot dt' \quad (A.8)$$

Equ.A8 was used to calculate a function system $b_k=|B|^+p_k>$ (equ.16), where B is the blood input function and $p_k$ is a set of Legendre polynomials.--;

Col. 11, line 60, "$c_3(t_2)$" should read --$C_3(t_2)$--;

Col. 12, line 5, "$d_3(t_2)$" should read --$D_3(t_2)$--;

Col. 12, line 14, "equ. 8-2" should read --equ. 8-12--;

UNITED STATES PATENT AND TRADEMARK OFFICE
CERTIFICATE OF CORRECTION

PATENT NO. : 5,249,122

DATED : September 28, 1993

INVENTOR(S) : Peter Stritzke

It is certified that error appears in the above-indentified patent and that said Letters Patent is hereby corrected as shown below:

Col. 12, following line 55, insert --<u>Discrete deconvolution (matrix method):</u>

Let B(t) and A(t) be the respective blood input and organ output functions of a linear system with a linear response function h(t). The convolution integral is:

$$A(t) = \int_0^t h(t-t') \cdot B(t') \cdot dt' \qquad (B1)$$

The discrete form of equ.B1 is given by:

$$A_n = \sum_{k=0}^{n} h_{n-k} \cdot B_k \cdot \Delta t, \qquad (B2)$$

Solving equ.B2 for $h_k$, k=1,...n yields:

$$\begin{aligned} h_0 &= a_0 \cdot \Delta t / B_0 \\ h_1 &= (A_1 / \Delta t - h_0 \cdot B_1) / B_0 \\ &\vdots \\ h_n &= (A_n / \Delta t - \sum_{i=1}^{n} B_i \cdot h_{n-i}) / B_0 \end{aligned} \qquad (B3)$$

This system of equations constitutes a single mechanism for discrete deconvolution.

UNITED STATES PATENT AND TRADEMARK OFFICE
CERTIFICATE OF CORRECTION

PATENT NO. : 5,249,122

DATED : September 28, 1993

INVENTOR(S) : Peter Stritzke

It is certified that error appears in the above-indentified patent and that said Letters Patent is hereby corrected as shown below:

The Fourier method: In the frequency domain equ.B1 becomes:

$$F\{A(t)\} = F\{h(t)\} \cdot F\{B(t)\} \qquad (B4)$$

where $F\{\}$ stands for discrete Fourier transformation, and "$\cdot$" denotes multiplication. The LRF can then be obtained by inverse Fourier transformation of the quotient:

$$h(t) = F^{-1}\{F\{A(t)\}/F\{B(t)\}\} \qquad (B5)$$

Equ.B5 was implemented using fast Fourier transform programs described in [16]. Because data are not periodic or consist of non-periodic stretch of finite length, data were extended to 256 data points by zero padding. They were arranged in wrap-around order.--;

Col. 12, line 63, that portion of equ. 37 reading "$B(n \cdot \Delta t)$," should read --$B(n \cdot \Delta t) = B(t_n)$,--;

Col. 15, line 46, "according" should read --according to--;

Col. 17, line 20, "optimized for" should read --optimized--;

Col. 20, line 29, "showed" should read --shown--;

UNITED STATES PATENT AND TRADEMARK OFFICE
CERTIFICATE OF CORRECTION

PATENT NO. : 5,249,122
DATED : September 28, 1993
INVENTOR(S) : Peter Stritzke

It is certified that error appears in the above-indentified patent and that said Letters Patent is hereby corrected as shown below:

Col. 20, line 61, "no" should read —not—.

Signed and Sealed this

Twenty-first Day of February, 1995

Attest:

BRUCE LEHMAN

*Attesting Officer*   *Commissioner of Patents and Trademarks*